(12) United States Patent
Kobayashi et al.

(10) Patent No.: US 11,634,696 B2
(45) Date of Patent: Apr. 25, 2023

(54) MUTANT POLYHYDROXYALKANOATE SYNTHETASE, GENE AND TRANSFORMANT THEREOF, AND METHOD FOR PRODUCING POLYHYDROXYALKANOATE

(71) Applicant: KANEKA CORPORATION, Osaka (JP)

(72) Inventors: Shingo Kobayashi, Takasago (JP); Shunsuke Sato, Takasago (JP); Naoaki Taoka, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 17/252,086

(22) PCT Filed: Jun. 12, 2019

(86) PCT No.: PCT/JP2019/023223
§ 371 (c)(1),
(2) Date: Dec. 14, 2020

(87) PCT Pub. No.: WO2019/240155
PCT Pub. Date: Dec. 19, 2019

(65) Prior Publication Data
US 2021/0254028 A1 Aug. 19, 2021

(30) Foreign Application Priority Data
Jun. 15, 2018 (JP) .............................. JP2018-114298

(51) Int. Cl.
| | | |
|---|---|---|
| *C12N 9/10* | (2006.01) | |
| *C12N 15/52* | (2006.01) | |
| *C12N 1/20* | (2006.01) | |
| *C12P 7/62* | (2022.01) | |

(52) U.S. Cl.
CPC ............ *C12N 9/1029* (2013.01); *C12N 1/20* (2013.01); *C12N 15/52* (2013.01); *C12P 7/62* (2013.01)

(58) Field of Classification Search
None
See application file for complete search history.

(56) References Cited

U.S. PATENT DOCUMENTS

2005/0009949 A1  1/2005  Doi et al.
2021/0254028 A1* 8/2021  Kobayashi ................ C12P 7/62

FOREIGN PATENT DOCUMENTS

WO     WO 03/050277 A1    6/2003

OTHER PUBLICATIONS

UniProt Accession No. K1JM10_9GAMM, published Nov. 28, 2012 (Year: 2012).*
UniProt Accession No. A0A023RIH2_AERME, published Jul. 9, 2014 (Year: 2014).*
Kichise, T. et al., "Enhanced Accumulation and Changed Monomer Composition in Polyhydroxyalkanoate (PHA) Copolyester by In Vitro Evolution of *Aeromonas caviae* PHA Synthase", Applied and Environmental Microbiology, 2002, vol. 68, No. 5, pp. 2411-2419.
Sato, S. et al., "Regulation of 3-hydroxyhexanoate composition in PHBH synthesized by recombinant *Cupriavidus necator* H16 from plant oil by using butyrate as a co-substrate", Journal of Bioscience and Bioengineering, 2015, vol. 120, No. 3, pp. 246-251.
UniProtKB, Accession No. A0A2I6QQP5, URL: <https://www.uniprot.org/uniprot/A0A2I6QQP5>, May 23, 2018 uploaded; retrieved on Sep. 5, 2019; 4 pages.
UniProtKB, Accession No. A0A291U3A1, URL: <https://www.uniprot.org/uniprot/A0A291U3A1>, Feb. 28, 2018 uploaded; retrieved on Sep. 5, 2019; 4 pages.
Tsuge, T. et al., "Combination of N149S and D171G mutations in *Aeromonas caviae* polyhydroxyalkanoate synthase and impact on polyhydroxyalkanoate biosynthesis"; FEMS Microbiol Lett., 2007, vol. 277, pp. 217-222.
International Search Report dated Sep. 17, 2019 in PCT/JP2019/023223 filed on Jun. 12, 2019 (2 pages).

* cited by examiner

*Primary Examiner* — Richard C Ekstrom
(74) *Attorney, Agent, or Firm* — Oblon, McClelland, Maier & Neustadt, L.L.P.

(57) ABSTRACT

Provided is a mutant polyhydroxyalkanoate synthetase having an amino acid sequence which has 85% or more sequence identity with the amino acid sequence of SEQ ID NO: 1 and which contains a mutation of substitution of at least one of the amino acids at the 27th to 33rd, 39th, 56th, 106th, 129th, 144th, 165th, 170th and 172nd to 187th positions from the N-terminus of the amino acid sequence of SEQ ID NO: 1 with another amino acid.

30 Claims, No Drawings
Specification includes a Sequence Listing.

SEQUENCE LISTING

```
<160> NUMBER OF SEQ ID NOS: 53

<210> SEQ ID NO 1
<211> LENGTH: 594
<212> TYPE: PRT
<213> ORGANISM: Aeromonas caviae

<400> SEQUENCE: 1

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190
```

```
Leu Asn Ile Arg Leu Thr Asp Glu Ser Ala Phe Glu Leu Gly Arg Asp
                195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
                260                 265                 270

Phe Met Ile Ser Trp Arg Asn Pro Gly Val Ala Gln Ala Gln Ile Asp
                275                 280                 285

Leu Asp Asp Tyr Val Val Asp Gly Val Ile Ala Ala Leu Asp Gly Val
                290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Leu Arg Arg
                325                 330                 335

Gln Lys Gln Arg Val Arg Thr Ala Thr Leu Phe Thr Thr Leu Leu Asp
                340                 345                 350

Phe Ser Gln Pro Gly Glu Leu Gly Ile Phe Ile His Glu Pro Ile Ile
                355                 360                 365

Ala Ala Leu Glu Ala Gln Asn Glu Ala Lys Gly Ile Met Asp Gly Arg
                370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
                420                 425                 430

His Asn Ser Leu Leu Arg Arg Leu Tyr Leu Glu Asn Gln Leu Val Lys
                435                 440                 445

Gly Glu Leu Lys Ile Arg Asn Thr Arg Ile Asp Leu Gly Lys Val Lys
450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
                500                 505                 510

Ala Asn Lys Tyr Gly Phe Trp His Asn Gly Ala Glu Ala Glu Ser Pro
                515                 520                 525

Glu Ser Trp Leu Ala Gly Ala Thr His Gln Gly Gly Ser Trp Trp Pro
530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
                580                 585                 590

Ala Ala

<210> SEQ ID NO 2
```

```
<211> LENGTH: 842
<212> TYPE: DNA
<213> ORGANISM: Ralstonia eutropha

<400> SEQUENCE: 2
cccgggcaag taccttgccg acatctatgc gctggcgcgc acgcgcctgg cgcgcgccgg      60
ctgtaccgag gtctacggcg gcgacgcctg caccgtggcc gacgccggtc gcttctactc     120
ctatcggcgc gatggcgtga ccggccgcat ggccagcctg gtctggctgg cggactgagc     180
ccgccgctgc ctcactcgtc cttgcccctg gccgcctgcg cgcgctcggc ttcagccttg     240
cgtcggcggc ggccgggcgt gcccatgatg tagagcacca cgccaccgg cgccatgcca      300 tacatcagga aggtggcaac gcctgccacc acgttgtgct cggtgatcgc catcatcagc    360
gccacgtaga gccagccaat ggccacgatg tacatcaaaa attcatcctt ctcgcctatg    420
ctctggggcc tcggcagatg cgagcgctgc ataccgtccg gtaggtcggg aagcgtgcag   480
tgccgaggcg gattcccgca ttgacagcgc gtgcgttgca aggcaacaat ggactcaaat    540
gtctcggaat cgctgacgat tcccaggttt ctccggcaag catagcgcat ggcgtctcca   600
tgcgagaatg tcgcgcttgc cggataaaag gggagccgct atcggaatgg acgcaagcca   660
cggccgcagc aggtgcggtc gagggcttcc agccagttcc agggcagatg tgccggcaga   720
ccctcccgct ttgggggagg cgcaagccgg gtccattcgg atagcatctc cccatgcaaa    780
gtgccggcca gggcaatgcc cggagccggt tcgaatagtg acggcagaga gacaatcaaa   840
tc                                                                   842

<210> SEQ ID NO 3
<211> LENGTH: 268
<212> TYPE: DNA
<213> ORGANISM: Ralstonia eutropha

<400> SEQUENCE: 3
catggccctc gccggagcgc cccggagtgg cgtcacagcc gctcccgtgt atcgccagca     60
acgttgtttg tgcattgcac aaaatccact tgacattgga tctggcgccc ctaaaatagg   120
aattgttgcg gcgcaccaaa taagaaatgc gccttgaccc acccacacgc ctgggctggc   180
cgaatcgggc acaacaccgt cacggccctg acatctaggc ggcttaattt gctagacctt   240
gaagttcacc actggagacc agcaattg                                       268

<210> SEQ ID NO 4
<211> LENGTH: 123
<212> TYPE: DNA
<213> ORGANISM: Escherichia coli

<400> SEQUENCE: 4
gcgcaacgca attaatgtga gttagctcac tcattaggca ccccaggctt tacactttat     60
gcttccggct cgtatgttgt gtggaattgt gagcggataa caatttcaca caggaaacaa   120
ttg                                                                  123

<210> SEQ ID NO 5
<211> LENGTH: 232
<212> TYPE: DNA
<213> ORGANISM: Escherichia coli

<400> SEQUENCE: 5
tgcttctggc gtcaggcagc catcggaagc tgtggtatgg ctgtgcaggt cgtaaatcac     60
tgcataattc gtgtcgctca aggcgcactc ccgttctgga taatgttttt tgcgccgaca   120
```

```
tcataacggt tctggcaaat attctgaaat gagctgttga caattaatca tcgaactagt    180
taactagtac gcaagttcac agcggataac aatttcacac aggaaacaat tg            232

<210> SEQ ID NO 6
<211> LENGTH: 123
<212> TYPE: DNA
<213> ORGANISM: Artificial Sequence
<220> FEATURE:
<223> OTHER INFORMATION: Mutated promoter sequence derived from
      Escherichia coli

<400> SEQUENCE: 6
gcgcaacgca attaatgtga gttagctcac tcattaggca ccccaggctt tacactttat    60
gcttccggct cgtataatgt gtggaattgt gagcggataa caatttcaca caggaaacaa    120
ttg                                                                  123

<210> SEQ ID NO 7
<211> LENGTH: 236
<212> TYPE: DNA
<213> ORGANISM: Artificial Sequence
<220> FEATURE:
<223> OTHER INFORMATION: Mutated promoter sequence derived from
      Escherichia coli

<400> SEQUENCE: 7
caattgtgct tctggcgtca ggcagccatc ggaagctgtg gtatggctgt gcaggtcgta    60
aatcactgca taattcgtgt cgctcaaggc gcactcccgt tctggataat gttttttgcg    120
ccgacatcat aacggttctg gcaaatattc tgaaatgagc tgttgacaat taatcatccg    180
gctcgtataa tgtgtggaat tgtgagcgga taacaatttc acacaggaaa caattg        236

<210> SEQ ID NO 8
<211> LENGTH: 237
<212> TYPE: DNA
<213> ORGANISM: Artificial Sequence
<220> FEATURE:
<223> OTHER INFORMATION: Mutated promoter sequence derived from
      Escherichia coli

<400> SEQUENCE: 8
caattgtgct tctggcgtca ggcagccatc ggaagctgtg gtatggctgt gcaggtcgta    60
aatcactgca taattcgtgt cgctcaaggc gcactcccgt tctggataat gttttttgcg    120
ccgacatcat aacggttctg gcaaatattc tgaaatgagc tgttgacaat taatcatcgc    180
ggctcgtata atgtgtggaa ttgtgagcgg ataacaattt cacacaggaa acaattg       237

<210> SEQ ID NO 9
<211> LENGTH: 235
<212> TYPE: DNA
<213> ORGANISM: Artificial Sequence
<220> FEATURE:
<223> OTHER INFORMATION: Mutated promoter sequence derived from
      Escherichia coli

<400> SEQUENCE: 9
caattgtgct tctggcgtca ggcagccatc ggaagctgtg gtatggctgt gcaggtcgta    60
aatcactgca taattcgtgt cgctcaaggc gcactcccgt tctggataat gttttttgcg    120
ccgacatcat aacggttctg gcaaatattc tgaaatgagc tgttgacaat taatcatcgg    180
ctcgtataat gtgtggaatt gtgagcggat aacaatttca caggaaac aattg           235
```

<210> SEQ ID NO 10
<211> LENGTH: 128
<212> TYPE: DNA
<213> ORGANISM: Artificial Sequence
<220> FEATURE:
<223> OTHER INFORMATION: Mutated promoter sequence derived from
      Escherichia coli

<400> SEQUENCE: 10
caattggcgc aacgcaatta atgtgagtta gctcactcat taggcacccc aggctttaca    60
cttatgcttc cggctcgtat gttgtgtgga attgtgagcg ataacaatt tcacacagga   120 aacaattg                                                            128

<210> SEQ ID NO 11
<211> LENGTH: 24
<212> TYPE: DNA
<213> ORGANISM: Ralstonia eutropha

<400> SEQUENCE: 11
cacgtgcaga gagacaatca aatc                                           24

<210> SEQ ID NO 12
<211> LENGTH: 1056
<212> TYPE: DNA
<213> ORGANISM: Ralstonia eutropha

<400> SEQUENCE: 12
gcgcgcattt aaatctgcca ccacgttgtg ctcggtgatc gccatcatca gcgccacgta    60
gagccagcca atggccacga tgtacatcaa aaattcatcc ttctcgccta tgctctgggg   120
cctcggcaga tgcgagcgct gcataccgtc cggtaggtcg ggaagcgtgc agtgccgagg   180
cggattcccg cattgacagc gcgtgcgttg caaggcaaca atggactcaa atgtctcgga   240
atcgctgacg attcccaggt ttctccggca agcatagcgc atggcgtctc catgcgagaa   300
tgtcgcgctt gccggataaa aggggagccg ctatcggaat ggacgcaagc cacggccgca   360
gcaggtgcgg tcgagggctt ccagccagtt ccagggcaga tgtgccggca gaccctcccg   420 cttgggga ggcgcaagcc gggtccattc ggatagcatc tccccatgca aagtgccggc   480
cagggcaatg cccggagccg gttcgaatag tgacggcaga gagacaatca aatccgcttg   540
catgagtgcc ggcgtgcgtc atgcacgcg ccggcaggcc tgcaggttcc ctcccgtttc   600
cattgaaagg actacacaat gactgacgtt gtcatcgtat ccgccgcccg caccgcggtc   660
ggcaagtttg gcggctcgct ggccaagatc ccggcaccgg aactgggtgc cgtggtcatc   720
aaggccgcgc tggagcgcgc cggcgtcaag ccggagcagg tgagcgaagt catcatgggc   780
caggtgctga ccgccggttc gggccagaac cccgcacgcc aggccgcgat caaggccggc   840
ctgccggcga tggtgccggc catgaccatc aacaaggtgt gcggctcggg cctgaaggcc   900
gtgatgctgg ccgccaacgc gatcatggcg ggcgacgccg agatcgtggt ggccggcggc   960
caggaaaaca tgagcgccgc cccgcacgtg ctgccgggct cgcgcgatgg tttccgcatg  1020
ggcgatgcca agctggtcga caatttaaat gcgcgc                            1056

<210> SEQ ID NO 13
<211> LENGTH: 2132
<212> TYPE: DNA
<213> ORGANISM: Artificial Sequence
<220> FEATURE:
<223> OTHER INFORMATION: Gene expressing cassette

```
<400> SEQUENCE: 13
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggccc tggcccacta caatgacaag ctgctggcca     360
tggccaaggc ccagacagag cgcaccgccc aggcgctgct gcagaccaat ctggacgatc     420
tgggccaggt gctggagcag ggcagccagc aaccctggca gctgatccag cccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctatgac tacctcaagc agtcctacct gctcaccgcc aggcacctgc     660
tggcctcggt ggatgccctg gagggcgtcc ccagaagag ccgggagcgg ctgcgtttct     720
tcacccgcca gtacgtcagc gccatggccc cagcaactt cctggccacc aaccccgagc     780
tgctcaagct gaccctggag tccggcggcc agaacctggt gcgcggactg gccctcttgg     840
ccgaggatct ggagcgcagc gccgatcagc tcaacatccg cctgaccgac gaatccgcct     900
tcgagctcgg gcgggatctg gccctgaccc cgggccgggt ggtgcagcgc accgagctct     960
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgcccctgtc gctcgccatg ggctggctgg cggcgcggcg ccagaagcag cgggtgcgca    1320
ccgccaccct gttcactacc ctgctggact ctcccagcc cggggagctt ggcatcttca    1380
tccacgagcc catcatagcg cgcgtcgagg cgcaaaatga ggccaagggc atcatggacg    1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt tctctacctgg    1620
agaaccagct ggtgaagggg gagctcaaga tccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg gagtccggcc    1800
acatcgccgg catcatcaac cgccggccg ccaacaagta cggcttctgg cacaacgggg    1860
ccgaggccga gagcccggag agctggctgg caggggcgac gcaccaggggc ggctcctggt    1920
ggccccgagat gatgggcttt atccagaacc gtgacgaagg gtcagagccc gtccccgcgc    1980
gggtcccgga ggaagggctg gccccccgccc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                  2132
```

<210> SEQ ID NO 14
<211> LENGTH: 594
<212> TYPE: PRT
<213> ORGANISM: Aeromonas caviae

<400> SEQUENCE: 14

```
Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Ser Ala Met Ala Pro Ser Asn Phe Leu Ala Thr Asn
145                 150                 155                 160

Pro Glu Leu Leu Lys Leu Thr Leu Glu Ser Gly Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
    370                 375                 380

Gln Leu Ala Val Ser Phe Ser Leu Leu Arg Glu Asn Ser Leu Tyr Trp
385                 390                 395                 400
```

```
Asn Tyr Tyr Ile Asp Ser Tyr Leu Lys Gly Gln Ser Pro Val Ala Phe
            405                 410                 415
Asp Leu Leu His Trp Asn Ser Asp Ser Thr Asn Val Ala Gly Lys Thr
        420                 425                 430
His Asn Ser Leu Leu Arg Arg Leu Tyr Leu Glu Asn Gln Leu Val Lys
            435                 440                 445
Gly Glu Leu Lys Ile Arg Asn Thr Arg Ile Asp Leu Gly Lys Val Lys
    450                 455                 460
Thr Pro Val Leu Leu Val Ser Ala Val Asp Asp His Ile Ala Leu Trp
465                 470                 475                 480
Gln Gly Thr Trp Gln Gly Met Lys Leu Phe Gly Gly Glu Gln Arg Phe
                485                 490                 495
Leu Leu Ala Glu Ser Gly His Ile Ala Gly Ile Ile Asn Pro Pro Ala
            500                 505                 510
Ala Asn Lys Tyr Gly Phe Trp His Asn Gly Ala Glu Ala Glu Ser Pro
        515                 520                 525
Glu Ser Trp Leu Ala Gly Ala Thr His Gln Gly Gly Ser Trp Trp Pro
    530                 535                 540
Glu Met Met Gly Phe Ile Gln Asn Arg Asp Glu Gly Ser Glu Pro Val
545                 550                 555                 560
Pro Ala Arg Val Pro Glu Glu Gly Leu Ala Pro Ala Pro Gly His Tyr
                565                 570                 575
Val Lys Val Arg Leu Asn Pro Val Phe Ala Cys Pro Thr Glu Glu Asp
            580                 585                 590
Ala Ala
```

<210> SEQ ID NO 15
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 15

```
cctagggtgt acattgcgct gaaagaaggg ccaattgtgc ttctggcgtc aggcagccat     60
cggaagctgt ggtatggctg tgcaggtcgt aaatcactgc ataattcgtg tcgctcaagg    120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ctctacagag cgcaccgccc aggcgctgct gcagaccaat ctggacgatc    420
tgggccaggt gctggagcag ggcagccagc aaccctggca gctgatccag gcccagatga    480
actggtggca ggatcagctc aagctgatgc agcacaccct gctcaaaagc gcaggccagc    540
cgagcgagcc ggtgatcacc ccggagcgca gcgatcgccg cttcaaggcc gaggcctgga    600
gcgaacaacc catctatgac tacctcaagc agtcctacct gctcaccgcc aggcacctgc    660
tggcctcggt ggatgccctg gagggcgtcc cccagaagag ccgggagcgg ctgcgtttct    720
cacccgcca gtacgtcagc gccatggccc cagcaactt cctggccacc aaccccgagc    780
tgctcaagct gacctggag tccggcggcc agaacctggt gcgcgactg gccctcttgg    840
ccgaggatct ggagcgcagc gccgatcagc tcaacatccg cctgaccgac gaatccgcct    900
```

-continued

```
tcgagctcgg gcgggatctg ccctgaccc cgggccgggt ggtgcagcgc accgagctct      960
atgagctcat tcagtacagc ccgactaccg agacggtggg caagacacct gtgctgatag     1020
tgccgccctt catcaacaag tactacatca tggacatgcg ccccagaac tccctggtcg      1080 cctggctggt cgcccagggc cagacggtat tcatgatctc ctggcgcaac ccgggcgtgg    1140
cccaggccca atcgatctc gacgactacg tggtggatgg cgtcatcgcc gccctggacg      1200
gcgtggaggc ggccaccggc gagcgggagg tgcacggcat cggctactgc atcgcggca     1260 ccgccctgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg gcgctcgagg cgcaaaatga ggccaagggc atcatggacg   1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat ctcggcaagg   1680
tgaagacccc tgtgctgctg tgtcggcgg tggacgatca catcgccctc tggcagggca    1740
cctggcaggg catgaagctg tttggcgggg agcagcgctt cctcctggcg gagtccggcc   1800
acatcgccgg catcatcaac ccgccggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc   1980
gggtcccgga ggaagggctg ccccccgccc cggccacta tgtcaaggtg cggctcaacc    2040
ccgtgtttgc ctgcccaaca gaggaggacg ccgcatgagc ctgacctgcc ggcctggttc   2100
aaccagtcgg cagccgacta gtggatccga gc                                  2132
```

<210> SEQ ID NO 16
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 16

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggccc tggcccacta caatgacaag ctgctggcca    360
tggccaaggc ccagacaaat cgcaccgccc aggcgctgct gcagaccaat ctggacgatc     420
tgggccaggt gctggagcag ggcagccagc aaccctggca gctgatccag gcccagatga    480
actggtggca ggatcagctc aagctgatgc agcacaccct gctcaaaagc gcaggccagc    540
cgagcgagcc ggtgatcacc ccggagcgca gcgatcgccg cttcaaggcc gaggcctgga   600
gcgaacaacc catctatgac tacctcaagc agtcctacct gctcaccgcc aggcacctgc    660
tggcctcggt ggatgccctg gagggcgtcc cccagaagag ccgggagcgg ctgcgttttct   720 tcacccgcca gtacgtcagc gccatggccc ccagcaactt cctggccacc aaccccgagc    780
tgctcaagct gaccctggag tccggcggcc agaacctggt gcgcggactg gccctcttgg    840
```

```
ccgaggatct ggagcgcagc gccgatcagc tcaacatccg cctgaccgac gaatccgcct      900
tcgagctcgg gcgggatctg gccctgaccc cgggccgggt ggtgcagcgc accgagctct      960
atgagctcat tcagtacagc ccgactaccg agacggtggg caagacacct gtgctgatag     1020
tgccgccctt catcaacaag tactacatca tggacatgcg gccccagaac tccctggtcg     1080
cctggctggt cgcccagggc cagacggtat tcatgatctc ctggcgcaac ccgggcgtgg     1140
cccaggccca aatcgatctc gacgactacg tggtggatgg cgtcatcgcc gccctggacg     1200
gcgtggaggc ggccaccggc gagcgggagg tgcacggcat cggctactgc atcggcggca     1260 ccgcccctgtc gctcgccatg ggctggctgg cggcgcggcg ccagaagcag cgggtgcgca     1320
ccgccaccct gttcactacc ctgctggact ctcccagcc cggggagctt ggcatcttca     1380
tccacgagcc catcatagcg gcgctcgagg cgcaaaatga ggccaagggc atcatggacg     1440
ggcgccagct ggcggtctcc ttcagcctgc tgcgggagaa cagcctctac tggaactact     1500
acatcgacag ctacctcaag ggtcagagcc cggtggcctt cgatctgctg cactggaaca     1560
gcgacagcac caatgtggcg ggcaagaccc acaacagcct gctgcgccgt ctctacctgg     1620
agaaccagct ggtgaagggg gagctcaaga tccgcaacac ccgcatcgat ctcggcaagg     1680
tgaagacccc tgtgctgctg gtgtcggcgg tggacgatca catcgccctc tggcagggca     1740
cctggcaggg catgaagctg tttgcgggg agcagcgctt cctcctggcg gagtccggcc     1800
acatcgccgg catcatcaac cgccggccg ccaacaagta cggcttctgg cacaacgggg     1860
ccgaggccga gagcccggag agctggctgg caggggcgac gcaccagggc ggctcctggt     1920
ggcccgagat gatgggcttt atccagaacc gtgacgaagg gtcagagccc gtccccgcgc     1980
gggtcccgga ggaagggctg gccccgccc ccggccacta tgtcaaggtg cggctcaacc     2040
ccgtgtttgc ctgcccaaca gaggaggacg ccgcatgagc ctgacctgcc ggcctggttc     2100
aaccagtcgg cagccgacta gtggatccga gc                                  2132
```

<210> SEQ ID NO 17
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 17

```
cctagggtgt acattgcgct gaaagaaggg ccaattgtgc ttctggcgtc aggcagccat       60
cggaagctgt ggtatggctg tgcaggtcgt aaatcactgc ataattcgtg tcgctcaagg      120
cgcactcccg ttctggataa tgttttttgc gccgacatca taacggttct ggcaaatatt      180
ctgaaatgag ctgttgacaa ttaatcatcg aactagttaa ctagtacgca agttcacagc      240
ggataacaat ttcacacagg aaacaattgc acgtgcagag agacaatcaa atcatgagcc      300
aaccatctta tggcccgctg ttcgaggccc tggcccacta caatgacaag ctgctggcca      360
tggccaaggc ccagacaagt cgcaccgccc aggcgctgct gcagaccaat ctggacgatc      420
tgggccaggt gctggagcag ggcagccagc aaccctggca gctgatccag gcccagatga      480
actggtggca ggatcagctc aagctgatgc agcacaccct gctcaaaagc gcaggccagc      540
cgagcgagcc ggtgatcacc cggagcgca gcgatcgccg cttcaaggcc gaggcctgga      600
gcgaacaacc catctatgac tacctcaagc agtcctacct gctcaccgcc aggcacctgc      660
tggcctcggt ggatgccctg gagggcgtcc cccagaagag ccgggagcgg ctgcgtttct      720
```

```
tcacccgcca gtacgtcagc gccatggccc ccagcaactt cctggccacc aaccccgagc      780
tgctcaagct gaccctggag tccggcggcc agaacctggt gcgcggactg gccctcttgg      840
ccgaggatct ggagcgcagc gccgatcagc tcaacatccg cctgaccgac gaatccgcct      900
tcgagctcgg gcgggatctg gccctgaccc cgggccgggt ggtgcagcgc accgagctct      960
atgagctcat tcagtacagc ccgactaccg agacggtggg caagacacct gtgctgatag     1020
tgccgccctt catcaacaag tactacatca tggacatgcg gccccagaac tccctggtcg     1080
cctggctggt cgcccagggc cagacggtat tcatgatctc ctggcgcaac ccgggcgtgg     1140
cccaggccca aatcgatctc gacgactacg tggtggatgg cgtcatcgcc gccctggacg     1200
gcgtggaggc ggccaccggc gagcgggagg tgcacggcat cggctactgc atcggcggca     1260
ccgccctgtc gctcgccatg ggctggctgg cggcgcggcg ccagaagcag cgggtgcgca     1320
ccgccaccct gttcactacc ctgctggact tctcccagcc cggggagctt ggcatcttca     1380
tccacgagcc catcatagcg gcgctcgagg cgcaaaatga ggccaagggc atcatggacg     1440
ggcgccagct ggcggtctcc ttcagcctgc tgcgggagaa cagcctctac tggaactact     1500
acatcgacag ctacctcaag ggtcagagcc cggtggcctt cgatctgctg cactggaaca     1560
gcgacagcac caatgtggcg ggcaagaccc acaacagcct gctgcgccgt ctctacctgg     1620
agaaccagct ggtgaagggg gagctcaaga tccgcaacac ccgcatcgat ctcggcaagg     1680
tgaagacccc tgtgctgctg gtgtcggcgg tggacgatca catcgccctc tggcagggca     1740
cctggcaggg catgaagctg tttggcgggg agcagcgctt cctcctggcg gagtccggcc     1800
acatcgccgg catcatcaac ccgccggccg ccaacaagta cggcttctgg cacaacgggg     1860
ccgaggccga gagcccggag agctggctgg caggggcgac gcaccagggc ggctcctggt     1920
ggcccgagat gatgggcttt atccagaacc gtgacgaagg gtcagagccc gtccccgcgc     1980
gggtcccgga ggaagggctg gcccccgccc ccggccacta tgtcaaggtg cggctcaacc     2040 ccgtgttttgc ctgcccaaca gaggaggacg ccgcatgagc ctgacctgcc ggcctggttc     2100
aaccagtcgg cagccgacta gtggatccga gc                                   2132
```

<210> SEQ ID NO 18
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 18

```
cctagggtgt acattgcgct gaaagaaggg ccaattgtgc ttctggcgtc aggcagccat       60
cggaagctgt ggtatggctg tgcaggtcgt aaatcactgc ataattcgtg tcgctcaagg      120
cgcactcccg ttctggataa tgttttttgc gccgacatca taacggttct ggcaaatatt      180
ctgaaatgag ctgttgacaa ttaatcatcg aactagttaa ctagtacgca agttcacagc      240
ggataacaat ttcacacagg aaacaattgc acgtgcagag agacaatcaa atcatgagcc      300
aaccatctta tggcccgctg ttcgaggccc tggcccacta caatgacaag ctgctggcca      360
tggccaaggc ccagacagag gggaccgccc aggcgctgct gcagaccaat ctggacgatc      420
tgggccaggt gctggagcag ggcagccagc aaccctggca gctgatccag gcccagatga      480
actggtggca ggatcagctc aagctgatgc agcacaccct gctcaaaagc gcaggccagc      540
cgagcgagcg ggtgatcacc ccggagcgca gcgatcgccg cttcaaggcc gaggcctgga      600
gcgaacaacc catctatgac tacctcaagc agtcctacct gctcaccgcc aggcaccctgc     660
```

```
tggcctcggt ggatgccctg gagggcgtcc cccagaagag ccgggagcgg ctgcgtttct    720
tcacccgcca gtacgtcagc gccatggccc ccagcaactt cctggccacc aaccccgagc    780
tgctcaagct gaccctggag tccggcggcc agaacctggt gcgcggactg cccctcttgg    840
ccgaggatct ggacgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag   1020
tgccgccctt catcaacaag tactacatca tggacatgcg gccccagaac tccctggtcg   1080
cctggctggt cgcccagggc cagacggtat tcatgatctc ctggcgcaac ccgggcgtgg   1140
cccaggccca aatcgatctc gacgactacg tggtggatgg cgtcatcgcc gccctggacg   1200
gcgtggaggc ggccaccggc gagcgggagg tgcacggcat cggctactgc atcggcggca   1260
ccgccctgtc gctcgccatg ggctggctgg cggcgcggcg ccagaagcag cgggtgcgca   1320
ccgccaccct gttcactacc ctgctggact tctcccagcc cggggagctt ggcatcttca   1380
tccacgagcc catcatagcg gcgctcgagg cgcaaaatga ggccaagggc atcatggacg   1440
ggcgccagct ggcggtctcc ttcagcctgc tgcgggagaa cagcctctac tggaactact   1500
acatcgacag ctacctcaag ggtcagagcc cggtggcctt cgatctgctg cactggaaca   1560
gcgacagcac caatgtggcg ggcaagaccc acaacagcct gctgcgccgt ctctacctgg   1620
agaaccagct ggtgaagggg gagctcaaga tccgcaacac ccgcatcgat ctcggcaagg   1680
tgaagacccc tgtgctgctg gtgtcggcg tggacgatca catcgccctc tggcagggca   1740
cctggcaggg catgaagctg tttggcgggg agcagcgctt cctcctggcg gagtccggcc   1800
acatcgccgg catcatcaac ccgccggccg ccaacaagta cggcttctgg cacaacgggg   1860
ccgaggccga gagcccggag agctggctgg caggggcgac gcaccagggc ggctcctggt   1920
ggcccgagat gatgggcttt atccagaacc gtgacgaagg gtcagagccc gtccccgcgc   1980
gggtcccgga ggaagggctg cccccgccc ccggccacta tgtcaaggtg cggctcaacc   2040
ccgtgtttgc ctgcccaaca gaggaggacg ccgcatgagc ctgacctgcc ggcctggttc   2100
aaccagtcgg cagccgacta gtggatccga gc                                 2132
```

<210> SEQ ID NO 19
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 19

```
cctagggtgt acattgcgct gaaagaaggg ccaattgtgc ttctggcgtc aggcagccat     60
cggaagctgt ggtatggctg tgcaggtcgt aaatcactgc ataattcgtg tcgctcaagg    120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ccagacagag ccgaccgccc aggcgctgct gcagaccaat ctggacgatc    420
tgggccaggt gctggagcag ggcagccagc aaccctggca gctgatccag gcccagatga    480
actggtggca ggatcagctc aagctgatgc agcacaccct gctcaaaagc gcaggccagc    540
```

| | |
|---|---|
| cgagcgagcc ggtgatcacc ccggagcgca gcgatcgccg cttcaaggcc gaggcctgga | 600 |
| gcgaacaacc catctatgac tacctcaagc agtcctacct gctcaccgcc aggcacctgc | 660 |
| tggcctcggt ggatgccctg gagggcgtcc cccagaagag ccgggagcgg ctgcgtttct | 720 |
| tcacccgcca gtacgtcagc gccatggccc cagcaacttc ctggccacc aaccccgagc | 780 |
| tgctcaagct gaccctggag tccggcggcc agaacctggt gcgcggactg gccctcttgg | 840 |
| ccgaggatct ggagcgcagc gccgatcagc tcaacatccg cctgaccgac gaatccgcct | 900 |
| tcgagctcgg gcgggatctg gccctgaccc cgggccgggt ggtgcagcgc accgagctct | 960 |
| atgagctcat tcagtacagc ccgactaccg agacggtggg caagacacct gtgctgatag | 1020 |
| tgccgccctt catcaacaag tactacatca tggacatgcg gccccagaac tccctggtcg | 1080 |
| cctggctggt cgcccagggc cagacggtat tcatgatctc ctggcgcaac ccgggcgtgg | 1140 |
| cccaggccca aatcgatctc gacgactacg tggtggatgg cgtcatcgcc gccctggacg | 1200 |
| gcgtggaggc ggccaccggc gagcgggagg tgcacggcat cggctactgc atcggcggca | 1260 |
| ccgccctgtc gctcgccatg ggctggctgg cggcgcggcg ccagaagcag cgggtgcgca | 1320 |
| ccgccaccct gttcactacc ctgctggact ctcccagcc cggggagctt ggcatcttca | 1380 |
| tccacgagcc catcatagcg gcgctcgagg cgcaaaatga ggccaaggc atcatggacg | 1440 |
| ggcgccagct ggcggtctcc ttcagcctgc tgcgggagaa cagcctctac tggaactact | 1500 |
| acatcgacag ctacctcaag ggtcagagcc cggtggcctt cgatctgctg cactggaaca | 1560 |
| gcgacagcac caatgtggcg ggcaagaccc acaacagcct gctgcgccgt ctctacctgg | 1620 |
| agaaccagct ggtgaagggg gagctcaaga tccgcaacac ccgcatcgat ctcggcaagg | 1680 |
| tgaagacccc tgtgctgctg gtgtcggcgg tggacgatca catcgccctc tggcagggca | 1740 |
| cctggcaggg catgaagctg tttgcgggg agcagcgctt cctcctggcg gagtccggcc | 1800 |
| acatcgccgg catcatcaac ccgccggccg ccaacaagta cggcttctgg cacaacgggg | 1860 |
| ccgaggccga gagcccggag agctggctgg caggggcgac gcaccagggc ggctcctggt | 1920 |
| ggcccgagat gatgggcttt atccagaacc gtgacgaagg gtcagagccc gtccccgcgc | 1980 |
| gggtcccgga ggaagggctg ccccccgccc ccggccacta tgtcaaggtg cggctcaacc | 2040 |
| ccgtgtttgc ctgcccaaca gaggaggacg ccgcatgagc ctgacctgcc ggcctggttc | 2100 |
| aaccagtcgg cagccgacta gtggatccga gc | 2132 |

<210> SEQ ID NO 20
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 20

| | |
|---|---|
| cctagggtgt acattgcgct gaaagaaggg ccaattgtgc ttctggcgtc aggcagccat | 60 |
| cggaagctgt ggtatggctg tgcaggtcgt aaatcactgc ataattcgtg tcgctcaagg | 120 |
| cgcactcccg ttctggataa tgttttttgc gccgacatca taacggttct ggcaaatatt | 180 |
| ctgaaatgag ctgttgacaa ttaatcatcg aactagttaa ctagtacgca agttcacagc | 240 |
| ggataacaat ttcacacagg aaacaattgc acgtgcagag agacaatcaa atcatgagcc | 300 |
| aaccatctta tggcccgctg ttcgaggccc tggcccacta caatgacaag ctgctggcca | 360 |
| tggccaaggc ccagacagag cgccctgccc aggcgctgct gcagaccaat ctggacgatc | 420 |
| tgggccaggt gctggagcag ggcagccagc aaccctggca gctgatccag gcccagatga | 480 |

```
actggtggca ggatcagctc aagctgatgc agcacaccct gctcaaaagc gcaggccagc    540
cgagcgagcc ggtgatcacc ccggagcgca gcgatcgccg cttcaaggcc gaggcctgga    600
gcgaacaacc catctatgac tacctcaagc agtcctacct gctcaccgcc aggcacctgc    660
tggcctcggt ggatgccctg gagggcgtcc cccagaagag ccgggagcgg ctgcgtttct    720
tcacccgcca gtacgtcagc gccatggccc cagcaactt cctggccacc aaccccgagc    780
tgctcaagct gaccctggag tccggcggcc agaacctggt gcgcggactg gccctcttgg    840
ccgaggatct ggagcgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag   1020
tgccgccctt catcaacaag tactacatca tggacatgcg gccccagaac tccctggtcg   1080
cctggctggt cgcccagggc cagacggtat tcatgatctc ctggcgcaac ccgggcgtgg   1140
cccaggccca aatcgatctc gacgactacg tggtggatgg cgtcatcgcc gccctggacg   1200
gcgtggaggc ggccaccggc gagcgggagg tgcacggcat cggctactgc atcggcggca   1260 ccgcccctgtc gctcgccatg ggctggctgg cggcgcggcg ccagaagcag cgggtgcgca   1320
ccgccaccct gttcactacc ctgctggact tctcccagcc cggggagctt ggcatcttca   1380
tccacgagcc catcatagcg gcgctcgagg cgcaaaatga ggccaagggc atcatggacg   1440
ggcgccagct ggcggtctcc ttcagcctgc tgcgggagaa cagcctctac tggaactact   1500
acatcgacag ctacctcaag ggtcagagcc cggtggcctt cgatctgctg cactggaaca   1560
gcgacagcac caatgtggcg ggcaagaccc acaacagcct gctgcgccgt ctctacctgg   1620
agaaccagct ggtgaagggg gagctcaaga tccgcaacac ccgcatcgat ctcggcaagg   1680
tgaagacccc tgtgctgctg gtgtcggcgg tggacgatca catcgccctc tggcagggca   1740
cctggcaggg catgaagctg tttggcgggg agcagcgctt cctcctggcg gagtccggcc   1800
acatcgccgg catcatcaac ccgccggccg ccaacaagta cggcttctgg cacaacgggg   1860
ccgaggccga gagcccggag agctggctgg caggggcgac gcaccagggc ggctcctggt   1920
ggcccgagat gatgggcttt atccagaacc gtgacgaagg gtcagagccc gtccccgcgc   1980
gggtcccgga ggaagggctg gcccccgccc ccggccacta tgtcaaggtg cggctcaacc   2040
ccgtgtttgc ctgcccaaca gaggaggacg ccgcatgagc ctgacctgcc ggcctggttc   2100
aaccagtcgg cagccgacta gtggatccga gc                                 2132
```

<210> SEQ ID NO 21
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 21

```
cctagggtgt acattgcgct gaaagaaggg ccaattgtgc ttctggcgtc aggcagccat     60
cggaagctgt ggtatggctg tgcaggtcgt aaatcactgc ataattcgtg tcgctcaagg    120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
```

| | |
|---|---|
| tggccaaggc ccagacagag cgcaccgcca ttgcgctgct gcagaccaat ctggacgatc | 420 |
| tgggccaggt gctggagcag ggcagccagc aaccctggca gctgatccag gcccagatga | 480 |
| actggtggca ggatcagctc aagctgatgc agcacaccct gctcaaaagc gcaggccagc | 540 |
| cgagcgagcc ggtgatcacc ccggagcgca gcgatcgccg cttcaaggcc gaggcctgga | 600 |
| gcgaacaacc catctatgac tacctcaagc agtcctacct gctcaccgcc aggcacctgc | 660 |
| tggcctcggt ggatgccctg gagggcgtcc cccagaagag ccgggagcgg ctgcgttttct | 720 |
| tcacccgcca gtacgtcagc gccatggccc ccagcaactt cctggccacc aaccccgagc | 780 |
| tgctcaagct gaccctggag tccggcggcc agaacctggt gcgcggactg gccctcttgg | 840 |
| ccgaggatct ggagcgcagc gccgatcagc tcaacatccg cctgaccgac gaatccgcct | 900 |
| tcgagctcgg gcgggatctg gccctgaccc cgggccgggt ggtgcagcgc accgagctct | 960 |
| atgagctcat tcagtacagc ccgactaccg agacggtggg caagacacct gtgctgatag | 1020 |
| tgccgccctt catcaacaag tactacatca tggacatgcg gccccagaac tccctggtcg | 1080 |
| cctgctggt cgcccagggc cagacggtat tcatgatctc ctggcgcaac ccgggcgtgg | 1140 |
| cccaggccca aatcgatctc gacgactacg tggtggatgg cgtcatcgcc gccctggacg | 1200 |
| gcgtggaggc ggccaccggc gagcgggagg tgcacggcat cggctactgc atcggcggca | 1260 |
| ccgccctgtc gctcgccatg ggctggctgg cggcgcggcg ccagaagcag cgggtgcgca | 1320 |
| ccgccaccct gttcactacc ctgctggact tctcccagcc cggggagctt ggcatcttca | 1380 |
| tccacgagcc catcatagcg gcgctcgagg cgcaaaatga ggccaagggc atcatggacg | 1440 |
| ggcgccagct ggcggtctcc ttcagcctgc tgcgggagaa cagcctctac tggaactact | 1500 |
| acatcgacag ctacctcaag ggtcagagcc cggtggcctt cgatctgctg cactggaaca | 1560 |
| gcgacagcac caatgtggcg ggcaagaccc acaacagcct gctgcgccgt ctctacctgg | 1620 |
| agaaccagct ggtgaagggg gagctcaaga tccgcaacac ccgcatcgat ctcggcaagg | 1680 |
| tgaagacccc tgtgctgctg gtgtcggcg tggacgatca catcgccctc tggcagggca | 1740 |
| cctggcaggg catgaagctg tttggcgggg agcagcgctt cctcctggcg gagtccggcc | 1800 |
| acatcgccgg catcatcaac ccgccggccg ccaacaagta cggcttctgg cacaacgggg | 1860 |
| ccgaggccga gagcccggag agctggctgg caggggcgac gcaccagggc ggctcctggt | 1920 |
| ggcccgagat gatgggcttt atccagaacc gtgacgaagg gtcagagccc gtccccgcgc | 1980 |
| gggtcccgga ggaagggctg gcccccgccc ccggccacta tgtcaaggtg cggctcaacc | 2040 |
| ccgtgtttgc ctgcccaaca gaggaggacg ccgcatgagc ctgacctgcc ggcctggttc | 2100 |
| aaccagtcgg cagccgacta gtggatccga gc | 2132 |

<210> SEQ ID NO 22
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 22

| | |
|---|---|
| cctagggtgt acattgcgct gaaagaaggg ccaattgtgc ttctggcgtc aggcagccat | 60 |
| cggaagctgt ggtatggctg tgcaggtcgt aaatcactgc ataattcgtg tcgctcaagg | 120 |
| cgcactcccg ttctggataa tgttttttgc gccgacatca taacggttct ggcaaatatt | 180 |
| ctgaaatgag ctgttgacaa ttaatcatcg aactagttaa ctagtacgca agttcacagc | 240 |
| ggataacaat ttcacacagg aaacaattgc acgtgcagag agacaatcaa atcatgagcc | 300 |

| | | |
|---|---|---|
| aaccatctta tggcccgctg ttcgaggccc tggcccacta caatgacaag ctgctggcca | 360 | |
| tggccaaggc ccagacagag cgcaccgccg cggcgctgct gcagaccaat ctggacgatc | 420 | |
| tgggccaggt gctggagcag ggcagccagc aaccctggca gctgatccag gcccagatga | 480 | |
| actggtggca ggatcagctc aagctgatgc agcacaccct gctcaaaagc gcaggccagc | 540 | |
| cgagcgagcc ggtgatcacc ccggagcgca gcgatcgccg cttcaaggcc gaggcctgga | 600 | |
| gcgaacaacc catctatgac tacctcaagc agtcctacct gctcaccgcc aggcacctgc | 660 | |
| tggcctcggt ggatgccctg gagggcgtcc cccagaagag ccgggagcgg ctgcgtttct | 720 | |
| tcacccgcca gtacgtcagc gccatggccc cagcaacttc ctggccacca accccgagc | 780 | |
| tgctcaagct gaccctggag tccggcggcc agaacctggt gcgcggactg ccctcttgg | 840 | |
| ccgaggatct ggagcgcagc gccgatcagc tcaacatccg cctgaccgac gaatccgcct | 900 | |
| tcgagctcgg gcgggatctg gccctgaccc cgggccgggt ggtgcagcgc accgagctct | 960 | |
| atgagctcat tcagtacagc ccgactaccg agacggtggg caagacacct gtgctgatag | 1020 | |
| tgccgccctt catcaacaag tactacatca tggacatgcg gccccagaac tccctggtcg | 1080 | |
| cctggctggt cgcccagggc cagacggtat tcatgatctc ctggcgcaac ccgggcgtgg | 1140 | |
| cccaggccca aatcgatctc gacgactacg tggtggatgg cgtcatcgcc gccctggacg | 1200 | |
| gcgtggaggc ggccaccggc gagcgggagg tgcacggcat cggctactgc atcgcggca | 1260 | |
| ccgccctgtc gctcgccatg ggctggctgg cggcgcggcg ccagaagcag cgggtgcgca | 1320 | |
| ccgccaccct gttcactacc ctgctggact tctcccagcc cggggagctt ggcatcttca | 1380 | |
| tccacgagcc catcatagcg gcgctcgagg cgcaaaatga ggccaagggc atcatggacg | 1440 | |
| ggcgccagct ggcggtctcc ttcagcctgc tgcgggagaa cagcctctac tggaactact | 1500 | |
| acatcgacag ctacctcaag ggtcagagcc cggtggcctt cgatctgctg cactggaaca | 1560 | |
| gcgacagcac caatgtggcg ggcaagaccc acaacagcct gctgcgccgt ctctacctgg | 1620 | |
| agaaccagct ggtgaagggg gagctcaaga tccgcaacac ccgcatcgat ctcggcaagg | 1680 | |
| tgaagacccc tgtgctgctg gtgtcggcgg tggacgatca catcgccctc tggcagggca | 1740 | |
| cctggcaggg catgaagctg tttggcgggg agcagcgctt cctcctggcg gagtccggcc | 1800 | |
| acatcgccgg catcatcaac ccgccggccg ccaacaagta cggcttctgg cacaacgggg | 1860 | |
| ccgaggccga gagcccggag agctggctgg caggggcgac gcaccaggc ggctcctggt | 1920 | |
| ggcccgagat gatgggcttt atccagaacc gtgacgaagg gtcagagccc gtccccgcgc | 1980 | |
| gggtcccgga ggaagggctg gccccccgcc ccggccacta tgtcaaggtg cggctcaacc | 2040 | |
| ccgtgtttgc ctgcccaaca gaggaggacg ccgcatgagc ctgacctgcc ggcctggttc | 2100 | |
| aaccagtcgg cagccgacta gtggatccga gc | 2132 | |

<210> SEQ ID NO 23
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 23

| | | |
|---|---|---|
| cctagggtgt acattgcgct gaaagaaggg ccaattgtgc ttctggcgtc aggcagccat | 60 | |
| cggaagctgt ggtatggctg tgcaggtcgt aaatcactgc ataattcgtg tcgctcaagg | 120 | |
| cgcactcccg ttctggataa tgttttttgc gccgacatca taacggttct ggcaaatatt | 180 | |

```
ctgaaatgag ctgttgacaa ttaatcatcg aactagttaa ctagtacgca agttcacagc        240
ggataacaat ttcacacagg aaacaattgc acgtgcagag agacaatcaa atcatgagcc        300
aaccatctta tggcccgctg ttcgaggccc tggcccacta caatgacaag ctgctggcca        360
tggccaaggc ccagacagag cgcaccgccg ttgcgctgct gcagaccaat ctggacgatc        420
tgggccaggt gctggagcag ggcagccagc aaccctggca gctgatccag gcccagatga        480
actggtggca ggatcagctc aagctgatgc agcacaccct gctcaaaagc gcaggccagc        540
cgagcgagcc ggtgatcacc ccggagcgca gcgatcgccg cttcaaggcc gaggcctgga        600
gcgaacaacc catctatgac tacctcaagc agtcctacct gctcaccgcc aggcaccctgc       660 tggcctcggt ggatgccctg agggcgtcc cccagaagag ccgggagcgg ctgcgtttct        720
tcacccgcca gtacgtcagc gccatggccc cagcaactt cctggccacc aaccccgagc        780
tgctcaagct gaccctggag tccggcggcc agaacctggt gcgcggactg gccctcttgg        840
ccgaggatct ggagcgcagc gccgatcagc tcaacatccg cctgaccgac gaatccgcct        900
tcgagctcgg gcgggatctg gccctgaccc cgggccgggt ggtgcagcgc accgagctct        960
atgagctcat tcagtacagc ccgactaccg agacggtggg caagacacct gtgctgatag       1020
tgccgccctt catcaacaag tactacatca tggacatgcg gccccagaac tccctggtcg       1080
cctggctggt cgcccagggc cagacggtat tcatgatctc ctggcgcaac ccgggcgtgg       1140
cccaggccca aatcgatctc gacgactacg tggtggatgg cgtcatcgcc gccctggacg       1200
gcgtggaggc ggccaccggc gagcgggagg tgcacggcat cggctactgc atcggcggca       1260
ccgccctgtc gctcgccatg ggctggctgg cggcgcggcg ccagaagcag cgggtgcgca       1320
ccgccaccct gttcactacc ctgctggact ctcccagcc cggggagctt ggcatcttca       1380
tccacgagcc catcatagcg gcgctcgagg cgcaaaatga ggccaagggc atcatggacg       1440
ggcgccagct ggcggtctcc ttcagcctgc tgcgggagaa cagcctctac tggaactact       1500
acatcgacag ctacctcaag ggtcagagcc cggtggcctt cgatctgctg cactggaaca       1560
gcgacagcac caatgtggcg ggcaagaccc acaacagcct gctgcgccgt ctctacctgg       1620
agaaccagct ggtgaagggg gagctcaaga tccgcaacac ccgcatcgat ctcggcaagg       1680
tgaagacccc tgtgctgctg gtgtcggcgg tggacgatca catcgccctc tggcagggca       1740
cctggcaggg catgaagctg tttggcgggg agcagcgctt cctcctggcg gagtccggcc       1800
acatcgccgg catcatcaac cgccggccg ccaacaagta cggcttctgg cacaacgggg       1860
ccgaggccga gagcccggag agctggctgg caggggcgac gcaccagggc ggctcctggt       1920
ggcccgagat gatgggcttt atccagaacc gtgacgaagg gtcagagccc gtccccgcgc       1980
gggtcccgga ggaagggctg gccccgcgcc cggccacta tgtcaaggtg cggctcaacc       2040
ccgtgtttgc ctgcccaaca gaggaggacg ccgcatgagc ctgacctgcc ggcctggttc       2100
aaccagtcgg cagccgacta gtggatccga gc                                    2132
```

<210> SEQ ID NO 24
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 24

```
cctagggtgt acattgcgct gaaagaaggg ccaattgtgc ttctggcgtc aggcagccat         60
cggaagctgt ggtatggctg tgcaggtcgt aaatcactgc ataattcgtg tcgctcaagg       120
```

```
cgcactcccg ttctggataa tgttttttgc gccgacatca taacggttct ggcaaatatt      180
ctgaaatgag ctgttgacaa ttaatcatcg aactagttaa ctagtacgca agttcacagc      240
ggataacaat ttcacacagg aaacaattgc acgtgcagag agacaatcaa atcatgagcc      300
aaccatctta tggcccgctg ttcgaggccc tggcccacta caatgacaag ctgctggcca      360
tggccaaggc ccagacagag cgcaccgccc aggcgctgct gcagaccgct ctggacgatc      420
tgggccaggt gctggagcag ggcagccagc aaccctggca gctgatccag gcccagatga      480
actggtggca ggatcagctc aagctgatgc agcacaccct gctcaaaagc gcaggccagc      540
cgagcgagcc ggtgatcacc ccggagcgca gcgatcgccg cttcaaggcc gaggcctgga      600
gcgaacaacc catctatgac tacctcaagc agtcctacct gctcaccgcc aggcacctgc      660
tggcctcggt ggatgccctg gagggcgtcc ccagaagag ccgggagcgg ctgcgttttct      720 tcacccgcca gtacgtcagc gccatggccc cagcaacttt cctggccacc aaccccgagc      780
tgctcaagct gaccctggag tccggcggcc agaacctggt gcgcggactg gccctcttgg      840
ccgaggatct ggagcgcagc gccgatcagc tcaacatccg cctgaccgac gaatccgcct      900
tcgagctcgg gcgggatctg gccctgaccc cgggccgggt ggtgcagcgc accgagctct      960
atgagctcat tcagtacagc ccgactaccg agacggtggg caagacacct gtgctgatag     1020
tgccgccctt catcaacaag tactacatca tggacatgcg gccccagaac tccctggtcg     1080
cctggctggt cgcccagggc cagacggtat tcatgatctc ctggcgcaac ccgggcgtgg     1140
cccaggccca aatcgatctc gacgactacg tggtggatgg cgtcatcgcc gccctggacg     1200
gcgtggaggc ggccaccggc gagcgggagg tgcacggcat cggctactgc atcggcggca     1260
ccgccctgtc gctcgccatg ggctggctgg cggcgcggcg ccagaagcag cgggtgcgca     1320
ccgccaccct gttcactacc ctgctggact tctcccagcc cggggagctt ggcatcttca     1380
tccacgagcc catcatagcg cgcgctcgagg cgcaaaatga ggccaagggc atcatggacg     1440
ggcgccagct ggcggtctcc ttcagcctgc tgcgggagaa cagcctctac tggaactact     1500
acatcgacag ctacctcaag ggtcagagcc cggtggcctt cgatctgctg cactggaaca     1560
gcgacagcac caatgtggcg ggcaagaccc acaacagcct gctgcgccgt ctctacctgg     1620
agaaccagct ggtgaagggg gagctcaaga tccgcaacac ccgcatcgat ctcggcaagg     1680
tgaagacccc tgtgctgctg gtgtcggcgg tggacgatca catcgccctc tggcagggca     1740
cctggcaggg catgaagctg tttggcgggg agcagcgctt cctcctggcg gagtccggcc     1800
acatcgccgg catcatcaac ccgccggccg ccaacaagta cggcttctgg cacaacgggg     1860
ccgaggccga gagcccggag agctggctgg caggggcgac gcaccagggc ggctcctggt     1920
ggcccgagat gatgggcttt atccagaacc gtgacgaagg gtcagagccc gtccccgcgc     1980
gggtcccgga ggaagggctg gccccgcc ccggccacta tgtcaaggtg cggctcaacc      2040
ccgtgtttgc ctgcccaaca gaggaggacg ccgcatgagc ctgacctgcc ggcctggttc      2100
aaccagtcgg cagccgacta gtggatccga gc                                   2132
```

<210> SEQ ID NO 25
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 25

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggccc tggcccacta caatgacaag ctgctggcca     360
tggccaaggc ccagacagag cgcaccgccc aggcgctgct gcagacctgt ctggacgatc     420
tgggccaggt gctggagcag ggcagccagc aaccctggca gctgatccag gcccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctatgac tacctcaagc agtcctacct gctcaccgcc aggcacctgc     660
tggcctcggt ggatgccctg agggcgtcc cccagaagag ccgggagcgg ctgcgtttct     720
tcacccgcca gtacgtcagc gccatggccc ccagcaactt cctggccacc aaccccgagc     780
tgctcaagct gaccctggag tccggcggcc agaacctggt gcgcggactg gccctcttgg     840
ccgaggatct ggagcgcagc gccgatcagc tcaacatccg cctgaccgac gaatccgcct     900
tcgagctcgg gcgggatctg gccctgaccc cgggccgggt ggtgcagcgc accgagctct     960
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgccctgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg gcgctcgagg cgcaaaatga ggccaagggc atcatggacg    1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tcccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg gagtccggcc    1800
acatcgccgg catcatcaac ccgccggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc    1980
gggtcccgga ggaagggctg gcccccgccc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                  2132
```

<210> SEQ ID NO 26
<211> LENGTH: 2132
<212> TYPE: DNA

<213> ORGANISM: Artificial Sequence
<220> FEATURE:
<223> OTHER INFORMATION: Gene expressing cassette

<400> SEQUENCE: 26

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggccc tggcccacta caatgacaag ctgctggcca     360
tggccaaggc ccagacagag cgcaccgccc aggcgctgct gcagacccttt ctggacgatc     420
tgggccaggt gctggagcag ggcagccagc aaccctggca gctgatccag gcccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctatgac tacctcaagc agtcctacct gctcaccgcc aggcacctgc     660
tggcctcggt ggatgccctg gagggcgtcc cccagaagag ccgggagcgg ctgcgtttct     720
tcacccgcca gtacgtcagc gccatggccc ccagcaactt cctggccacc aaccccgagc     780
tgctcaagct gaccctggag tccggcgccc agaacctggt gcgcggactg ccctcttgg     840
ccgaggatct ggagcgcagc ccgatcagc tcaacatccg cctgaccgac gaatccgcct     900
tcgagctcgg gcgggatctg gccctgaccc cgggccgggt ggtgcagcgc accgagctct     960
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgcccgtgt gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg cgcgtcgagg cgcaaaatga ggccaagggc atcatggacg    1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat tcggcaagg    1680
tgaagacccc tgtgctgctg gtgtcggcgg tggacgatca catcgccctc tggcagggca    1740
cctggcaggg catgaagctg tttgcgggg agcagcgctt cctcctggcg gagtccggcc    1800
acatcgccgg catcatcaac ccgccggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg tcagagcccc gtccccgcgc    1980
gggtcccgga ggaagggctg gccccgccc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                 2132
```

```
<210> SEQ ID NO 27
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 27
cctagggtgt acattgcgct gaaagaaggg ccaattgtgc ttctggcgtc aggcagccat     60
cggaagctgt ggtatggctg tgcaggtcgt aaatcactgc ataattcgtg tcgctcaagg    120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ccagacagag cgcaccgccc aggcgctgct gcagacccat ctggacgatc    420
tgggccaggt gctggagcag ggcagccagc aaccctggca gctgatccag gcccagatga    480
actggtggca ggatcagctc aagctgatgc agcacaccct gctcaaaagc gcaggccagc    540
cgagcgagcc ggtgatcacc ccggagcgca gcgatcgccg cttcaaggcc gaggcctgga    600
gcgaacaacc catctatgac tacctcaagc agtcctacct gctcaccgcc aggcacctgc    660
tggcctcggt ggatgccctg gagggcgtcc ccagaagag ccgggagcgg ctgcgttct    720 tcaccccgcca gtacgtcagc gccatggccc ccagcaactt cctgccacc aaccccgagc    780 tgctcaagct gaccctggag tccggcggcc agaacctggt gcgcggactg gccctcttgg    840
ccgaggatct ggagcgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag   1020
tgccgccctt catcaacaag tactacatca tggacatgcg gccccagaac tccctggtcg   1080
cctggctggt cgcccagggc cagacggtat tcatgatctc ctggcgcaac ccgggcgtgg   1140
cccaggccca aatcgatctc gacgactacg tggtggatgg cgtcatcgcc gccctggacg   1200
gcgtggaggc ggccaccggc gagcgggagg tgcacggcat cggctactgc atcggcggca   1260 ccgcccctgtc gctcgccatg ggctggctgg cggcgcggcg ccagaagcag cgggtgcgca   1320
ccgccaccct gttcactacc ctgctggact tctcccagcc cggggagctt ggcatcttca   1380
tccacgagcc catcatagcg gcgctcgagg cgcaaaatga ggccaagggc atcatggacg   1440
ggcgccagct ggcggtctcc ttcagcctgc tgcgggagaa cagcctctac tggaactact   1500
acatcgacag ctacctcaag ggtcagagcc cggtggcctt cgatctgctg cactggaaca   1560
gcgacagcac caatgtggcg ggcaagaccc acaacagcct gctgcgccgt ctctacctgg   1620
agaaccagct ggtgaagggg gagctcaaga tccgcaacac ccgcatcgat ctcggcaagg   1680
tgaagacccc tgtgctgctg gtgtcggcgg tggacgatca catcgccctc tggcagggca   1740
cctggcaggg catgaagctg tttgcgggg agcagcgctt cctcctggcg gagtccggcc   1800
acatcgccgg catcatcaac ccgccggccg ccaacaagta cggcttctgg cacaacgggg   1860
ccgaggccga gagcccggag agctggctgg caggggcgac gcaccagggc ggctcctggt   1920
ggcccgagat gatgggcttt atccagaacc gtgacgaagg gtcagagccc gtccccgcgc   1980
gggtcccgga ggaagggctg gcccccgccc ccggccacta tgtcaaggtg cggctcaacc   2040
```

```
ccgtgtttgc ctgcccaaca gaggaggacg ccgcatgagc ctgacctgcc ggcctggttc      2100
aaccagtcgg cagccgacta gtggatccga gc                                    2132

<210> SEQ ID NO 28
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 28
cctagggtgt acattgcgct gaaagaaggg ccaattgtgc ttctggcgtc aggcagccat        60
cggaagctgt ggtatggctg tgcaggtcgt aaatcactgc ataattcgtg tcgctcaagg       120
cgcactcccg ttctggataa tgttttttgc gccgacatca taacggttct ggcaaatatt       180
ctgaaatgag ctgttgacaa ttaatcatcg aactagttaa ctagtacgca agttcacagc       240
ggataacaat ttcacacagg aaacaattgc acgtgcagag agacaatcaa atcatgagcc       300
aaccatctta tggcccgctg ttcgaggccc tggcccacta caatgacaag ctgctggcca       360
tggccaaggc ccagacagag cgcaccgccc aggcgctgct gcagaccatt ctggacgatc       420
tgggccaggt gctggagcag ggcagccagc aaccctggca gctgatccag gcccagatga       480
actggtggca ggatcagctc aagctgatgc agcacaccct gctcaaaagc gcaggccagc       540
cgagcgagcc ggtgatcacc ccggagcgca gcgatcgccg cttcaaggcc gaggcctgga       600
gcgaacaacc catctatgac tacctcaagc agtcctacct gctcaccgcc aggcacctgc       660
tggcctcggt ggatgccctg agggcgtcc cccagaagag ccgggagcgg ctgcgtttct       720
tcacccgcca gtacgtcagc gccatggccc cagcaactt cctggccacc aaccccgagc       780
tgctcaagct gaccctggag tccggcggcc agaacctggt gcgcggactg gccctcttgg       840
ccgaggatct ggagcgcagc gccgatcagc tcaacatccg cctgaccgac gaatccgcct       900
tcgagctcgg gcgggatctg gccctgaccc cgggccgggt ggtgcagcgc accgagctct       960
atgagctcat tcagtacagc ccgactaccg agacggtggg caagacacct gtgctgatag      1020
tgccgccctt catcaacaag tactacatca tggacatgcg gccccagaac tccctggtcg      1080
cctggctggt cgcccagggc cagacggtat tcatgatctc ctggcgcaac ccgggcgtgg      1140
cccaggccca aatcgatctc gacgactacg tggtggatgg cgtcatcgcc gccctggacg      1200
gcgtggaggc ggccaccggc gagcgggagg tgcacggcat cggctactgc atcggcggca      1260
ccgccctgtc gctcgccatg ggctggctgg cggcgcggcg ccagaagcag cgggtgcgca      1320
ccgccaccct gttcactacc ctgctggact ctcccagcc cggggagctt ggcatcttca      1380
tccacgagcc catcatagcg gcgctcgagg cgcaaaatga ggccaagggc atcatggacg      1440
ggcgccagct ggcggtctcc ttcagcctgc tgcgggagaa cagcctctac tggaactact      1500
acatcgacag ctacctcaag ggtcagagcc cggtggcctt cgatctgctg cactggaaca      1560
gcgacagcac caatgtggcg ggcaagaccc acaacagcct gctgcgccgt ctctacctgg      1620
agaaccagct ggtgaagggg gagctcaaga tccgcaacac ccgcatcgat ctcggcaagg      1680
tgaagacccc tgtgctgctg gtgtcggcgg tggacgatca catcgccctc tggcagggca      1740
cctggcaggg catgaagctg tttggcgggg agcagcgctt cctcctggcg gagtccggcc      1800
acatcgccgg catcatcaac ccgccggccg ccaacaagta cggcttctgg cacaacgggg      1860
ccgaggccga gagcccggag agctggctgg caggggcgac gcaccagggc ggctcctggt      1920
```

```
ggcccgagat gatgggcttt atccagaacc gtgacgaagg gtcagagccc gtccccgcgc   1980
gggtcccgga ggaagggctg gccccgccc  ccggccacta tgtcaaggtg cggctcaacc   2040
ccgtgtttgc ctgcccaaca gaggaggacg ccgcatgagc ctgacctgcc ggcctggttc   2100
aaccagtcgg cagccgacta gtggatccga gc                                 2132

<210> SEQ ID NO 29
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 29
cctagggtgt acattgcgct gaaagaaggg ccaattgtgc ttctggcgtc aggcagccat     60
cggaagctgt ggtatggctg tgcaggtcgt aaatcactgc ataattcgtg tcgctcaagg    120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ccagacagag cgcaccgccc aggcgctgct gcagaccatg ctggacgatc    420
tgggccaggt gctggagcag gcagccagc  aaccctggca gctgatccag cccagatga    480 actggtggca ggatcagctc aagctgatgc agcacaccct gctcaaaagc gcaggccagc    540
cgagcgagcg ggtgatcacc ccggagcgca gcgatcgccg cttcaaggcc gaggcctgga    600
gcgaacaacc catctatgac tacctcaagc agtcctacct gctcaccgcc aggcacctgc    660
tggcctcggt ggatgccctg gagggcgtcc ccagaagag  ccgggagcgg ctgcgttttct   720 tcacccgcca gtacgtcagc gccatggccc ccagcaactt cctggccacc aaccccgagc    780
tgctcaagct gaccctggag tccggcgcc  agaacctggt gcgcggactg gccctcttgg    840
ccgaggatct ggagcgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag   1020
tgccgccctt catcaacaag tactacatca tggacatgcg gccccagaac tccctggtcg   1080
cctggctggt cgcccagggc cagacggtat tcatgatctc ctggcgcaac ccgggcgtgg   1140
cccaggccca aatcgatctc gacgactacg tggtggatgg cgtcatcgcc gccctggacg   1200
gcgtggaggc ggccaccggc gagcgggagg tgcacggcat cggctactgc atcggcggca   1260
ccgccctgtc gctcgccatg ggctggctgg cggcgcggcg ccagaagcag cgggtgcgca   1320
ccgccaccct gttcactacc ctgctggact tctcccagcc cggggagctt ggcatcttca   1380
tccacgagcc catcatagcg gcgctcgagg cgcaaaatga ggccaagggc atcatggacg   1440
ggcgccagct ggcggtctcc ttcagcctgc tgcgggagaa cagcctctac tggaactact   1500
acatcgacag ctacctcaag ggtcagagcc cggtggcctt cgatctgctg cactggaaca   1560
gcgacagcac caatgtggcg ggcaagacca caacagcct  gctgcgccgt tctctacctgg   1620 agaaccagct ggtgaagggg gagctcaaga tccgcaacac ccgcatcgat ctcggcaagg   1680 tgaagaccc  tgtgctgctg gtgtcggcgg tggacgatca catcgccctc tggcagggca   1740
cctggcaggg catgaagctg tttggcgggg agcagcgctt cctcctggcg gagtccggcc   1800
acatcgccgg catcatcaac ccgccggccg ccaacaagta cggcttctgg cacaacgggg   1860
```

```
ccgaggccga gagcccggag agctggctgg caggggcgac gcaccagggc ggctcctggt     1920
ggcccgagat gatgggcttt atccagaacc gtgacgaagg gtcagagccc gtccccgcgc     1980
gggtcccgga ggaagggctg gcccccgccc ccggccacta tgtcaaggtg cggctcaacc     2040
ccgtgtttgc ctgcccaaca gaggaggacg ccgcatgagc ctgacctgcc ggcctggttc     2100
aaccagtcgg cagccgacta gtggatccga gc                                  2132
```

<210> SEQ ID NO 30
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 30

```
cctagggtgt acattgcgct gaaagaaggg ccaattgtgc ttctggcgtc aggcagccat       60
cggaagctgt ggtatggctg tgcaggtcgt aaatcactgc ataattcgtg tcgctcaagg      120
cgcactcccg ttctggataa tgttttttgc gccgacatca taacggttct ggcaaatatt      180
ctgaaatgag ctgttgacaa ttaatcatcg aactagttaa ctagtacgca agttcacagc      240
ggataacaat ttcacacagg aaacaattgc acgtgcagag agacaatcaa atcatgagcc      300
aaccatctta tgccccgctg ttcgaggccc tggcccacta caatgacaag ctgctggcca      360
tggccaaggc ccagacagag cgcaccgccc aggcgctgct gcagacccag ctggacgatc      420
tgggccaggt gctggagcag gcagccagc aaccctggca gctgatccag gcccagatga      480
actggtggca ggatcagctc aagctgatgc agcacaccct gctcaaaagc gcaggccagc      540
cgagcgagcc ggtgatcacc ccggagcgca gcgatcgccg cttcaaggcc gaggcctgga      600
gcgaacaacc catctatgac tacctcaagc agtcctacct gctcaccgcc aggcacctgc      660
tggcctcggt ggatgccctg gagggcgtcc cccagaagag ccgggagcgg ctgcgttcct      720
tcacccgcca gtacgtcagc gccatggccc ccagcaactt cctggccacc aaccccgagc      780
tgctcaagct gacccctggag tccggcggcc agaacctggt gcgcggactg gccctcttgg      840
ccgaggatct ggagcgcagc gccgatcagc tcaacatccg cctgaccgac gaatccgcct      900
tcgagctcgg gcgggatctg gccctgaccc cgggccgggt ggtgcagcgc accgagctct      960
atgagctcat tcagtacagc ccgactaccg agacggtggg caagacacct gtgctgatag     1020 tgccgcccctt catcaacaag tactacatca tggacatgcg gccccagaac tccctggtcg     1080
cctggctggt cgcccagggc cagacggtat tcatgatctc ctggcgcaac ccgggcgtgg     1140
cccaggccca aatcgatctc gacgactacg tggtggatgg cgtcatcgcc gccctggacg     1200
gcgtggaggc ggccaccggc gagcgggagt gcacggcat cggctactgc atcggcggca     1260
ccgccctgtc gctcgccatg ggctggctgg cggcgcggcg ccagaagcag cgggtgcgca     1320
ccgccaccct gttcactacc ctgctggact tctcccagcc cggggagctt ggcatcttca     1380
tccacgagcc catcatagcg gcgctcgagg cgcaaaatga ggccaagggc atcatggacg     1440
ggcgccagct ggcggtctcc ttcagcctgc tgcgggagaa cagcctctac tggaactact     1500
acatcgacag ctacctcaag ggtcagagcc cggtggcctt cgatctgctg cactggaaca     1560
gcgacagcac caatgtggcg ggcaagaccc acaacagcct gctgcgccgt ctctacctgg     1620
agaaccagtc ggtgaagggg gagctcaaga tccgcaacac ccgcatcgat ctcggcaagg     1680
tgaagacccc tgtgctgctg gtgtcggcgg tggacgatca catcgccctc tggcagggca     1740
```

| | |
|---|---|
| cctggcaggg catgaagctg tttggcgggg agcagcgctt cctcctggcg gagtccggcc | 1800 |
| acatcgccgg catcatcaac ccgccggccg ccaacaagta cggcttctgg cacaacgggg | 1860 |
| ccgaggccga gagcccggag agctggctgg caggggcgac gcaccagggc ggctcctggt | 1920 |
| ggcccgagat gatgggcttt atccagaacc gtgacgaagg gtcagagccc gtccccgcgc | 1980 |
| gggtcccgga ggaagggctg ccccccgccc ccggccacta tgtcaaggtg cggctcaacc | 2040 |
| ccgtgtttgc ctgcccaaca gaggaggacg ccgcatgagc ctgacctgcc ggcctggttc | 2100 |
| aaccagtcgg cagccgacta gtggatccga gc | 2132 |

<210> SEQ ID NO 31
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 31

| | |
|---|---|
| cctagggtgt acattgcgct gaaagaaggg ccaattgtgc ttctggcgtc aggcagccat | 60 |
| cggaagctgt ggtatggctg tgcaggtcgt aaatcactgc ataattcgtg tcgctcaagg | 120 |
| cgcactcccg ttctggataa tgttttttgc gccgacatca taacggttct ggcaaatatt | 180 |
| ctgaaatgag ctgttgacaa ttaatcatcg aactagttaa ctagtacgca agttcacagc | 240 |
| ggataacaat ttcacacagg aaacaattgc acgtgcagag agacaatcaa atcatgagcc | 300 |
| aaccatctta tggcccgctg ttcgaggccc tgcccactca caatgacaag ctgctggcca | 360 |
| tggccaaggc ccagacagag cgcaccgccc aggcgctgct gcagacctgg ctggacgatc | 420 |
| tgggccaggt gctggagcag ggcagccagc aaccctggca gctgatccag gcccagatga | 480 |
| actggtggca ggatcagctc aagctgatgc agcacaccct gctcaaaagc gcaggccagc | 540 |
| cgagcgagcc ggtgatcacc ccggagcgca gcgatcgccg cttcaaggcc gaggcctgga | 600 |
| gcgaacaacc catctatgac tacctcaagc agtcctacct gctcaccgcc aggcacctgc | 660 |
| tggcctcggt ggatgccctg gagggcgtcc cccagaagag ccgggagcgg ctgcgtttct | 720 |
| tcacccgcca gtacgtcagc gccatggccc cagcaacttc ctggccaccc aaccccgagc | 780 |
| tgctcaagct gaccctggag tccggcggcc agaacctggt gcgcggactg gccctcttgg | 840 |
| ccgaggatct ggagcgcagc gccgatcagc tcaacatccg cctgaccgac gaatccgcct | 900 |
| tcgagctcgg gcgggatctg gccctgaccc cgggccgggt ggtgcagcgc accgagctct | 960 |
| atgagctcat tcagtacagc ccgactaccg agacggtggg caagacacct gtgctgatag | 1020 |
| tgccgcccctt catcaacaag tactacatca tggacatgcg gccccagaac tccctggtcg | 1080 |
| cctggctggt cgcccagggc cagacggtat tcatgatctc ctggcgcaac ccgggcgtgg | 1140 |
| cccaggccca aatcgatctc gacgactacg tggtggatgg cgtcatcgcc gccctggacg | 1200 |
| gcgtggaggc ggccaccggc gagcgggagt gcacggcat cggctactgc atcggcggca | 1260 |
| ccgccctgtc gctcgccatg ggctggctgg cggcgcggcg ccagaagcag cgggtgcgca | 1320 |
| ccgccaccct gttcactacc ctgctggact ctcccagcc cggggagctt ggcatcttca | 1380 |
| tccacgagcc catcatagcg gcgctcgagg cgcaaaatga ggccaagggc atcatggacg | 1440 |
| ggcgccagct ggcggtctcc ttcagcctgc tgcgggagaa cagcctctac tggaactact | 1500 |
| acatcgacag ctacctcaag ggtcagagcc cggtggcctt cgatctgctg cactggaaca | 1560 |
| gcgacagcac caatgtggcg ggcaagaccc acaacagcct gctgcgccgt ctctacctgg | 1620 |
| agaaccagct ggtgaagggg gagctcaaga tccgcaacac ccgcatcgat ctcggcaagg | 1680 |

| | |
|---|---|
| tgaagacccc tgtgctgctg gtgtcggcgg tggacgatca catcgccctc tggcagggca | 1740 |
| cctggcaggg catgaagctg tttggcgggg agcagcgctt cctcctggcg gagtccggcc | 1800 |
| acatcgccgg catcatcaac ccgccggccg ccaacaagta cggcttctgg cacaacgggg | 1860 |
| ccgaggccga gagcccggag agctggctgg caggggcgac gcaccagggc ggctcctggt | 1920 |
| ggcccgagat gatgggcttt atccagaacc gtgacgaagg gtcagagccc gtccccgcgc | 1980 |
| gggtcccgga ggaagggctg gcccccgccc ccggccacta tgtcaaggtg cggctcaacc | 2040 |
| ccgtgtttgc ctgcccaaca gaggaggacg ccgcatgagc ctgacctgcc ggcctggttc | 2100 |
| aaccagtcgg cagccgacta gtggatccga gc | 2132 |

<210> SEQ ID NO 32
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 32

| | |
|---|---|
| cctagggtgt acattgcgct gaaagaaggg ccaattgtgc ttctggcgtc aggcagccat | 60 |
| cggaagctgt ggtatggctg tgcaggtcgt aaatcactgc ataattcgtg tcgctcaagg | 120 |
| cgcactcccg ttctggataa tgttttttgc gccgacatca taacggttct ggcaaatatt | 180 |
| ctgaaatgag ctgttgacaa ttaatcatcg aactagttaa ctagtacgca agttcacagc | 240 |
| ggataacaat ttcacacagg aaacaattgc acgtgcagag agacaatcaa atcatgagcc | 300 |
| aaccatctta tggcccgctg ttcgaggccc tggcccacta caatgacaag ctgctggcca | 360 |
| tggccaaggc ccagacagag cgcaccgccc aggcgctgct gcagaccaat ctggacgatc | 420 |
| tgggccaggt gctggagcag ggcagccagc aaccctggcc gctgatccag gcccagatga | 480 |
| actggtggca ggatcagctc aagctgatgc agcacaccct gctcaaaagc gcaggccagc | 540 |
| cgagcgagcc ggtgatcacc ccggagcgca gcgatcgccg cttcaaggcc gaggcctgga | 600 |
| gcgaacaacc catctatgac tacctcaagc agtcctacct gctcaccgcc aggcacctgc | 660 |
| tggcctcggt ggatgccctg gagggcgtcc cccagaagag ccgggagcgg ctgcgtttct | 720 |
| tcacccgcca gtacgtcagc gccatggccc cagcaacctt cctggccacc aaccccgagc | 780 |
| tgctcaagct gaccctggag tccggcggcc agaacctggt gcgcggactg gccctcttgg | 840 |
| ccgaggatct ggagcgcagc gccgatcagc tcaacatccg cctgaccgac gaatccgcct | 900 |
| tcgagctcgg gcgggatctg gccctgaccc cgggccgggt ggtgcagcgc accgagctct | 960 |
| atgagctcat tcagtacagc ccgactaccg agacggtggg caagacacct gtgctgatag | 1020 |
| tgccgccctt catcaacaag tactacatca tggacatgcg gccccagaac tccctggtcg | 1080 |
| cctggctggt cgcccagggc cagacggtat tcatgatctc ctggcgcaac ccgggcgtgg | 1140 |
| cccaggccca aatcgatctc gacgactacg tggtggatgg cgtcatcgcc gccctggacg | 1200 |
| gcgtggaggc ggccaccggc gagcgggagg tgcacggcat cggctactgc atcggcggca | 1260 |
| ccgcccgtgtc gctcgccatg ggctggctgg cggcgcggcg ccagaagcag cgggtgcgca | 1320 |
| ccgccaccct gttcactacc ctgctggact tctcccagcc cggggagctt ggcatcttca | 1380 |
| tccacgagcc catcatagcg gcgctcgagg cgcaaaatga ggccaagggc atcatggacg | 1440 |
| ggcgccagct ggcggtctcc ttcagcctgc tgcgggagaa cagcctctac tggaactact | 1500 |
| acatcgacag ctacctcaag ggtcagagcc cggtggcctt cgatctgctg cactggaaca | 1560 |

| | |
|---|---|
| gcgacagcac caatgtggcg ggcaagaccc acaacagcct gctgcgccgt ctctacctgg | 1620 |
| agaaccagct ggtgaagggg gagctcaaga tccgcaacac ccgcatcgat ctcggcaagg | 1680 |
| tgaagacccc tgtgctgctg gtgtcggcgg tggacgatca catcgccctc tggcagggca | 1740 |
| cctggcaggg catgaagctg tttggcgggg agcagcgctt cctcctggcg gagtccggcc | 1800 |
| acatcgccgg catcatcaac ccgccggccg ccaacaagta cggcttctgg cacaacgggg | 1860 |
| ccgaggccga gagcccggag agctggctgg caggggcgac gcaccagggc ggctcctggt | 1920 |
| ggcccgagat gatgggcttt atccagaacc gtgacgaagg gtcagagccc gtccccgcgc | 1980 |
| gggtcccgga ggaagggctg gccccgccc ccggccacta tgtcaaggtg cggctcaacc | 2040 |
| ccgtgtttgc ctgcccaaca gaggaggacg ccgcatgagc ctgacctgcc ggcctggttc | 2100 |
| aaccagtcgg cagccgacta gtggatccga gc | 2132 |

<210> SEQ ID NO 33
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 33

| | |
|---|---|
| cctagggtgt acattgcgct gaaagaaggg ccaattgtgc ttctggcgtc aggcagccat | 60 |
| cggaagctgt ggtatggctg tgcaggtcgt aaatcactgc ataattcgtg tcgctcaagg | 120 |
| cgcactcccg ttctggataa tgttttttgc gccgacatca taacggttct ggcaaatatt | 180 |
| ctgaaatgag ctgttgacaa ttaatcatcg aactagttaa ctagtacgca agttcacagc | 240 |
| ggataacaat ttcacacagg aaacaattgc acgtgcagag agacaatcaa atcatgagcc | 300 |
| aaccatctta tggcccgctg ttcgaggccc tggcccacta caatgacaag ctgctggcca | 360 |
| tggccaaggc ccagacagag cgcaccgccc aggcgctgct gcagaccaat ctggacgatc | 420 |
| tgggccaggt gctggagcag ggcagccagc aaccctggca gctgatccag gcccagatga | 480 |
| actggtggca ggatcagctc aagctgatgc agcacaccct gctcaaaagc gcaggccagc | 540 |
| cgagcgagcc ggtgatcacc ccggagcgca gcgatcgccg cttcaaggcc gaggcctgga | 600 |
| gcgaacaagc tatctatgac tacctcaagc agtcctacct gctcaccgcc aggcacctgc | 660 |
| tggcctcggt ggatgccctg gagggcgtcc cccagaagag ccgggagcgg ctgcgttct | 720 |
| tcacccgcca gtacgtcagc gccatggccc ccagcaactt cctggccacc aaccccgagc | 780 |
| tgctcaagct gaccctggag tccggcgcc agaacctggt gcgcggactg gccctcttgg | 840 |
| ccgaggatct ggagcgcagc gccgatcagc tcaacatccg cctgaccgac gaatccgcct | 900 |
| tcgagctcgg gcgggatctg gccctgaccc cgggccgggt ggtgcagcgc accgagctct | 960 |
| atgagctcat tcagtacagc ccgactaccg agacggtggg caagacacct gtgctgatag | 1020 |
| tgccgccctt catcaacaag tactacatca tggacatgcg gccccagaac tccctggtcg | 1080 |
| cctggctggt cgcccagggc cagacggtat tcatgatctc ctggcgcaac ccgggcgtgg | 1140 |
| cccaggccca aatcgatctc gacgactacg tggtggatgg cgtcatcgcc gccctggacg | 1200 |
| gcgtggaggc ggccaccggc gagcgggagt gcacggcat cggctactgc atcgcggca | 1260 |
| ccgccctgtc gctcgccatg ggctggctgg cggcgcggcg ccagaagcag cgggtgcgca | 1320 |
| ccgccaccct gttcactacc ctgctggact ctcccagcc cggggagctt ggcatcttca | 1380 |
| tccacgagcc catcatagcg gcgctcgagg cgcaaaatga ggccaagggc atcatggacg | 1440 |
| ggcgccagct ggcggtctcc ttcagcctgc tgcgggagaa cagcctctac tggaactact | 1500 |

```
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg gagtccggcc    1800
acatcgccgg catcatcaac ccgcggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc    1980
gggtcccgga ggaagggctg gcccccgccc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                  2132
```

<210> SEQ ID NO 34
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 34

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggcc tggcccacta caatgacaag ctgctggcca     360
tggccaaggc ccagacagag cgcaccgccc aggcgctgct gcagaccaat ctggacgatc     420
tgggccaggt gctggagcag ggcagccagc aaccctggca gctgatccag gcccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctatgac tacctcaagc agtcctacct gctcaccgcc aggcacctgc     660
tggcctcggt ggatgcccag gagggcgtcc cccagaagag ccgggagcgg ctgcgtttct     720
tcacccgcca gtacgtcagc gccatggccc cagcaacttc cctggccacc aaccccgagc     780
tgctcaagct gaccctggag tccggcggcc agaacctggt gcgcggactg gccctcttgg     840
ccgaggatct ggagcgcagc gccgatcagc tcaacatccg cctgaccgac gaatccgcct     900
tcgagctcgg gcgggatctg gccctgaccc cgggccgggt ggtgcagcgc accgagctct     960
atgagctcat tcagtacagc ccgactaccg agacggtggg caagcacct gtgctgatag    1020 tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgccctgtc gctcgccatg ggctggctgg cggcgcggcg ccagaagcag cgggtgcgca    1320
ccgccaccct gttcactacc ctgctggact tctcccagcc cggggagctt ggcatcttca    1380
```

| | |
|---|---:|
| tccacgagcc catcatagcg gcgctcgagg cgcaaaatga ggccaagggc atcatggacg | 1440 |
| ggcgccagct ggcggtctcc ttcagcctgc tgcgggagaa cagcctctac tggaactact | 1500 |
| acatcgacag ctacctcaag ggtcagagcc cggtggcctt cgatctgctg cactggaaca | 1560 |
| gcgacagcac caatgtggcg ggcaagaccc acaacagcct gctgcgccgt ctctacctgg | 1620 |
| agaaccagct ggtgaagggg gagctcaaga tccgcaacac ccgcatcgat ctcggcaagg | 1680 |
| tgaagacccc tgtgctgctg gtgtcggcgg tggacgatca catcgccctc tggcagggca | 1740 |
| cctggcaggg catgaagctg tttggcgggg agcagcgctt cctcctggcg gagtccggcc | 1800 |
| acatcgccgg catcatcaac ccgccggccg ccaacaagta cggcttctgg cacaacgggg | 1860 |
| ccgaggccga gagcccggag agctggctgg caggggcgac gcaccagggc ggctcctggt | 1920 |
| ggcccgagat gatgggcttt atccagaacc gtgacgaagg gtcagagccc gtccccgcgc | 1980 |
| gggtcccgga ggaagggctg gccccccgccc ccggccacta tgtcaaggtg cggctcaacc | 2040 |
| ccgtgtttgc ctgcccaaca gaggaggacg ccgcatgagc ctgacctgcc ggcctggttc | 2100 |
| aaccagtcgg cagccgacta gtggatccga gc | 2132 |

<210> SEQ ID NO 35
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 35

| | |
|---|---:|
| cctagggtgt acattgcgct gaaagaaggg ccaattgtgc ttctggcgtc aggcagccat | 60 |
| cggaagctgt ggtatggctg tgcaggtcgt aaatcactgc ataattcgtg tcgctcaagg | 120 |
| cgcactcccg ttctggataa tgttttttgc gccgacatca taacggttct ggcaaatatt | 180 |
| ctgaaatgag ctgttgacaa ttaatcatcg aactagttaa ctagtacgca agttcacagc | 240 |
| ggataacaat ttcacacagg aaacaattgc acgtgcagag agacaatcaa atcatgagcc | 300 |
| aaccatctta tggcccgctg ttcgaggccc tggcccacta caatgacaag ctgctggcca | 360 |
| tggccaaggc ccagacagag cgcaccgccc aggcgctgct gcagaccaat ctggacgatc | 420 |
| tgggccaggt gctggagcag ggcagccagc aaccctggca gctgatccag gcccagatga | 480 |
| actggtggca ggatcagctc aagctgatgc agcacaccct gctcaaaagc gcaggccagc | 540 |
| cgagcgagcc ggtgatcacc ccggagcgca gcgatcgccg cttcaaggcc gaggcctgga | 600 |
| gcgaacaacc catctatgac tacctcaagc agtcctacct gctcaccgcc aggcacctgc | 660 |
| tggcctcggt ggatgccctg gagggcgtcc cccagaagag ccgggagcgg ctgcgttttct | 720 |
| tcctgcgcca gtacgtcagc gccatggccc cagcaacctt cctggccacc aaccccgagc | 780 |
| tgctcaagct gaccctggag tccggcggcc agaacctggt gcgcggactg gccctcttgg | 840 |
| ccgaggatct ggagcgcagc gccgatcagc tcaacatccg cctgaccgac gaatccgcct | 900 |
| tcgagctcgg gcgggatctg gccctgaccc cgggccgggt ggtgcagcgc accgagctct | 960 |
| atgagctcat tcagtacagc ccgactaccg agacggtggg caagacacct gtgctgatag | 1020 |
| tgccgccctt catcaacaag tactacatca tggacatgcg gccccagaac tccctggtcg | 1080 |
| cctggctggt cgcccagggc cagacggtat tcatgatctc ctggcgcaac ccgggcgtgg | 1140 |
| cccaggccca aatcgatctc gacgactacg tggtggatgg cgtcatcgcc gccctggacg | 1200 |
| gcgtggagc ggccaccggc gagcgggagg tgcacggcat cggctactgc atcgcggca | 1260 |
| ccgccctgtc gctcgccatg ggctggctgg cggcgcggcg ccagaagcag cgggtgcgca | 1320 |

| | |
|---|---|
| ccgccaccct gttcactacc ctgctggact tctcccagcc cggggagctt ggcatcttca | 1380 |
| tccacgagcc catcatagcg gcgctcgagg cgcaaaatga ggccaagggc atcatggacg | 1440 |
| ggcgccagct ggcggtctcc ttcagcctgc tgcgggagaa cagcctctac tggaactact | 1500 |
| acatcgacag ctacctcaag ggtcagagcc cggtggcctt cgatctgctg cactggaaca | 1560 |
| gcgacagcac caatgtggcg ggcaagaccc acaacagcct gctgcgccgt ctctacctgg | 1620 |
| agaaccagct ggtgaagggg gagctcaaga tccgcaacac ccgcatcgat ctcggcaagg | 1680 |
| tgaagacccc tgtgctgctg gtgtcggcgg tggacgatca catcgccctc tggcagggca | 1740 |
| cctggcaggg catgaagctg tttgcggggg agcagcgctt cctcctggcg gagtccggcc | 1800 |
| acatcgccgg catcatcaac ccgccggccg ccaacaagta cggcttctgg cacaacgggg | 1860 |
| ccgaggccga gagcccggag agctggctgg caggggcgac gcaccagggc ggctcctggt | 1920 |
| ggcccgagat gatgggcttt atccagaacc gtgacgaagg gtcagagccc gtccccgcgc | 1980 |
| gggtcccgga ggaagggctg gccccgcccc cggccacta tgtcaaggtg cggctcaacc | 2040 |
| ccgtgtttgc ctgcccaaca gaggaggacg ccgcatgagc ctgacctgcc ggcctggttc | 2100 |
| aaccagtcgg cagccgacta gtggatccga gc | 2132 |

<210> SEQ ID NO 36
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 36

| | |
|---|---|
| cctagggtgt acattgcgct gaaagaaggg ccaattgtgc ttctggcgtc aggcagccat | 60 |
| cggaagctgt ggtatggctg tgcaggtcgt aaatcactgc ataattcgtg tcgctcaagg | 120 |
| cgcactcccg ttctggataa tgttttttgc gccgacatca taacggttct ggcaaatatt | 180 |
| ctgaaatgag ctgttgacaa ttaatcatcg aactagttaa ctagtacgca agttcacagc | 240 |
| ggataacaat ttcacacagg aaacaattgc acgtgcagag agacaatcaa atcatgagcc | 300 |
| aaccatctta tggcccgctg ttcgaggccc tggcccacta caatgacaag ctgctggcca | 360 |
| tggccaaggc ccagacagag cgcaccgccc aggcgctgct gcagaccaat ctggacgatc | 420 |
| tgggccaggt gctggagcag ggcagccagc aaccctggca gctgatccag gcccagatga | 480 |
| actggtggca ggatcagctc aagctgatgc agcacaccct gctcaaaagc gcaggccagc | 540 |
| cgagcgagcc ggtgatcacc ccggagcgca gcgatcgccg cttcaaggcc gaggcctgga | 600 |
| gcgaacaacc catctatgac tacctcaagc agtcctacct gctcaccgcc aggcacctgc | 660 |
| tggcctcggt ggatgccctg gagggcgtcc ccagaagag ccgggagcgg ctgcgtttct | 720 |
| tcaccccgcc gtacgtcagc gccatggccc ccagcaactt cctggccacc aaccccgagc | 780 |
| tgctcgtgct gacctggag tccggcgcc agaacctggt gcgcggactg gccctcttgg | 840 |
| ccgaggatct ggagcgcagc gccgatcagc tcaacatccg cctgaccgac gaatccgcct | 900 |
| tcgagctcgg gcgggatctg gccctgaccc cgggccgggt ggtgcagcgc accgagctct | 960 |
| atgagctcat tcagtacagc ccgactaccg agacggtggg caagacacct gtgctgatag | 1020 |
| tgccgccctt catcaacaag tactacatca tggacatgcg gccccagaac tccctggtcg | 1080 |
| cctggctggt cgcccagggc cagacggtat tcatgatctc ctggcgcaac ccgggcgtgg | 1140 |
| cccaggccca aatcgatctc gacgactacg tggtggatgg cgtcatcgcc gccctggacg | 1200 |

```
gcgtggaggc ggccaccggc gagcgggagg tgcacggcat cggctactgc atcggcggca    1260
ccgcccctgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg gcgctcgagg cgcaaaatga ggccaagggc atcatggacg    1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg agtccggcc    1800
acatcgccgg catcatcaac ccgccggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc    1980
gggtcccgga ggaagggctg gccccgcc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                  2132
```

<210> SEQ ID NO 37
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 37

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggccc tggcccacta caatgacaag ctgctggcca     360
tggccaaggc ccagacagag cgcaccgccc aggcgctgct gcagaccaat ctggacgatc     420
tgggccaggt gctggagcag ggcagccagc aaccctggca gctgatccag gcccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctatgac tacctcaagc agtcctacct gctcaccgcc aggcacctgc     660
tggcctcggt ggatgccctg gagggcgtcc cccagaagag ccgggagcgg ctgcgtttct     720
tcacccgcca gtacgtcagc gccatggccc ccagcaactt cctggccacc aaccccgagc     780
tgctcaagct gaccctggag cagggcggcc agaacctggt gcgcggactg gccctcttgg     840
ccgaggatct ggagcgcagc gccgatcagc tcaacatccg cctgaccgac gaatccgcct     900
tcgagctcgg gcgggatctg gccctgaccc cgggccgggt ggtgcagcgc accgagctct     960
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
```

```
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgccctgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg gcgctcgagg cgcaaaatga ggccaagggc atcatggacg    1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat ctcggcaagg    1680
tgaagacccc tgtgctgctg gtgtcggcg tggacgatca catcgccctc tggcagggca    1740
cctggcaggg catgaagctg tttggcgggg agcagcgctt cctcctggcg gagtccggcc    1800
acatcgccgg catcatcaac ccgccggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc    1980
gggtcccgga ggaagggctg gccccgccc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                 2132
```

<210> SEQ ID NO 38
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 38

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggccc tggcccacta caatgacaag ctgctggcca     360
tggccaaggc ccagacagag cgcaccgccc aggcgctgct gcagaccaat ctggacgatc     420
tgggccaggt gctggagcag ggcagccagc aaccctggca gctgatccag gcccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctatgac tacctcaagc agtcctacct gctcaccgcc aggcacctgc     660
tggcctcggt ggatgccctg gagggcgtcc cccagaagag ccgggagcgg ctgcgtttct     720
tcacccgcca gtacgtcagc gccatggccc cagcaacctt cctggccacc aaccccgagc     780
tgctcaagct gaccctggag tccggcgcc agaacctgtg gcgcggactg gcctcttgg     840 ccgaggatct ggagcgcagc gccgatcagc tcaacatccg cctgaccgac gaatccgcct     900
tcgagctcgg gcgggatctg gccctgaccc cgggccgggt ggtgcagcgc accgagctct     960
atgagctcat tcagtacagc ccgactaccg agacggtggg caagacacct gtgctgatag    1020
```

```
tgccgcccttt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgccctgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg gcgctcgagg cgcaaaatga ggccaagggc atcatggacg    1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg gagtccggcc    1800
acatcgccgg catcatcaac ccgccggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc    1980
gggtcccgga ggaagggctg gcccccgccc cggccactg tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                  2132
```

<210> SEQ ID NO 39
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 39

```
cctagggtgt acattgcgct gaaagaaggg ccaattgtgc ttctggcgtc aggcagccat     60
cggaagctgt ggtatggctg tgcaggtcgt aaatcactgc ataattcgtg tcgctcaagg    120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ccagacagag cgcaccgccc aggcgctgct gcagaccaat ctggacgatc    420
tgggccaggt gctggagcag ggcagccagc aaccctggca gctgatccag gcccagatga    480
actggtggca ggatcagctc aagctgatgc agcacaccct gctcaaaagc gcaggccagc    540
cgagcgagcc ggtgatcacc ccggagcgca gcgatcgccg cttcaaggcc gaggcctgga    600
gcgaacaacc catctatgac tacctcaagc agtcctacct gctcaccgcc aggcacctgc    660 tggcctcgt ggatgccctg gagggcgtcc cccagaagag ccgggagcgg ctgcgtttct    720
tcacccgcca gtacgtcagc gccatggccc ccagcaactt cctgccacc aaccccgagc    780 tgctcaagct gaccctggag tccggcggcc agaacctggt gcgcggacag gccctcttgg    840
ccgaggatct ggagcgcagc gccgatcagc tcaacatccg cctgaccgac gaatccgcct    900
tcgagctcgg gcgggatctg gccctgaccc cgggccgggt ggtgcagcgc accgagctct    960
```

```
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260 ccgcccctgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg gcgctcgagg cgcaaaatga ggccaagggc atcatggacg    1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg gagtccggcc    1800
acatcgccgg catcatcaac ccgccggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc    1980
gggtcccgga ggaagggctg gcccccgccc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                  2132
```

<210> SEQ ID NO 40
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 40

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggccc tggcccacta caatgacaag ctgctggcca     360
tggccaaggc ccagacagag cgcaccgccc aggcgctgct gcagaccaat ctggacgatc     420
tgggccaggt gctggagcag ggcagccagc aaccctggca gctgatccag gcccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctctatgac tacctcaagc agtcctacct gctcaccgcc aggcacctgc     660
tggcctcggt ggatgccctg gagggcgtcc cccagaagag ccgggagcgg ctgcgtttct     720
tcacccgcca gtacgtcagc gccatggccc cagcaacttt cctggccacc aaccccgagc     780
tgctcaagct gaccctggag tccggcggcc agaacctggt gcgcggacgt gccctcttgg     840
```

```
ccgaggatct ggagcgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag   1020
tgccgccctt catcaacaag tactacatca tggacatgcg gccccagaac tccctggtcg   1080
cctggctggt cgcccagggc cagacggtat tcatgatctc ctggcgcaac ccgggcgtgg   1140
cccaggccca aatcgatctc gacgactacg tggtggatgg cgtcatcgcc gccctggacg   1200
gcgtggaggc ggccaccggc gagcgggagg tgcacggcat cggctactgc atcggcggca   1260
ccgccctgtc gctcgccatg ggctggctgg cggcgcggcg ccagaagcag cgggtgcgca   1320
ccgccaccct gttcactacc ctgctggact tctcccagcc cggggagctt ggcatcttca   1380
tccacgagcc catcatagcg cgctcgagg cgcaaaatga ggccaagggc atcatggacg   1440
ggcgccagct ggcggtctcc ttcagcctgc tgcgggagaa cagcctctac tggaactact   1500
acatcgacag ctacctcaag ggtcagagcc cggtggcctt cgatctgctg cactggaaca   1560
gcgacagcac caatgtggcg ggcaagaccc acaacagcc gctgcgccgt ctctacctgg   1620
agaaccagct ggtgaagggg gagctcaaga tccgcaacac ccgcatcgat ctcggcaagg   1680
tgaagacccc tgtgctgctg gtgtcggcgg tggacgatca catcgccctc tggcagggca   1740
cctggcaggg catgaagctg tttggcgggg agcagcgctt cctcctggcg gagtccggcc   1800
acatcgccgg catcatcaac ccgccggccg ccaacaagta cggcttctgg cacaacgggg   1860
ccgaggccga gagcccggag agctggctgg caggggcgac gcaccagggc ggctcctggt   1920
ggcccgagat gatgggcttt atccagaacc gtgacgaagg gtcagagccc gtccccgcgc   1980
gggtcccgga ggaagggctg gccccccgccc ccggccacta tgtcaaggtg cggctcaacc   2040
ccgtgtttgc ctgcccaaca gaggaggacg ccgcatgagc ctgacctgcc ggcctggttc   2100
aaccagtcgg cagccgacta gtggatccga gc                                 2132
```

<210> SEQ ID NO 41
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 41

```
cctagggtgt acattgcgct gaaagaaggg ccaattgtgc ttctggcgtc aggcagccat     60
cggaagctgt ggtatggctg tgcaggtcgt aaatcactgc ataattcgtg tcgctcaagg    120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ccagacagag cgcaccgccc aggcgctgct gcagaccaat ctggacgatc    420
tgggccaggt gctggagcag gcagccagc aaccctggca gctgatccag gcccagatga    480
actggtggca ggatcagctc aagctgatgc agcacaccct gctcaaaagc gcaggccagc    540
cgagcgagcc ggtgatcacc ccggagcgca gcgatcgccg cttcaaggcc gaggcctgga    600
gcgaacaacc catctatgac tacctcaagc agtcctacct gctcaccgcc aggcacctgc    660
tggcctcggt ggatgccctg gagggcgtcc cccagaagag ccgggagcgg ctgcgttct    720 tcacccgcca gtacgtcagc gccatggccc ccagcaactt cctggccacc aaccccgagc    780
```

```
tgctcaagct gaccctggag tccggcggcc agaacctggt gcgcggactg ggtctcttgg    840
ccgaggatct ggagcgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag   1020
tgccgccctt catcaacaag tactacatca tggacatgcg gccccagaac tccctggtcg   1080
cctggctggt cgcccagggc cagacggtat tcatgatctc ctggcgcaac ccgggcgtgg   1140
cccaggccca aatcgatctc gacgactacg tggtggatgg cgtcatcgcc gccctggacg   1200
gcgtggaggc ggccaccggc gagcgggagg tgcacggcat cggctactgc atcggcggca   1260
ccgccctgtc gctcgccatg ggctggctgg cggcgcggcg ccagaagcag cgggtgcgca   1320
ccgccaccct gttcactacc ctgctggact tctcccagcc cggggagctt ggcatcttca   1380
tccacgagcc catcatagcg gcgctcgagg cgcaaaatga ggccaagggc atcatggacg   1440
ggcgccagct ggcggtctcc ttcagcctgc tgcgggagaa cagcctctac tggaactact   1500
acatcgacag ctacctcaag ggtcagagcc cggtggcctt cgatctgctg cactggaaca   1560
gcgacagcac caatgtggcg ggcaagaccc acaacagcct gctgcgccgt ctctacctgg   1620
agaaccagct ggtgaagggg gagctcaaga tccgcaacac ccgcatcgat ctcggcaagg   1680
tgaagacccc tgtgctgctg gtgtcggcgg tggacgatca catcgccctc tggcagggca   1740
cctggcaggg catgaagctg tttggcgggg agcagcgctt cctcctggcg gagtccggcc   1800
acatcgccgg catcatcaac ccgccggccg ccaacaagta cggcttctgg cacaacgggg   1860
ccgaggccga gagcccggag agctggctgg caggggcgac gcaccagggc ggctcctggt   1920
ggcccgagat gatgggcttt atccagaacc gtgacgaagg gtcagagccc gtccccgcgc   1980
gggtcccgga ggaagggctg gcccccgccc ccggccacta tgtcaaggtg cggctcaacc   2040
ccgtgtttgc ctgcccaaca gaggaggacg ccgcatgagc ctgacctgcc ggcctggttc   2100
aaccagtcgg cagccgacta gtggatccga gc                                 2132
```

<210> SEQ ID NO 42
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 42

```
cctagggtgt acattgcgct gaaagaaggg ccaattgtgc ttctggcgtc aggcagccat     60
cggaagctgt ggtatggctg tgcaggtcgt aaatcactgc ataattcgtg tcgctcaagg    120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ccagacagag cgcaccgccc aggcgctgct gcagaccaat ctggacgatc    420
tgggccaggt gctggagcag ggcagccagc aaccctggca gctgatccag gcccagatga    480
actggtggca ggatcagctc aagctgatgc agcacaccct gctcaaaagc gcaggccagc    540
cgagcgagcc ggtgatcacc ccggagcgca gcgatcgccg cttcaaggcc gaggcctgga    600
gcgaacaacc catctatgac tacctcaagc agtcctacct gctcaccgcc aggcacctgc    660
```

```
tggcctcggt ggatgccctg gagggcgtcc cccagaagag ccgggagcgg ctgcgtttct      720
tcacccgcca gtacgtcagc gccatggccc cagcaactt  cctggccacc aaccccgagc      780
tgctcaagct gaccctggag tccggcggcc agaacctggt gcgcggactg aagctcttgg      840
ccgaggatct ggagcgcagc gccgatcagc tcaacatccg cctgaccgac gaatccgcct      900
tcgagctcgg gcgggatctg gccctgaccc cgggccgggt ggtgcagcgc accgagctct      960
atgagctcat tcagtacagc ccgactaccg agacggtggg caagacacct gtgctgatag     1020
tgccgccctt catcaacaag tactacatca tggacatgcg gccccagaac tccctggtcg     1080
cctggctggt cgcccagggc cagacggtat tcatgatctc ctggcgcaac ccgggcgtgg     1140
cccaggccca aatcgatctc gacgactacg tggtggatgg cgtcatcgcc gccctggacg     1200
gcgtggaggc ggccaccggc gagcgggagg tgcacggcat cggctactgc atcggcggca     1260
ccgccctgtc gctcgccatg ggctggctgg cggcgcggcg ccagaagcag cgggtgcgca     1320
ccgccaccct gttcactacc ctgctggact ctcccagcc  cggggagctt ggcatcttca     1380
tccacgagcc catcatagcg cgctcgagg  cgcaaaatga ggccaagggc atcatggacg     1440
ggcgccagct ggcggtctcc ttcagcctgc tgcgggagaa cagcctctac tggaactact     1500
acatcgacag ctacctcaag ggtcagagcc cggtggcctt cgatctgctg cactggaaca     1560
gcgacagcac caatgtggcg ggcaagaccc acaacagcct gctgcgccgt ctctacctgg     1620
agaaccagct ggtgaagggg gagctcaaga tccgcaacac ccgcatcgat ctcggcaagg     1680
tgaagacccc tgtgctgctg gtgtcggcgg tggacgatca catcgccctc tggcagggca     1740
cctggcaggg catgaagctg tttgcgggg  agcagcgctt cctcctggcg gagtccggcc     1800
acatcgccgg catcatcaac ccgccggccg ccaacaagta cggcttctgg cacaacgggg     1860
ccgaggccga gagcccggag agctggctgg caggggcgac gcaccagggc ggctcctggt     1920
ggcccgagat gatgggcttt atccagaacc gtgacgaagg gtcagagccc gtccccgcgc     1980
gggtcccgga ggaagggctg gccccgccc  cggccacta  tgtcaaggtg cggctcaacc     2040
ccgtgtttgc ctgcccaaca gaggaggacg ccgcatgagc ctgacctgcc ggcctggttc     2100
aaccagtcgg cagccgacta gtggatccga gc                                   2132
```

<210> SEQ ID NO 43
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 43

```
cctagggtgt acattgcgct gaaagaaggg ccaattgtgc ttctggcgtc aggcagccat       60
cggaagctgt ggtatggctg tgcaggtcgt aaatcactgc ataattcgtg tcgctcaagg      120
cgcactcccg ttctggataa tgttttttgc gccgacatca taacggttct ggcaaatatt      180
ctgaaatgag ctgttgacaa ttaatcatcg aactagttaa ctagtacgca agttcacagc      240
ggataacaat ttcacacagg aaacaattgc acgtgcagag agacaatcaa atcatgagcc      300
aaccatctta tggcccgctg ttcgaggccc tgcccactac aatgacaag  ctgctggcca      360 tggccaaggc ccagacagag cgcaccgccc aggcgctgct gcagaccaat ctggacgatc      420
tgggccaggt gctggagcag ggcagccagc aaccctggca gctgatccag gcccagatga      480
actggtggca ggatcagctc aagctgatgc agcacaccct gctcaaaagc gcaggccagc      540
cgagcgagcc ggtgatcacc ccggagcgca gcgatcgccg cttcaaggcc gaggcctgga      600
```

```
gcgaacaacc catctatgac tacctcaagc agtcctacct gctcaccgcc aggcacctgc      660
tggcctcggt ggatgccctg gagggcgtcc cccagaagag ccgggagcgg ctgcgtttct      720
tcacccgcca gtacgtcagc gccatggccc ccagcaactt cctggccacc aaccccgagc      780
tgctcaagct gaccctggag tccggcggcc agaacctggt gcgcggactg aggctcttgg      840
ccgaggatct ggagcgcagc gccgatcagc tcaacatccg cctgaccgac gaatccgcct      900
tcgagctcgg gcgggatctg gccctgaccc cggggccgggt ggtgcagcgc accgagctct    960
atgagctcat tcagtacagc ccgactaccg agacggtggg caagacacct gtgctgatag      1020
tgccgccctt catcaacaag tactacatca tggacatgcg gccccagaac tccctggtcg      1080
cctggctggt cgcccagggc cagacggtat tcatgatctc ctggcgcaac ccgggcgtgg      1140
cccaggccca aatcgatctc gacgactacg tggtggatgg cgtcatcgcc gccctggacg      1200
gcgtggaggc ggccaccggc gagcgggagg tgcacggcat cggctactgc atcggcggca      1260 ccgcccctgtc gctcgccatg ggctggctgg cggcgcggcg ccagaagcag cgggtgcgca    1320
ccgccaccct gttcactacc ctgctggact tctcccagcc cggggagctt ggcatcttca      1380
tccacgagcc catcatagcg gcgctcgagg cgcaaaatga ggccaagggc atcatggacg      1440
ggcgccagct ggcggtctcc ttcagcctgc tgcgggagaa cagcctctac tggaactact      1500
acatcgacag ctacctcaag ggtcagagcc cggtggcctt cgatctgctg cactggaaca      1560
gcgacagcac caatgtggcg ggcaagaccc acaacagcct gctgcgccgt ctctacctgg      1620
agaaccagct ggtgaagggg gagctcaaga tccgcaacac ccgcatcgat ctcggcaagg      1680
tgaagacccc tgtgctgctg gtgtcggcgg tggacgatca catcgccctc tggcagggca      1740
cctggcaggg catgaagctg tttggcgggg agcagcgctt cctcctggcg gagtccggcc      1800
acatcgccgg catcatcaac ccgccggccg ccaacaagta cggcttctgg cacaacgggg      1860
ccgaggccga gagcccggag agctggctgg caggggcgac gcaccagggc ggctcctggt     1920
ggcccgagat gatgggcttt atccagaacc gtgacgaagg gtcagagccc gtccccgcgc     1980
gggtcccgga ggaagggctg ccccccgccc ccggccacta tgtcaaggtg cggctcaacc    2040
ccgtgtttgc ctgcccaaca gaggaggacg ccgcatgagc ctgacctgcc ggcctggttc      2100
aaccagtcgg cagccgacta gtggatccga gc                                     2132
```

<210> SEQ ID NO 44
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 44

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg      120
cgcactcccg ttctggataa tgttttttgc gccgacatca taacggttct ggcaaatatt      180
ctgaaatgag ctgttgacaa ttaatcatcg aactagttaa ctagtacgca agttcacagc      240
ggataacaat ttcacacagg aaacaattgc acgtgcagag agacaatcaa atcatgagcc      300
aaccatctta tggcccgctg ttcgaggccc tggcccacta caatgacaag ctgctggcca      360
tggccaaggc ccagacagag cgcaccgccc aggcgctgct gcagaccaat ctggacgatc      420
tgggccaggt gctggagcag ggcagccagc aaccctggca gctgatccag gcccagatga      480
```

```
actggtggca ggatcagctc aagctgatgc agcacaccct gctcaaaagc gcaggccagc      540
cgagcgagcc ggtgatcacc ccggagcgca gcgatcgccg cttcaaggcc gaggcctgga      600
gcgaacaacc catctatgac tacctcaagc agtcctacct gctcaccgcc aggcacctgc      660
tggcctcggt ggatgccctg gagggcgtcc cccagaagag ccgggagcgg ctgcgtttct      720
tcacccgcca gtacgtcagc gccatggccc ccagcaactt cctggccacc aaccccgagc      780
tgctcaagct gaccctggag tccggcggcc agaacctggt gcgcggactg gcctatttgg      840
ccgaggatct ggagcgcagc gccgatcagc tcaacatccg cctgaccgac gaatccgcct      900
tcgagctcgg gcgggatctg gccctgaccc cgggccgggt ggtgcagcgc accgagctct      960
atgagctcat tcagtacagc ccgactaccg agacggtggg caagacacct gtgctgatag     1020
tgccgccctt catcaacaag tactacatca tggacatgcg gccccagaac tccctggtcg     1080
cctggctggt cgcccagggc cagacggtat tcatgatctc ctggcgcaac ccgggcgtgg     1140
cccaggccca aatcgatctc gacgactacg tggtggatgg cgtcatcgcc gccctggacg     1200
gcgtggaggc ggccaccggc gagcggggag tgcacggcat cggctactgc atcgcggca      1260 ccgccctgtc gctcgccatg ggctggctgg cggcgcggcg ccagaagcag cgggtgcgca     1320
ccgccaccct gttcactacc ctgctggact tctcccagcc cggggagctt ggcatcttca     1380
tccacgagcc catcatagcg cgcgctcgagg cgcaaaatga ggccaagggc atcatggacg    1440
ggcgccagct ggcggtctcc ttcagcctgc tgcgggagaa cagcctctac tggaactact     1500
acatcgacag ctacctcaag ggtcagagcc cggtggcctt cgatctgctg cactggaaca     1560
gcgacagcac caatgtggcg ggcaagaccc acaacagcct gctgcgccgt ctctacctgg     1620
agaaccagct ggtgaagggg gagctcaaga tccgcaacac ccgcatcgat ctcggcaagg     1680
tgaagacccc tgtgctgctg gtgtcggcgg tggacgatca catcgccctc tggcagggca     1740
cctggcaggg catgaagctg tttggcgggg agcagcgctt cctcctggcg gagtccggcc     1800
acatcgccgg catcatcaac ccgccggccg ccaacaagta cggcttctgg cacaacgggg     1860
ccgaggccga gagcccggag agctggctgg caggggcgac gcaccagggc ggctcctggt     1920
ggcccgagat gatgggcttt atccagaacc gtgacgaagg gtcagagccc gtccccgcgc     1980
gggtcccgga ggaagggctg gcccccgccc ccggccacta tgtcaaggtg cggctcaacc     2040
ccgtgtttgc ctgcccaaca gaggaggacg ccgcatgagc ctgacctgcc ggcctggttc     2100
aaccagtcgg cagccgacta gtggatccga gc                                   2132
```

<210> SEQ ID NO 45
<211> LENGTH: 2132
<212> TYPE: DNA
<213> ORGANISM: Artificial Sequence
<220> FEATURE:
<223> OTHER INFORMATION: Gene expressing cassette
<400> SEQUENCE: 45

```
cctagggtgt acattgcgct gaaagaaggg ccaattgtgc ttctggcgtc aggcagccat       60
cggaagctgt ggtatggctg tgcaggtcgt aaatcactgc ataattcgtg tcgctcaagg      120
cgcactcccg ttctggataa tgttttttgc gccgacatca taacggttct ggcaaatatt      180
ctgaaatgag ctgttgacaa ttaatcatcg aactagttaa ctagtacgca agttcacagc      240
ggataacaat ttcacacagg aaacaattgc acgtgcagag agacaatcaa atcatgagcc      300
aaccatctta tggcccgctg ttcgaggccc tggcccacta caatgacaag ctgctggcca      360
tggccaaggc ccagacagag cgcaccgccc aggcgctgct gcagaccaat ctggacgatc      420
```

```
tgggccaggt gctggagcag ggcagccagc aaccctggca gctgatccag gcccagatga    480
actggtggca ggatcagctc aagctgatgc agcacaccct gctcaaaagc gcaggccagc    540
cgagcgagcc ggtgatcacc ccggagcgca gcgatcgccg cttcaaggcc gaggcctgga    600
gcgaacaacc catctatgac tacctcaagc agtcctacct gctcaccgcc aggcacctgc    660
tggcctcggt ggatgccctg gagggcgtcc cccagaagag ccgggagcgg ctgcgttt ct    720 tcacccgcca gtacgtcagc gccatggccc cagcaacttt cctggccacc aaccccgagc    780
tgctcaagct gaccctggag tccggcggcc agaacctggt gcgcggactg gccctcttgg    840
ccgaggatct ggtgcgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag   1020
tgccgccctt catcaacaag tactacatca tggacatgcg gccccagaac tccctggtcg   1080
cctggctggt cgcccagggc cagacggtat tcatgatctc ctggcgcaac ccgggcgtgg   1140
cccaggccca aatcgatctc gacgactacg tggtggatgg cgtcatcgcc gccctggacg   1200
gcgtggaggc ggccaccggc gagcgggagg tgcacggcat cggctactgc atcggcggca   1260
ccgccctgtc gctcgccatg ggctggctgg cggcgcggcg ccagaagcag cgggtgcgca   1320
ccgccaccct gttcactacc ctgctggact tctcccagcc cggggagctt ggcatcttca   1380
tccacgagcc catcatagcg gcgctcgagg cgcaaaatga ggccaagggc atcatggacg   1440
ggcgccagct ggcggtctcc ttcagcctgc tgcgggagaa cagcctctac tggaactact   1500
acatcgacag ctacctcaag ggtcagagcc cggtggcctt cgatctgctg cactggaaca   1560
gcgacagcac caatgtggcg ggcaagaccc acaacagcct gctgcgccgt ctctacctgg   1620
agaaccagct ggtgaagggg gagctcaaga tccgcaacac ccgcatcgat ctcggcaagg   1680
tgaagacccc tgtgctgctg gtgtcggcg tggacgatca catcgccctc tggcagggca   1740
cctggcaggg catgaagctg tttggcgggg agcagcgctt cctcctggcg gagtccggcc   1800
acatcgccgg catcatcaac ccgccggccg ccaacaagta cggcttctgg cacaacgggg   1860
ccgaggccga gagcccggag agctggctgg caggggcgac gcaccagggc ggctcctggt   1920
ggcccgagat gatgggcttt atccagaacc gtgacgaagg gtcagagccc gtccccgcgc   1980
gggtcccgga ggaagggctg gccccgccc cggccactg tgtcaaggtg cggctcaacc   2040
ccgtgtttgc ctgcccaaca gaggaggacg ccgcatgagc ctgacctgcc ggcctggttc   2100
aaccagtcgg cagccgacta gtggatccga gc                                 2132
```

<210> SEQ ID NO 46
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 46

```
cctagggtgt acattgcgct gaaagaaggg ccaattgtgc ttctggcgtc aggcagccat     60
cggaagctgt ggtatggctg tgcaggtcgt aaatcactgc ataattcgtg tcgctcaagg    120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
```

```
aaccatctta tggcccgctg ttcgaggccc tggcccacta caatgacaag ctgctggcca      360
tggccaaggc ccagacaaat cgcaccgccc aggcgctgct gcagaccaat ctggacgatc      420
tgggccaggt gctggagcag ggcagccagc aaccctggca gctgatccag gcccagatga      480
actggtggca ggatcagctc aagctgatgc agcacaccct gctcaaaagc gcaggccagc      540
cgagcgagcc ggtgatcacc ccggagcgca gcgatcgccg cttcaaggcc gaggcctgga      600
gcgaacaacc catctatgac tacctcaagc agtcctacct gctcaccgcc aggcacctgc      660
tggcctcggt ggatgccctg gagggcgtcc cccagaagag ccgggagcgg ctgcgtttct      720
tcacccgcca gtacgtcagc gccatggccc ccagcaactt cctggccacc aaccccgagc      780
tgctcaagct gaccctggag tccggcggcc agaacctggt gcgcggactg aagctcttgg      840
ccgaggatct ggagcgcagc gccgatcagc tcaacatccg cctgaccgac gaatccgcct      900
tcgagctcgg gcgggatctg gccctgaccc cgggccgggt ggtgcagcgc accgagctct      960
atgagctcat tcagtacagc ccgactaccg agacggtggg caagacacct gtgctgatag     1020
tgccgcccct catcaacaag tactacatca tggacatgcg gccccagaac tccctggtcg     1080
cctggctggt cgcccagggc cagacggtat tcatgatctc ctggcgcaac ccgggcgtgg     1140
cccaggccca aatcgatctc gacgactacg tggtggatgg cgtcatcgcc gccctggacg     1200
gcgtggaggc ggccaccggc gagcgggagg tgcacggcat cggctactgc atcggcggca     1260 ccgcccctgtc gctcgccatg ggctggctgg cggcgcggcg ccagaagcag cgggtgcgca     1320
ccgccaccct gttcactacc ctgctggact ctcccagcc cggggagctt ggcatcttca      1380
tccacgagcc catcatagcg gcgctcgagg cgcaaaatga ggccaagggc atcatggacg     1440
ggcgccagct ggcggtctcc ttcagcctgc tgcgggagaa cagcctctac tggaactact     1500
acatcgacag ctacctcaag ggtcagagcc cggtggcctt cgatctgctg cactggaaca     1560
gcgacagcac caatgtggcg ggcaagaccc acaacagcct gctgcgccgt ctctacctgg     1620
agaaccagct ggtgaagggg gagctcaaga tccgcaacac ccgcatcgat ctcggcaagg     1680
tgaagacccc tgtgctgctg gtgtcggcgg tggacgatca catcgccctc tggcagggca     1740
cctggcaggg catgaagctg tttggcgggg agcagcgctt cctcctggcg gagtccggcc     1800
acatcgccgg catcatcaac ccgccggccg ccaacaagta cggcttctgg cacaacgggg     1860
ccgaggccga gagcccggag agctggctgg caggggcgac gcaccagggc ggctcctggt     1920
ggcccgagat gatgggcttt atccagaacc gtgacgaagg gtcagagccc gtccccgcgc     1980
gggtcccgga ggaagggctg gccccgcgcc cggccacta tgtcaaggtg cggctcaacc      2040
ccgtgtttgc ctgcccaaca gaggaggacg ccgcatgagc ctgacctgcc ggcctggttc     2100
aaccagtcgg cagccgacta gtggatccga gc                                   2132
```

<210> SEQ ID NO 47
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 47

```
cctagggtgt acattgcgct gaaagaaggg ccaattgtgc ttctggcgtc aggcagccat       60
cggaagctgt ggtatggctg tgcaggtcgt aaatcactgc ataattcgtg tcgctcaagg      120
cgcactcccg ttctggataa tgttttttgc gccgacatca taacggttct ggcaaatatt      180
ctgaaatgag ctgttgacaa ttaatcatcg aactagttaa ctagtacgca agttcacagc      240
```

```
ggataacaat ttcacacagg aaacaattgc acgtgcagag agacaatcaa atcatgagcc      300
aaccatctta tggcccgctg ttcgaggccc tggcccacta caatgacaag ctgctggcca      360
tggccaaggc ccagacaaat cgcaccgccc aggcgctgct gcagaccaat ctggacgatc      420
tgggccaggt gctggagcag ggcagccagc aaccctggca gctgatccag gcccagatga      480
actggtggca ggatcagctc aagctgatgc agcacaccct gctcaaaagc gcaggccagc      540
cgagcgagcc ggtgatcacc ccggagcgca gcgatcgccg cttcaaggcc gaggcctgga      600
gcgaacaacc catctatgac tacctcaagc agtcctacct gctcaccgcc aggcacctgc      660
tggcctcggt ggatgccctg gagggcgtcc cccagaagag ccgggagcgg ctgcgtttct      720
tcacccgcca gtacgtcagc gccatggccc ccagcaactt cctggccacc aaccccgagc      780
tgctcaagct gaccctggag tccggcggcc agaacctggt gcgcggactg aggtcttgg       840 ccgaggatct ggagcgcagc gccgatcagc tcaacatccg cctgaccgac gaatccgcct      900
tcgagctcgg gcgggatctg gccctgaccc cgggccgggt ggtgcagcgc accgagctct      960
atgagctcat tcagtacagc ccgactaccg agacggtggg caagacacct gtgctgatag     1020
tgccgccctt catcaacaag tactacatca tggacatgcg gccccagaac tccctggtcg     1080
cctggctggt cgcccagggc cagacggtat tcatgatctc ctggcgcaac ccgggcgtgg     1140
cccaggccca aatcgatctc gacgactacg tggtggatgg cgtcatcgcc gcctggacg      1200 gcgtggaggc ggccaccggc gagcgggagg tgcacggcat cggctactgc atcggcggca     1260
ccgccctgtc gctcgccatg gctggctgg cggcgcggcg ccagaagcag cgggtgcgca      1320
ccgccaccct gttcactacc ctgctggact tctcccagcc cggggagctt ggcatcttca     1380
tccacgagcc catcatagcg gcgctcgagg cgcaaaatga ggccaagggc atcatggacg     1440
ggcgccagct ggcggtctcc ttcagcctgc tgcgggagaa cagcctctac tggaactact     1500
acatcgacag ctacctcaag ggtcagagcc cggtggcctt cgatctgctg cactggaaca     1560
gcgacagcac caatgtggcg ggcaagaccc acaacagcct gctgcgccgt ctctacctgg     1620
agaaccagct ggtgaagggg gagctcaaga tccgcaacac ccgcatcgat ctcggcaagg     1680
tgaagacccc tgtgctgctg gtgtcggcgg tggacgatca catcgccctc tggcagggca     1740
cctggcaggg catgaagctg tttggcgggg agcagcgctt cctcctggcg gagtccggcc     1800
acatcgccgg catcatcaac ccgccggccg ccaacaagta cggcttctgg cacaacgggg     1860
ccgaggccga gagcccggag agctggctgg caggggcgac gcaccagggc ggctcctggt     1920
ggcccgagat gatgggcttt atccagaacc gtgacgaagg gtcagagccc gtccccgcgc     1980
gggtcccgga ggaagggctg ccccccgccc ccggccacta tgtcaaggtg cggctcaacc     2040
ccgtgtttgc ctgcccaaca gaggaggacg ccgcatgagc ctgacctgcc ggcctggttc     2100
aaccagtcgg cagccgacta gtggatccga gc                                   2132
```

<210> SEQ ID NO 48
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 48

```
cctagggtgt acattgcgct gaaagaaggg ccaattgtgc ttctggcgtc aggcagccat       60
cggaagctgt ggtatggctg tgcaggtcgt aaatcactgc ataattcgtg tcgctcaagg      120
```

```
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ccagacaagt cgcaccgccc aggcgctgct gcagaccaat ctggacgatc    420
tgggccaggt gctggagcag ggcagccagc aaccctggca gctgatccag gcccagatga    480
actggtggca ggatcagctc aagctgatgc agcacaccct gctcaaaagc gcaggccagc    540
cgagcgagcg ggtgatcacc ccggagcgca gcgatcgccg cttcaaggcc gaggcctgga    600
gcgaacaacc catctatgac tacctcaagc agtcctacct gctcaccgcc aggcacctgc    660
tggcctcggt ggatgccctg gagggcgtcc cccagaagag ccgggagcgg ctgcgttttct    720 tcacccgcca gtacgtcagc gccatggccc ccagcaactt cctggccacc aaccccgagc    780
tgctcaagct gaccctggag tccggcggcc agaacctggt gcgcggactg aagctcttgg    840
ccgaggatct ggagcgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag   1020
tgccgccctt catcaacaag tactacatca tggacatgcg gccccagaac tccctggtcg   1080
cctggctggt cgcccagggc cagacggtat tcatgatctc ctggcgcaac ccgggcgtgg   1140
cccaggccca aatcgatctc gacgactacg tggtggatgg cgtcatcgcc gccctggacg   1200
gcgtggaggc ggccaccggc gagcgggagg tgcacggcat cggctactgc atcggcggca   1260
ccgccctgtc gctcgccatg ggctggctgg cggcgcggcg ccagaagcag cgggtgcgca   1320
ccgccaccct gttcactacc ctgctggact tctcccagcc cggggagctt ggcatcttca   1380
tccacgagcc catcatagcg gcgctcgagg cgcaaaatga ggccaagggc atcatggacg   1440
ggcgccagct ggcggtctcc ttcagcctgc tgcgggagaa cagcctctac tggaactact   1500
acatcgacag ctacctcaag ggtcagagcc cggtggcctt cgatctgctg cactggaaca   1560
gcgacagcac caatgtggcg ggcaagaccc acaacagcct gctgcgccgt ctctacctgg   1620
agaaccagct ggtgaagggg gagctcaaga tccgcaacac ccgcatcgat ctcggcaagg   1680
tgaagacccc tgtgctgctg gtgtcggcgg tggacgatca catcgccctc tggcagggca   1740
cctggcaggg catgaagctg tttgcgggg agcagcgctt cctcctggcg gagtccggcc   1800
acatcgccgg catcatcaac ccgccggccg ccaacaagta cggcttctgg cacaacgggg   1860
ccgaggccga gagcccggag agctggctgg caggggcgac gcaccagggc ggctcctggt   1920
ggcccgagat gatgggcttt atccagaacc gtgacgaagg gtcagagccc gtccccgcgc   1980
gggtcccgga ggaagggctg gcccccgccc ccggccacta tgtcaaggtg cggctcaacc   2040
ccgtgtttgc ctgcccaaca gaggaggacg ccgcatgagc ctgacctgcc ggcctggttc   2100
aaccagtcgg cagccgacta gtggatccga gc                                 2132
```

<210> SEQ ID NO 49
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 49

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ccagacaagt cgcaccgccc aggcgctgct gcagaccaat ctggacgatc    420
tgggccaggt gctggagcag ggcagccagc aaccctggca gctgatccag gcccagatga    480
actggtggca ggatcagctc aagctgatgc agcacaccct gctcaaaagc gcaggccagc    540
cgagcgagcc ggtgatcacc ccggagcgca gcgatcgccg cttcaaggcc gaggcctgga    600
gcgaacaacc catctatgac tacctcaagc agtcctacct gctcaccgcc aggcacctgc    660
tggcctcggt ggatgccctg agggcgtcc cccagaagag ccgggagcgg ctgcgtttct    720
tcacccgcca gtacgtcagc gccatggccc ccagcaactt cctggccacc aaccccgagc    780
tgctcaagct gaccctggag tccggcggcc agaacctggt gcgcggactg aggctcttgg    840
ccgaggatct ggagcgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgccctgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg gcgctcgagg cgcaaaatga ggccaagggc atcatggacg    1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg gagtccggcc    1800
acatcgccgg catcatcaac ccgccggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc    1980
gggtcccgga ggaagggctg gccccgcccc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                  2132
```

<210> SEQ ID NO 50
<211> LENGTH: 2132
<212> TYPE: DNA

<213> ORGANISM: Artificial Sequence
<220> FEATURE:
<223> OTHER INFORMATION: Gene expressing cassette

<400> SEQUENCE: 50

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggccc tggcccacta caatgacaag ctgctggcca     360
tggccaaggc ccagacaaat cgcaccgccc aggcgctgct gcagaccaat ctggacgatc     420
tgggccaggt gctggagcag ggcagccagc aaccctggca gctgatccag gcccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctatgac tacctcaagc agtcctacct gctcaccgcc aggcacctgc     660
tggcctcggt ggatgccctg gagggcgtcc cccagaagag ccgggagcgg ctgcgtttct     720
tcacccgcca gtacgtcagc gccatggccc cagcaactt cctggccacc aaccccgagc     780
tgctcaagct gaccctggag tccgcggcc agaacctggt gcgcggactg aagctcttgg     840
ccgaggatct ggagcgcagc gccgatcagc tcaacatccg cctgaccgac gaatccgcct     900
tcgagctcgg gcgggatctg gccctgaccc cgggccgggt ggtgcagcgc accgagctct     960
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgcccgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg cgcctcgagg cgcaaaatga ggccaagggc atcatggacg    1440
ggcgccagct ggcggtcacc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat tcggcaagg    1680
tgaagacccc tgtgctgctg gtgtcggcgg tggacgatca catcgccctc tggcagggca    1740
cctggcaggg catgaagctg tttgcggggg agcagcgctt cctcctggcg gagtccggcc    1800
acatcgccgg catcatcaac cgccgggcg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc    1980
gggtcccgga ggaagggctg gccccgccc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                  2132
```

<210> SEQ ID NO 51
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 51

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tgggcccgctg ttcgaggccc tggcccacta caatgacaag ctgctggcca     360
tggccaaggc ccagacaaat cgcaccgccc aggcgctgct gcagaccaat ctggacgatc     420
tgggccaggt gctggagcag ggcagccagc aaccctggca gctgatccag gcccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctatgac tacctcaagc agtcctacct gctcaccgcc aggcacctgc     660
tggcctcggt ggatgccctg gagggcgtcc ccagaagag ccgggagcgg ctgcgtttct     720
tcaccegcca gtacgtcagc gccatggccc ccagcaactt cctggccacc aaccccgagc     780
tgctcaagct gacctggag tccggcgccc agaacctggt gcgcggactg aggctcttgg     840
ccgaggatct ggagcgcagc gccgatcagc tcaacatccg cctgaccgac gaatccgcct     900
tcgagctcgg gcgggatctg gccctgaccc cgggccgggt ggtgcagcgc accgagctct     960
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgcccctgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg gcgctcgagg cgcaaaatga ggccaagggc atcatggacg    1440
ggcgccagct ggcggtcacc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagacca caacagcct gctgcgccgt ctctacctgg    1620
agaaccagct ggtgaagggg gagctcaaga tccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg gagtccggcc    1800
acatcgccgg catcatcaac ccgccggccg ccaacaagta cggcttctgg cacaacgggg    1860
ccgaggccga gagcccggag agctggctgg caggggcgac gcaccagggc ggctcctggt    1920
ggcccgagat gatgggcttt atccagaacc gtgacgaagg gtcagagccc gtccccgcgc    1980
gggtcccgga ggaagggctg gccccgccc ccggccacta tgtcaaggtg cggctcaacc    2040
ccgtgtttgc ctgcccaaca gaggaggacg ccgcatgagc ctgacctgcc ggcctggttc    2100
```

| aaccagtcgg cagccgacta gtggatccga gc | 2132 |

<210> SEQ ID NO 52
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 52

| cctagggtgt acattgcgct gaaagaaggg ccaattgtgc ttctggcgtc aggcagccat | 60 |
| cggaagctgt ggtatggctg tgcaggtcgt aaatcactgc ataattcgtg tcgctcaagg | 120 |
| cgcactcccg ttctggataa tgttttttgc gccgacatca taacggttct ggcaaatatt | 180 |
| ctgaaatgag ctgttgacaa ttaatcatcg aactagttaa ctagtacgca agttcacagc | 240 |
| ggataacaat ttcacacagg aaacaattgc acgtgcagag agacaatcaa atcatgagcc | 300 |
| aaccatctta tggcccgctg ttcgaggccc tggcccacta caatgacaag ctgctggcca | 360 |
| tggccaaggc ccagacaagt cgcaccgccc aggcgctgct gcagaccaat ctggacgatc | 420 |
| tgggccaggt gctggagcag ggcagccagc aaccctggca gctgatccag gcccagatga | 480 |
| actggtggca ggatcagctc aagctgatgc agcacaccct gctcaaaagc gcaggccagc | 540 |
| cgagcgagcc ggtgatcacc ccggagcgca gcgatcgccg cttcaaggcc gaggcctgga | 600 |
| gcgaacaacc catctatgac tacctcaagc agtcctacct gctcaccgcc aggcacctgc | 660 |
| tggcctcggt ggatgccctg gagggcgtcc cccagaagag ccgggagcgg ctgcgttcct | 720 |
| tcacccgcca gtacgtcagc gccatggccc cagcaactt cctggccacc aaccccgagc | 780 |
| tgctcaagct gaccctggag tccggcggcc agaacctggt gcgcggactg aagctcttgg | 840 |
| ccgaggatct ggagcgcagc gccgatcagc tcaacatccg cctgaccgac gaatccgcct | 900 |
| tcgagctcgg gcgggatctg gccctgaccc cgggccgggt ggtgcagcgc accgagctct | 960 |
| atgagctcat tcagtacagc ccgactaccg agacggtggg caagacacct gtgctgatag | 1020 |
| tgccgccctt catcaacaag tactacatca tggacatgcg gccccagaac tccctggtcg | 1080 |
| cctggctggt cgcccagggc cagacggtat tcatgatctc ctggcgcaac ccgggcgtgg | 1140 |
| cccaggccca aatcgatctc gacgactacg tggtggatgg cgtcatcgcc gccctggacg | 1200 |
| gcgtggaggc ggccaccggc gagcgggagg tgcacggcat cggctactgc atcggcggca | 1260 |
| ccgccctgtc gctcgccatg ggctggctgg cggcgcggcg ccagaagcag cgggtgcgca | 1320 |
| ccgccaccct gttcactacc ctgctggact tctcccagcc cggggagctt ggcatcttca | 1380 |
| tccacgagcc catcatagcg gcgctcgagg cgcaaaatga ggccaagggc atcatggacg | 1440 |
| ggcgccagct ggcggtcacc ttcagcctgc tgcgggagaa cagcctctac tggaactact | 1500 |
| acatcgacag ctacctcaag ggtcagagcc cggtggcctt cgatctgctg cactggaaca | 1560 |
| gcgacagcac caatgtggcg ggcaagaccc acaacagcct gctgcgccgt ctctacctgg | 1620 |
| agaaccagct ggtgaagggg gagctcaaga tccgcaacac ccgcatcgat ctcggcaagg | 1680 |
| tgaagacccc tgtgctgctg gtgtcggcgg tggacgatca catcgccctc tggcagggca | 1740 |
| cctggcaggg catgaagctg tttgcgggga gcagcgctt cctcctggcg gagtccggcc | 1800 |
| acatcgccgg catcatcaac ccgccggccg ccaacaagta cggcttctgg cacaacgggg | 1860 |
| ccgaggccga gagcccggag agctggctgg caggggcgac gcaccagggc ggctcctggt | 1920 |
| ggcccgagat gatgggcttt atccagaacc gtgacgaagg gtcagagccc gtccccgcgc | 1980 |
| gggtcccgga ggaagggctg gccccccgccc ccggccacta tgtcaaggtg cggctcaacc | 2040 |

```
ccgtgtttgc ctgcccaaca gaggaggacg ccgcatgagc ctgacctgcc ggcctggttc    2100
aaccagtcgg cagccgacta gtggatccga gc                                  2132

<210> SEQ ID NO 53
<211> LENGTH: 2132
<212> TYPE: DNA
<213> ORGANISM: Artificial Sequence
<220> FEATURE:
<223> OTHER INFORMATION: Gene expressing cassette

<400> SEQUENCE: 53
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
cgcactcccg ttctggataa tgttttttgc gccgacatca taacggttct ggcaaatatt     180
ctgaaatgag ctgttgacaa ttaatcatcg aactagttaa ctagtacgca agttcacagc     240
ggataacaat ttcacacagg aaacaattgc acgtgcagag agacaatcaa atcatgagcc     300
aaccatctta tggcccgctg ttcgaggccc tggcccacta caatgacaag ctgctggcca     360
tggccaaggc ccagacaagt cgcaccgccc aggcgctgct gcagaccaat ctggacgatc     420
tgggccaggt gctggagcag ggcagccagc aaccctggca gctgatccag gcccagatga     480
actggtggca ggatcagctc aagctgatgc agcacaccct gctcaaaagc gcaggccagc     540
cgagcgagcc ggtgatcacc ccggagcgca gcgatcgccg cttcaaggcc gaggcctgga     600
gcgaacaacc catctatgac tacctcaagc agtcctacct gctcaccgcc aggcacctgc     660
tggcctcggt ggatgccctg agggcgtcc cccagaagag ccgggagcgg ctgcgtttct     720
tcacccgcca gtacgtcagc gccatggccc cagcaactt cctggccacc aaccccgagc     780
tgctcaagct gaccctggag tccggcggcc agaacctggt gcgcggactg aggctcttgg     840
ccgaggatct ggagcgcagc gccgatcagc tcaacatccg cctgaccgac gaatccgcct     900
tcgagctcgg gcgggatctg gccctgaccc cgggccgggt ggtgcagcgc accgagctct     960
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgccctgtc gctcgccatg ggctggctgg cggcgcggcg ccagaagcag cgggtgcgca    1320
ccgccaccct gttcactacc ctgctggact ctcccagcc cggggagctt ggcatcttca    1380
tccacgagcc catcatagcg gcgctcgagg cgcaaaatga ggccaagggc atcatggacg    1440
ggcgccagct ggcggtcacc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg gagtccggcc    1800
acatcgccgg catcatcaac cgccggccg ccaacaagta cggcttctgg cacaacgggg    1860
ccgaggccga gagcccggag agctggctgg caggggcgac gcaccagggc ggctcctggt    1920
```

```
ggcccgagat gatgggcttt atccagaacc gtgacgaagg gtcagagccc gtccccgcgc    1980
gggtcccgga ggaagggctg gcccccgccc ccggccacta tgtcaaggtg cggctcaacc    2040
ccgtgtttgc ctgcccaaca gaggaggacg ccgcatgagc ctgacctgcc ggcctggttc    2100
aaccagtcgg cagccgacta gtggatccga gc                                 2132
```

MUTANT POLYHYDROXYALKANOATE SYNTHETASE, GENE AND TRANSFORMANT THEREOF, AND METHOD FOR PRODUCING POLYHYDROXYALKANOATE

TECHNICAL FIELD

The present invention relates to a mutant polyhydroxyalkanoate synthetase, a gene encoding the enzyme, a transformant having the gene, and a method for producing polyhydroxyalkanoate using the transformant.

BACKGROUND ART

Polyhydroxyalkanoate (hereinafter, abbreviated as "PHA") is thermoplastic polyester produced and accumulated as an energy storage substance in cells of many microbial species. PHA, which is produced from various natural carbon sources by microorganisms, is an environmentally friendly plastic that is completely biodegraded by microorganisms in soil and water.

As PHA, poly-3-hydroxybutyrate (hereinafter, abbreviated as "PHB"), which is a homopolymer of 3-hydroxybutyrate (hereinafter, abbreviated as "3HB"), is known as crystalline polymer, and PHB is hard and brittle due to its high crystallinity. In addition, PHB has a problem of poor processability in melt processing.

As PHA in which the brittleness and the melt processability of PHB are improved, poly(3HB-co-3HH) (hereinafter, abbreviated as "PHBH"), which is copolymerized polyester of 3HB and 3-hydroxyhexanoate (hereinafter, abbreviated as "3HH") has been reported. PHBH is a copolymer which has 3HH as a monomer unit, and thus has a lower crystallinity as compared to PHB, and flexible and soft properties.

As a method for producing PHBH, it has been reported that PHBH is produced by fermentation using a transformant obtained by introducing a PHA synthetase derived from *Aeromonas caviae* into *Cupriavidus necator*, which is a soil bacterium, as a host. In order to enhance the flexibility of PHBH, studies are being conducted for increasing the 3HH ratio in PHBH.

NPTLs 1 and 2 describe methods for introducing a mutation into a PHA synthetase in order to increase the 3HH ratio in PHBH. Specifically, NPTL 1 reports that a mutation of substitution of asparagine at the 149th position with serine or substitution of aspartic acid at the 171st position with glycine is introduced into an *A. caviae*-derived PHA synthetase to improve the activity of PHA synthetase and the substrate specificity to 3HH-CoA, so that PHBH having a 3HH fraction of maximum 18 mol % can be produced.

Further, NPTL 2 reports that PHBH with a higher 3HH ratio can be produced by a PHA synthase having these two mutations (hereinafter, abbreviated as "NSDG").

CITATION LIST

Non Patent Literature

NPTL 1: T. Kichise, S. Taguchi, Y. Doi, App. Environ. Microbiol., 68, pp. 2411-2419 (2002).
NPTL 2: T. Tsuge, S. Watanabe, D. Shimada, H. Abe, Y. Doi, S. Taguchi, FEMS Microbiol. Lett., 277, pp. 217-222 (2007).

SUMMARY OF INVENTION

Technical Problem

Currently, the 3HH ratio of a PHA copolymer that can be produced by culturing a transformant is limited. Thus, it is desired to construct a PHA synthetase library which enables production of a PHA copolymer with a higher 3HH ratio.

Accordingly, an object of the present invention is to provide a mutant PHA synthetase which enables production of a PHA copolymer with a high 3HH ratio while maintaining PHA productivity; a gene encoding the enzyme; a transformant having the gene; and a method for producing PHA using the transformant.

Solution to Problem

The present inventors have extensively conducted studies for solving the above-described problems, and resultantly found that introduction of a mutation to at least one of amino acids at the 27th to 33rd positions, amino acids at the 39th, 56th, 106th, 129th, 144th, 165th and 170th positions and amino acids at the 172nd to 187th positions from the N-terminus in a PHA synthetase $PhaC_{Ac}$ consisting of the amino acid sequence of SEQ ID NO: 1 and derived from *Aeromonas caviae* enables production of a PHA copolymer having a high 3HH ratio while maintaining productivity of PHA, leading to completion of the present invention.

That is, the present invention relates to a mutant polyhydroxyalkanoate synthetase having 85% or more sequence identity with the amino acid sequence of SEQ ID NO: 1 and having any one or more of mutations (A) to (C):

mutation (A): mutation of substitution of at least one of the amino acids at the 27th to 33rd positions from the N-terminus of the amino acid sequence of SEQ ID NO: 1 with another amino acid;

mutation (B): mutation of substitution of at least one of the amino acids at the 39th, 56th, 106th, 129th, 144th, 165th and 170th positions from the N-terminus of the amino acid sequence of SEQ ID NO: 1 with another amino acid; and mutation (C): mutation of substitution of at least one of the amino acids at the 172nd to 187th positions from the N-terminus of the amino acid sequence of SEQ ID NO: 1 with another amino acid.

Preferably, one or more of the mutations (A) to (C) are one or more of the following mutations (a) to (q):

mutation (a): mutation of substitution of glutamine at the 27th position from the N-terminus of the amino acid sequence of SEQ ID NO: 1 with another amino acid;

mutation (b): mutation of substitution of glutamic acid at the 29th position from the N-terminus of the amino acid sequence of SEQ ID NO: 1 with another amino acid;

mutation (c): mutation of substitution of arginine at the 30th position from the N-terminus of the amino acid sequence of SEQ ID NO: 1 with another amino acid;

mutation (d): mutation of substitution of threonine at the 31st position from the N-terminus of the amino acid sequence of SEQ ID NO: 1 with another amino acid;

mutation (e): mutation of substitution of glutamine at the 33rd position from the N-terminus of the amino acid sequence of SEQ ID NO: 1 with another amino acid;

mutation (f): mutation of substitution of asparagine at the 39th position from the N-terminus of the amino acid sequence of SEQ ID NO: 1 with another amino acid;

mutation (g): mutation of substitution of glutamine at the 56th position from the N-terminus of the amino acid sequence of SEQ ID NO: 1 with another amino acid;

mutation (h): mutation of substitution of proline at the 106th position from the N-terminus of the amino acid sequence of SEQ ID NO: 1 with another amino acid;

mutation (i): mutation of substitution of leucine at the 129th position from the N-terminus of the amino acid sequence of SEQ ID NO: 1 with another amino acid;

mutation (j): mutation of substitution of threonine at the 144th position from the N-terminus of the amino acid sequence of SEQ ID NO: 1 with another amino acid;

mutation (k): mutation of substitution of lysine at the 165th position from the N-terminus of the amino acid sequence of SEQ ID NO: 1 with another amino acid;

mutation (l): mutation of substitution of serine at the 170th position from the N-terminus of the amino acid sequence of SEQ ID NO: 1 with another amino acid;

mutation (m): mutation of substitution of valine at the 176th position from the N-terminus of the amino acid sequence of SEQ ID NO: 1 with another amino acid;

mutation (n): mutation of substitution of leucine at the 179th position from the N-terminus of the amino acid sequence of SEQ ID NO: 1 with another amino acid;

mutation (o): mutation of substitution of alanine at the 180th position from the N-terminus of the amino acid sequence of SEQ ID NO: 1 with another amino acid;

mutation (p): mutation of substitution of leucine at the 181st position from the N-terminus of the amino acid sequence of SEQ ID NO: 1 with another amino acid; and mutation (q): mutation of substitution of glutamic acid at the 187th position from the N-terminus of the amino acid sequence of SEQ ID NO: 1 with another amino acid.

Hereinafter, specific embodiments will be shown. The mutation (a) is a mutation of substitution of glutamine at the 27th position from the N-terminus of the amino acid sequence of SEQ ID NO: 1 with serine. The mutation (b) is a mutation of substitution of glutamic acid at the 29th position from the N-terminus of the amino acid sequence of SEQ ID NO: 1 with asparagine or serine. The mutation (c) is a mutation of substitution of arginine at the 30th position from the N-terminus of the amino acid sequence of SEQ ID NO: 1 with glycine or proline. The mutation (d) is a mutation of substitution of arginine at the 31st position from the N-terminus of the amino acid sequence of SEQ ID NO: 1 with threonine or proline. The mutation (e) is a mutation of substitution of glutamine at the 33rd position from the N-terminus of the amino acid sequence of SEQ ID NO: 1 with isoleucine, leucine or valine. The mutation (f) is a mutation of substitution of asparagine at the 39th position from the N-terminus of the amino acid sequence of SEQ ID NO: 1 with alanine, cysteine, phenylalanine, histidine, isoleucine, methionine, glutamine or tryptophan. The mutation (g) is a mutation of substitution of glutamine at the 56th position from the N-terminus of the amino acid sequence of SEQ ID NO: 1 with proline. The mutation (h) is a mutation of substitution of proline at the 106th position from the N-terminus of the amino acid sequence of SEQ ID NO: 1 with alanine. The mutation (i) is a mutation of substitution of leucine at the 129th position from the N-terminus of the amino acid sequence of SEQ ID NO: 1 with glutamine. The mutation (j) is a mutation of substitution of threonine at the 144th position from the N-terminus of the amino acid sequence of SEQ ID NO: 1 with leucine. The mutation (k) is a mutation of substitution of lysine at the 165th position from the N-terminus of the amino acid sequence of SEQ ID NO: 1 with valine. The mutation (l) is a mutation of substitution of serine at the 170th position from the N-terminus of the amino acid sequence of SEQ ID NO: 1 with glutamine. The mutation (m) is a mutation of substitution of valine at the 176th position from the N-terminus of the amino acid sequence of SEQ ID NO: 1 with tryptophan. The mutation (n) is a mutation of substitution of leucine at the 179th position from the N-terminus of the amino acid sequence of SEQ ID NO: 1 with arginine or glutamine. The mutation (o) is a mutation of substitution of alanine at the 180th position from the N-terminus of the amino acid sequence of SEQ ID NO: 1 with glycine, lysine or arginine. The mutation (p) is a mutation of substitution of leucine at the 181st position from the N-terminus of the amino acid sequence of SEQ ID NO: 1 with tyrosine. The mutation (q) is a mutation of substitution of glutamic acid at the 187th position from the N-terminus of the amino acid sequence of SEQ ID NO: 1 with valine.

In an embodiment, the amino acid sequence containing the mutation may further contain a mutation of substitution of asparagine at the 149th position from the N-terminus of the amino acid sequence of SEQ ID NO: 1 with serine. In an embodiment, the amino acid sequence containing the mutation may further contain a mutation of substitution of aspartic acid at the 171st position from the N-terminus of the amino acid sequence of SEQ ID NO: 1 with glycine. In still another embodiment, the amino acid sequence containing the mutation may further contain a mutation of substitution of serine at the 389th position from the N-terminus of the amino acid sequence of SEQ ID NO: 1 with cysteine, isoleucine, threonine or valine.

The present invention also relates to a gene encoding the mutant polyhydroxyalkanoate synthetase. Further, the present invention also relates to a transformant having the gene. The host of the transformant may be a bacterium. The bacterium may be a bacterium belonging to the genus *Cupriavidus*, may be *Cupriavidus necator*, or may be *Cupriavidus necator* H16.

The present invention also relates to a method for producing polyhydroxyalkanoate, including the step of culturing the transformant described above. The polyhydroxyalkanoate is preferably one containing 3-hydroxyhexanoate as a monomer unit, more preferably a copolymer of 3-hydroxybutyrate and 3-hydroxyhexanoate.

Advantageous Effects of Invention

According to the present invention, it is possible to provide a mutant PHA synthetase which enables production of a PHA copolymer with a high 3HH ratio while maintaining PHA productivity; a gene encoding the enzyme; and a transformant having the gene. In addition, by culturing the transformant, a PHA copolymer with a high 311H ratio can be produced by fermentation without lowering the productivity of PHA.

DESCRIPTION OF EMBODIMENTS

Hereinafter, the present invention will be described in detail.

(Mutant PHA Synthetase)

The mutant PHA synthetase according to the present invention has an amino acid sequence having 85% or more sequence identity with the amino acid sequence of SEQ ID NO: 1, and includes any one or more of the following mutations (A) to (C). The present invention also provides a gene encoding the mutant PHA synthetase (hereinafter, abbreviated as a "mutant PHA synthetase gene").

The mutant PHA synthetase of the present invention is an enzyme having PHA synthetizing activity, and has an amino acid sequence having 85% or more sequence identity with the amino acid sequence of SEQ ID NO: 1. The amino acid sequence of SEQ ID NO: 1 is an amino acid sequence of a PHA synthetase PhaC$_{Ac}$ derived from *Aeromonas caviae*. The mutant PHA synthetase of the present invention may have a mutation other than the following mutations (A) to (C) as long as the sequence identity is satisfied.

The mutant PHA synthetase of the present invention may be one that forms a fusion protein by binding to a heterologous protein having a different function. In this case, the amino acid sequence of the heterologous protein is not considered in calculation of the sequence identity.

In the mutant PHA synthetase of the present invention, the sequence identity with the amino acid sequence of SEQ ID NO: 1 may be 85% or more, and is preferably 90% or more, more preferably 95% or more, still more preferably 97% or more, even more preferably 98% or more, especially preferably 99% or more.

The nucleotide sequence of the mutant PHA synthetase gene of the present invention is not limited as long as the nucleotide sequence is a nucleotide sequence encoding amino acid sequences which form the mutant PHA synthetase of the present invention.

The origin of the mutant PHA synthetase and the mutant PHA synthetase gene of the present invention is not particularly limited, and is preferably *Aeromonas*, more preferably *Aeromonas caviae*.

The mutations (A) to (C) contained in the mutant PHA synthetase of the present invention will now be described. The mutant PHA synthetase of the present invention may contain any one of the mutations (A) to (C), or two or more of these mutations.

Mutation (A): at least one of the amino acids at the 27th to 33rd positions from the N-terminal of the amino acid sequence of SEQ ID NO: 1 is substituted with another amino acid. The amino acid substituted may be any of the amino acids at the 27th, 28th, 29th, 30th, 31st, 32nd and 33rd positions from the N-terminus of the amino acid sequence of SEQ ID NO: 1. The amino acid substituted is preferably any of the amino acids at the 27th, 29th, 30th, 31st and 33rd positions. The amino acid after the substitution can be selected with consideration given to PHA productivity and the 3HH ratio in PHA produced.

Mutation (B): at least one of the amino acids at the 39th, 56th, 106th, 129th, 144th, 165th and 170th positions from the N-terminal of the amino acid sequence of SEQ ID NO: 1 is substituted with another amino acid. Of these, the amino acid at the 39th position is most preferable. The amino acid after the substitution can be selected with consideration given to PHA productivity and the 3HH ratio in PHA produced.

Mutation (C): at least one of the amino acids at the 172nd to 187th positions from the N-terminal of the amino acid sequence of SEQ ID NO: 1 is substituted with another amino acid. The amino acid substituted is any of the amino acids at the 172nd, 173rd, 174th, 175th, 176th, 177th, 178th, 179th, 180th, 181st, 182nd, 183rd, 184th, 185th, 186th and 187th positions from the N-terminus of the amino acid sequence of SEQ ID NO: 1. The amino acid substituted is preferably any of the amino acids at the 176th to 187th positions, more preferably any of the amino acids at the 176th, 179th, 180th, 181st and 187th positions. The amino acid after the substitution can be selected with consideration given to PHA productivity and the 3HH ratio in PHA produced.

The mutant PHA synthetase according to one embodiment of the present invention has an amino acid sequence having 85% or more sequence identity with the amino acid sequence of SEQ ID NO: 1, and contains any one or more of the following mutations (a) to (q).

The mutations (a) to (q) contained in the mutant PHA synthetase of the present invention will now be described. The mutant PHA synthetase of the present invention may contain any one of the mutations (a) to (q), or two or more of these mutations.

Mutation (a): glutamine at the 27th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of glutamine at the 27th position with a nonpolar amino acid other than glutamine (e.g. asparagine, serine or threonine) is preferable, and a mutation of substitution of the glutamine with serine is more preferable.

Mutation (b): glutamic acid at the 29th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of glutamic acid at the 29th position with a nonpolar amino acid (e.g. asparagine, serine, threonine or glutamine) is preferable, and a mutation of substitution of the glutamic acid with asparagine or serine is more preferable.

Mutation (c): arginine at the 30th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of arginine at the 30th position with an amino acid less likely to form an α-helix (e.g. glycine, proline, serine or tyrosine) is preferable, and a mutation of substitution of the arginine with glycine or proline is more preferable.

Mutation (d): threonine at the 31st position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of threonine at the 31st position with an amino acid less likely to form an α-helix (e.g. glycine, proline, serine or tyrosine) is preferable, a mutation of substitution of the threonine with glycine or proline is more preferable, and a mutation of substitution of the threonine with proline is still more preferable.

Mutation (e): glutamine at the 33rd position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of glutamine at the 33rd position with a hydrophobic amino acid (e.g. alanine, glycine, phenylalanine, isoleucine, leucine, methionine, proline, valine, tryptophan or tyrosine) is preferable, and from the viewpoint of the size of the side chain, a mutation of substitution of the glutamine with a hydrophobic aliphatic amino acid (e.g. alanine, glycine, isoleucine, leucine, methionine, proline or valine) is more preferable, and a mutation of substitution of the glutamine with isoleucine, leucine or valine is still more preferable.

Mutation (f): asparagine at the 39th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of asparagine at the 39th position with alanine, cysteine, phenylalanine, histidine, isoleucine, methionine, glutamine or tryptophan is preferable.

Mutation (g): glutamine at the 56th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of glutamine at the 56th position with an amino acid less likely to form an α-helix (e.g. glycine, proline, serine or tyrosine) is preferable, a mutation of substitution of the glutamine with glycine or proline is more preferable, and a mutation of substitution of the glutamine with proline is still more preferable.

Mutation (h): proline at the 106th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of proline at the 106th position with a hydrophobic amino acid (e.g. alanine, glycine, phenylalanine, isoleucine, leucine, methionine, proline, valine, tryptophan or tyrosine) is preferable, and from the viewpoint of the size of the side chain, a mutation of substitution of the proline with a hydrophobic aliphatic amino acid (e.g. alanine, glycine, isoleucine, leucine, methionine, proline or valine) is more preferable, and a mutation of substitution of the proline with alanine is still more preferable.

Mutation (i): leucine at the 129th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of leucine at the 129th position with a nonpolar amino acid (e.g. asparagine, serine, threonine or glutamine) is preferable, and a mutation of substitution of the leucine with glutamine is more preferable.

Mutation (j): threonine at the 144th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of threonine at the 144th position with a hydrophobic amino acid (e.g. alanine, glycine, phenylalanine, isoleucine, leucine, methionine, proline, valine, tryptophan or tyrosine) is preferable, and from the viewpoint of the size of the side chain, a mutation of substitution of the threonine with a hydrophobic aliphatic amino acid (e.g. alanine, glycine, isoleucine, leucine, methionine, proline or valine) is more preferable, and a mutation of substitution of the threonine with leucine is still more preferable.

Mutation (k): lysine at the 165th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of lysine at the 165th position with a hydrophobic amino acid (e.g. alanine, glycine, phenylalanine, isoleucine, leucine, methionine, proline, valine, tryptophan or tyrosine) is preferable, and from the viewpoint of the size of the side chain, a mutation of substitution of the lysine with a hydrophobic aliphatic amino acid (e.g. alanine, glycine, isoleucine, leucine, methionine, proline or valine) is more preferable, and a mutation of substitution of the lysine with valine is still more preferable.

Mutation (l): serine at the 170th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of serine at the 170th position with a nonpolar amino acid other than serine (e.g. asparagine, threonine or glutamine) is preferable, and a mutation of substitution of the serine with glutamine is more preferable.

Mutation (m): valine at the 176th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of valine at the 176th position with a hydrophobic amino acid other than valine (e.g. alanine, glycine, phenylalanine, isoleucine, methionine, proline, tryptophan or tyrosine) is preferable, a mutation of substitution of the valine with a hydrophobic aromatic amino acid (e.g. phenylalanine, tryptophan or tyrosine) is more preferable, and a mutation of substitution of the valine with tryptophan is still more preferable.

Mutation (n): leucine at the 179th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of leucine at the 179th position with a nonpolar amino acid (e.g. asparagine, glutamine, serine or threonine) or a basic amino acid (e.g. histidine, lysine or arginine) is preferable, and a mutation of substitution of the leucine with glutamine or arginine is more preferable.

Mutation (o): alanine at the 180th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of alanine at the 180th position with an amino acid less likely to form an α-helix (e.g. glycine, proline, serine or tyrosine) or a basic amino acid (e.g. histidine, lysine or arginine) is preferable, and a mutation of substitution of the alanine with glycine, lysine or arginine is more preferable.

Mutation (p): leucine at the 181st position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of leucine at the 181st position with a hydrophobic amino acid other than leucine (e.g. alanine, glycine, phenylalanine, isoleucine, methionine, proline, valine, tryptophan or tyrosine) is preferable, a mutation of substitution of the leucine with a hydrophobic aromatic amino acid (e.g. phenylalanine, tryptophan or tyrosine) is more preferable, and a mutation of substitution of the leucine with tyrosine is still more preferable.

Mutation (q): glutamic acid at the 187th position from the N-terminus of the amino acid sequence of SEQ ID NO: 1 is substituted with another amino acid. The amino acid after the substitution can be selected with consideration given to PHA productivity and the 3HH ratio in PHA produced. For producing PHA with a high 3HH ratio while maintaining PHA productivity, a mutation of substitution of glutamic acid at the 187th position with a hydrophobic amino acid (e.g. alanine, glycine, phenylalanine, isoleucine, leucine, methionine, proline, valine, tryptophan or tyrosine) is preferable, and from the viewpoint of the size of the side chain, a mutation of substitution of the glutamic acid with a hydrophobic aliphatic amino acid (e.g. alanine, glycine, isoleucine, leucine, methionine, proline or valine) is more preferable, and a mutation of substitution of the glutamic acid with valine is still more preferable.

For increasing the 3HH ratio of PHA, it is preferable that the amino acid sequence of the mutant PHA synthetase of the present invention further contains a mutation of substitution of asparagine at the 149th position from the N-terminus of the amino acid sequence of SEQ ID NO: 1 with serine, and/or a mutation of substitution of aspartic acid at the 171st position from the N-terminus of the amino acid sequence of SEQ ID NO: 1 with glycine, in addition to the mutations described above.

In addition, for further increasing the 3HH ratio of PHA, it is preferable that the amino acid sequence of the mutant PHA synthetase of the present invention further contains a mutation of substitution of serine at the 389th position from the N-terminus of the amino acid sequence of SEQ ID NO: 1 with cysteine, isoleucine, threonine or valine, in addition to the mutations described above.

(Transformant Producing 3HH Unit-Containing Copolymer PHA)

The transformant of the present invention is a transformant having a gene encoding the mutant PHA synthetase of the present invention, and is produced by introducing the gene into a host microorganism.

The host of the transformant of the present invention is not particularly limited, and any microorganisms such as funguses (molds, mushrooms, yeasts or the like), bacteria or archaea can be used, with bacteria being preferable. Preferred examples of the bacteria include bacteria belonging to the genera *Ralstonia, Cupriavidus, Wautersia, Aeromonas, Escherichia, Alcaligenes* and *Pseudomonas*. From the viewpoint of safety and productivity, the bacteria are more preferably bacteria belonging to the genus *Ralstonia, Cupriavidus, Aeromonas* or *Wautersia*, still more preferably bacteria belonging to the genus *Cupriavidus* or *Aeromonas*, even more preferably bacterial belonging to the genus *Cupriavidus*, especially preferably *Cupriavidus necator*, most preferably *Cupriavidus necator* H16.

As a method for introducing the mutant PHA synthetase gene of the present invention into a host microorganism in production of the transformant of the present invention, any method can be used. As an example, a known gene recombination technique may be used to introduce the mutant PHA synthetase gene of the present invention onto a DNA such as a chromosome, a plasmid or a megaplasmid of a host microorganism, or a plasmid vector or artificial chromosome having the gene may be introduced into the host microorganism. However, from the viewpoint of retaining the introduced gene, a method in which the gene is introduced onto a chromosome or megaplasmid of a microorganism is preferable, and a method in which the gene is introduced onto a chromosome of a microorganism is more preferable.

Methods for site-specifically substituting or inserting any nucleotide sequence on a DNA of a microorganism, or methods for deleting any nucleotide sequence in a DNA of a microorganism are widely known to those skilled in the art, and can be used in production of the transformant of the present invention. Typical methods include, but are not particularly limited to, a method using a transposon and a homologous recombination mechanism (Ohman et al., J. Bacteriol., Vol. 162: p. 1068 (1985)); a method based on site-specific integration caused by a homologous recombination mechanism and loss caused by second-stage homologous recombination (Noti et al., Methods Enzymol., Vol 0.154, p. 197 (1987)); and a method in which a sacB gene derived from *Bacillus subtilis* is made to coexist, and a microorganism strain with a gene lost by second-stage homologous recombination is easily isolated as a sucrose-containing medium resistant strain (Schweizer, Mol. Microbiol., Vol. 6, p. 1195 (1992); Lenz et al., J. Bacteriol., Vol. 176, p. 4385 (1994)). Examples of methods for introducing a vector into a microorganism include, but are not particularly limited, to calcium chloride methods, electroporation methods, polyethylene glycol methods and spheroplast methods.

As gene cloning and gene recombination techniques, techniques described in Sambrook, J. et al., Molecular Cloning, A Laboratory Manual, Cold Spring Harbor Laboratory Press (1989 or 2001) can be used.

In introduction of the mutant PHA synthetase gene of the present invention, the gene can be linked to an arbitrary expression control sequence. In the present specification, the expression control sequence is described as a sequence consisting of a promoter and a Shine-Dalgarno sequence. As such an expression control sequence, for example, the expression control sequence of the phaC1 gene (SEQ ID NO: 2) or the expression control sequence of the phaP1 gene (SEQ ID NO: 3) of *Cupriavidus* necator can be used. Alternatively, an *Escherichia coli*-derived lac promoter (SEQ ID NO: 4) or trp promoter (SEQ ID NO: 5), or an artificially prepared lacUV5 promoter (SEQ ID NO: 6), trc promoter (SEQ ID NO: 7), tic promoter (SEQ ID NO: 8), tac promoter (SEQ ID NO: 9), lacN17 promoter (SEQ ID NO: 10) and the like can be linked to the SD sequence (SEQ ID NO: 11) derived from the *Cupriavidus* necator H16 strain, and used as the expression control sequence.

(Method for Producing PHA)

By culturing the transformant of the present invention, the transformant can be caused to produce PHA, followed by collecting the obtained PHA to produce PHA.

In production of PHA according to the present invention, it is preferable to culture the transformant in a medium containing a carbon source, and a nitrogen source, an inorganic salts and other organic nutrient sources which are nutrient sources other than the carbon source.

The carbon source is not particularly limited as long as it is a carbon source which can be consumed by the transformant of the present invention and which contains oil and/or fatty acids, and any carbon source can be used. Specific examples include oils such as palm oil, palm kernel oil, corn oil, coconut oil, olive oil, soybean oil, rapeseed oil and jatropha oil, and fractionated oils thereof; fatty acids such as lauric acid, oleic acid, stearic acid, palmitic acid and myristic acid, and derivatives thereof.

Examples of the nitrogen source include ammonia; ammonium salts such as ammonium chloride, ammonium sulfate and ammonium phosphate; peptone, meat extracts, and yeast extracts.

Examples of the inorganic salts include potassium dihydrogen phosphate, disodium hydrogen phosphate, magnesium phosphate, magnesium sulfate and sodium chloride.

Examples of other organic nutrient sources include amino acids such as glycine, alanine, serine, threonine and proline; and vitamins such as vitamin B1, vitamin B12 and vitamin C.

The conditions for culturing the transformant of the present invention, such as a culture temperature, a culture time, pH in culture and a medium, are not particularly limited, and may be conditions which are commonly used for culture of host microorganisms, e.g. microorganisms such as the genus Ralstonia, Cupriavidus, Wautersia, Aeromonas, Escherichia, Alcaligenes or Pseudomonas.

The type of PHA produced in the present invention is not particularly limited as long as it is a PHA copolymer containing 3HH as a monomer unit. In particular, PHA copolymers obtained by polymerizing 3HH with one or more monomers selected from 2-hydroxyalkanoate, 3-hydroxyalkanoate (except for 3HH) and 4-hydroxyalkanoate having 4 to 16 carbon atoms are preferable, and P(3HB-co-3HH) which is a copolymer of 3-hydroxybutyrate and 3-hydroxyhexanoate is most preferable. The type of PHA produced can be appropriately selected according to the type of a PHA synthetase gene of a microorganism used or a PHA synthetase gene introduced separately, the type of a metabolic gene involved in PHA synthesis, the carbon source used for culture, and other culture conditions.

In the present invention, the method for recovery of PHA from bacterial cells after culturing the transformant is not particularly limited, and a known method can be used. As an example, PHA can be recovered by the following method. After completion of culture, bacterial cells are separated from a culture solution by a centrifuge or the like, and the bacterial cells are washed with distilled water, methanol or the like, and dried. PHA is extracted from the dried bacterial cells using an organic solvent such as chloroform. From the organic solvent solution containing PHA, bacterial cell components are removed by filtration or the like, and a poor solvent such as methanol or hexane is added to the filtrate to precipitate PHA. Further, the supernatant is removed by filtration or centrifugation, and dried to recover PHA.

The composition (mol %) of monomer units contained in the obtained PHA, such as 3HH units, can be analyzed by a gas chromatography method, a nuclear magnetic resonance method, or the like.

EXAMPLES

Hereinafter, the present invention will be described in further detail by way of examples, but the present invention is not limited to these examples.

The genetic manipulation described below can be performed with reference to Molecular Cloning (Cold Spring Harbor Laboratory Press (1989)). In addition, enzymes, cloning hosts and the like which are used for gene manipulation can be purchased from suppliers on the market, and used according to the instructions. The enzymes are not particularly limited as long as they can be used for gene manipulation.

(Production Example 1) Preparation of H16 ΔphaC1 Ptrc-phaJ4b dZ1,2,6 Strain

First, a phaC1 gene disrupting plasmid was prepared. A DNA fragment (SEQ ID NO: 12) having a nucleotide sequence upstream and downstream of the phaC1 gene was obtained by PCR using a synthetic oligo DNA. The obtained DNA fragment was digested with a restriction enzyme SwaI. This DNA fragment was linked to a vector pNS2X-sacB also digested with the SwaI and described in Japanese Patent Laid-Open No. 2007-259708. In this way, a gene disrupting plasmid vector pNS2X-sacB-phaC1UL having nucleotide sequences upstream and downstream of phaC1 was prepared.

Next, a ΔphaC1 Ptrc-phaJ4b dZ1,2,6 strain was prepared using pNS2X-sacB-phaC1UL. The pNS2X-sacB-phaC1UL was introduced into an Escherichia coli S17-1 strain (ATCC47055). The obtained transformant was mixed with a KNK005 trc-phaJ4b ΔphaZ1,2,6 strain (see International Publication No. 2015/115619) and cultured on Nutrient Agar medium (manufactured by Difco Company) to perform conjugation transfer.

The obtained culture solution was inoculated in a Simmons agar medium containing 250 mg/L kanamycin (sodium citrate: 2 g/L, sodium chloride: 5 g/L, magnesium sulfate heptahydrate: 0.2 g/L, ammonium dihydrogen phosphate: 1 g/L, dipotassium hydrogen phosphate: 1 g/L, agar: 15 g/L, pH: 6.8) to obtain a strain with pNS2X-sacB-phaC1UL integrated on the chromosome of a KNK005 trc-phaJ4b ΔphaZ1,2,6 strain. This strain was subjected to two-generation culture in Nutrient Broth medium (manufactured by Difco Company), and then diluted and applied onto Nutrient Agar medium containing 15% of sucrose to obtain a strain in which a plasmid had been lost. From the obtained transformants, one strain deleting a region from the start codon to the stop codon of the phaC1 gene on a chromosome was isolated by PCR and analysis with a DNA sequencer. This gene-disrupted strain was named H16 ΔphaC1 Ptrc-phaJ4b dZ1,2,6 strain.

The obtained H16 ΔphaC1 Ptrc-phaJ4b dZ1,2,6 strain is a strain in which a region from the start codon to the stop codon of the phaZ1 gene and the phaZ6 gene on a chromosome of Cupriavidus necator H16 strain is deleted, a region from 16th codon to the stop codon of the phaZ2 gene is deleted, expression of a R-body-specific enoyl-CoA hydratase gene on the chromosome is intensified, and a region from the start codon to the stop codon of the phaC1 gene is deleted.

(Production Example 2) Preparation of pCUP2-Ptrp-NSDG

A DNA fragment having the nucleotide sequence of SEQ ID NO: 13 was amplified by PCR using a synthetic oligo DNA or the like. Using In-fusion HD Cloning Kit (Takara Bio Inc.), the obtained DNA fragment was linked to a DNA fragment obtained by digesting the pCUP2 vector described in Japanese Patent Laid-Open No. 2007-259708 with MunI and SpaI In this way, pCUP2-Ptrp-NSDG was obtained.

The pCUP2-Ptrp-NSDG is a plasmid that expresses NSDG under the trp promoter.

The NSDG is a mutant PHA synthetase which consists of the amino acid sequence of SEQ ID NO: 14 and which is obtained by introducing two mutations of substitution of asparagine at the 149th position from the N-terminus with serine and substitution of aspartic acid at the 171st position from the N-terminus with glycine into the amino acid sequence of the SEQ ID NO: 1.

(Production Example 3) Preparation of pCUP2-Ptrp-NSDG-Q27S

Using as a template the pCUP2-Ptrp-NSDG prepared in Production Example 2, a DNA fragment having the nucleotide sequence of SEQ ID NO: 15 was amplified by PCR using a synthetic oligo DNA or the like. The DNA fragment was cloned into the pCUP2 vector in the same manner as in Production Example 2 to obtain pCUP2-Ptrp-NSDG-Q27S. The pCUP2-Ptrp-NSDG-Q27S is a plasmid that expresses NSDG-Q27S under the trp promoter.

The NSDG-Q27S is a mutant PHA synthetase in which glutamine at the 27th position from the N-terminus of the amino acid sequence of SEQ ID NO: 14 is substituted with serine.

(Production Example 4) Preparation of pCUP2-Ptrp-NSDG-E29N

Using as a template the pCUP2-Ptrp-NSDG prepared in Production Example 2, a DNA fragment having the nucleotide sequence of SEQ ID NO: 16 was amplified by PCR using a synthetic oligo DNA or the like. The DNA fragment was cloned into the pCUP2 vector in the same manner as in Production Example 2 to obtain pCUP2-Ptrp-NSDG-E29N. The pCUP2-Ptrp-NSDG-E29N is a plasmid that expresses NSDG-E29N under the trp promoter.

The NSDG-E29N is a mutant PHA synthetase in which aspartic acid at the 29th position from the N-terminus of the amino acid sequence of SEQ ID NO: 14 is substituted with asparagine.

(Production Example 5) Preparation of pCUP2-Ptrp-NSDG-E29S

Using as a template the pCUP2-Ptrp-NSDG prepared in Production Example 2, a DNA fragment having the nucleotide sequence of SEQ ID NO: 17 was amplified by PCR using a synthetic oligo DNA or the like. The DNA fragment was cloned into the pCUP2 vector in the same manner as in Production Example 2 to obtain pCUP2-Ptrp-NSDG-E29S. The pCUP2-Ptrp-NSDG-E29S is a plasmid that expresses NSDG-E29S under the trp promoter.

The NSDG-E29S is a mutant PHA synthetase in which aspartic acid at the 29th position from the N-terminus of the amino acid sequence of SEQ ID NO: 14 is substituted with serine.

(Production Example 6) Preparation of pCUP2-Ptrp-NSDG-R30G

Using as a template the pCUP2-Ptrp-NSDG prepared in Production Example 2, a DNA fragment having the nucleotide sequence of SEQ ID NO: 18 was amplified by PCR using a synthetic oligo DNA or the like. The DNA fragment was cloned into the pCUP2 vector in the same manner as in Production Example 2 to obtain pCUP2-Ptrp-NSDG-R30G. The pCUP2-Ptrp-NSDG-R30G is a plasmid that expresses NSDG-R30G under the trp promoter.

The NSDG-R30G is a mutant PHA synthetase in which arginine at the 30th position from the N-terminus of the amino acid sequence of SEQ ID NO: 14 is substituted with glycine.

(Production Example 7) Preparation of pCUP2-Ptrp-NSDG-R30P

Using as a template the pCUP2-Ptrp-NSDG prepared in Production Example 2, a DNA fragment having the nucleotide sequence of SEQ ID NO: 19 was amplified by PCR using a synthetic oligo DNA or the like. The DNA fragment was cloned into the pCUP2 vector in the same manner as in Production Example 2 to obtain pCUP2-Ptrp-NSDG-R30P. The obtained pCUP2-Ptrp-NSDG-R30P is a plasmid that expresses NSDG-R3 OP under the trp promoter.

The NSDG-R30P is a mutant PHA synthetase in which arginine at the 30th position from the N-terminus of the amino acid sequence of SEQ ID NO: 14 is substituted with proline.

(Production Example 8) Preparation of pCUP2-Ptrp-NSDG-T31P

Using as a template the pCUP2-Ptrp-NSDG prepared in Production Example 2, a DNA fragment having the nucleotide sequence of SEQ ID NO: 20 was amplified by PCR using a synthetic oligo DNA or the like. The DNA fragment was cloned into the pCUP2 vector in the same manner as in Production Example 2 to obtain pCUP2-Ptrp-NSDG-T31P. The obtained pCUP2-Ptrp-NSDG-T31P is a plasmid that expresses NSDG-T31P under the trp promoter.

The NSDG-T3 IP is a mutant PHA synthetase in which threonine at the 31st position from the N-terminus of the amino acid sequence of SEQ ID NO: 14 is substituted with proline.

(Production Example 9) Preparation of pCUP2-Ptrp-NSDG-Q33I

Using as a template the pCUP2-Ptrp-NSDG prepared in Production Example 2, a DNA fragment having the nucleotide sequence of SEQ ID NO: 21 was amplified by PCR using a synthetic oligo DNA or the like. The DNA fragment was cloned into the pCUP2 vector in the same manner as in Production Example 2 to obtain pCUP2-Ptrp-NSDG-Q33I. The pCUP2-Ptrp-NSDG-Q33I is a plasmid that expresses NSDG-Q33I under the trp promoter.

The NSDG-Q33I is a mutant PHA synthetase in which glutamine at the 33rd position from the N-terminus of the amino acid sequence of SEQ ID NO: 14 is substituted with isoleucine.

(Production Example 10) Preparation of pCUP2-Ptrp-NSDG-Q33L

Using as a template the pCUP2-Ptrp-NSDG prepared in Production Example 2, a DNA fragment having the nucleotide sequence of SEQ ID NO: 22 was amplified by PCR using a synthetic oligo DNA or the like. The DNA fragment was cloned into the pCUP2 vector in the same manner as in Production Example 2 to obtain pCUP2-Ptrp-NSDG-Q33L. The pCUP2-Ptrp-NSDG-Q33L is a plasmid that expresses NSDG-Q33L under the trp promoter.

The NSDG-Q33L is a mutant PHA synthetase in which glutamine at the 33rd position from the N-terminus of the amino acid sequence of SEQ ID NO: 14 is substituted with leucine.

(Production Example 11) Preparation of pCUP2-Ptrp-NSDG-Q33V

Using as a template the pCUP2-Ptrp-NSDG prepared in Production Example 2, a DNA fragment having the nucleotide sequence of SEQ ID NO: 23 was amplified by PCR using a synthetic oligo DNA or the like. The DNA fragment was cloned into the pCUP2 vector in the same manner as in Production Example 2 to obtain pCUP2-Ptrp-NSDG-Q33V. The pCUP2-Ptrp-NSDG-Q33V is a plasmid that expresses NSDG-Q33V under the trp promoter.

The NSDG-Q33V is a mutant PHA synthetase in which glutamine at the 33rd position from the N-terminus of the amino acid sequence of SEQ ID NO: 14 is substituted with valine.

(Production Example 12) Preparation of pCUP2-Ptrp-NSDG-N39A

Using as a template the pCUP2-Ptrp-NSDG prepared in Production Example 2, a DNA fragment having the nucleotide sequence of SEQ ID NO: 24 was amplified by PCR using a synthetic oligo DNA or the like. The DNA fragment was cloned into the pCUP2 vector in the same manner as in Production Example 2 to obtain pCUP2-Ptrp-NSDG-N39A. The pCUP2-Ptrp-NSDG-N39A is a plasmid that expresses NSDG-N39A under the trp promoter.

The NSDG-N39A is a mutant PHA synthetase in which asparagine at the 39th position from the N-terminus of the amino acid sequence of SEQ ID NO: 14 is substituted with alanine.

(Production Example 13) Preparation of pCUP2-Ptrp-NSDG-N39C

Using as a template the pCUP2-Ptrp-NSDG prepared in Production Example 2, a DNA fragment having the nucleotide sequence of SEQ ID NO: 25 was amplified by PCR using a synthetic oligo DNA or the like. The DNA fragment was cloned into the pCUP2 vector in the same manner as in Production Example 2 to obtain pCUP2-Ptrp-NSDG-N39C. The pCUP2-Ptrp-NSDG-N39C is a plasmid that expresses NSDG-N39C under the trp promoter.

The NSDG-N39C is a mutant PHA synthetase in which asparagine at the 39th position from the N-terminus of the amino acid sequence of SEQ ID NO: 14 is substituted with cysteine.

(Production Example 14) Preparation of pCUP2-Ptrp-NSDG-N39F

Using as a template the pCUP2-Ptrp-NSDG prepared in Production Example 2, a DNA fragment having the nucleotide sequence of SEQ ID NO: 26 was amplified by PCR using a synthetic oligo DNA or the like. The DNA fragment was cloned into the pCUP2 vector in the same manner as in Production Example 2 to obtain pCUP2-Ptrp-NSDG-N39F. The pCUP2-Ptrp-NSDG-N39F is a plasmid that expresses NSDG-N39F under the trp promoter.

The NSDG-N39F is a mutant PHA synthetase in which asparagine at the 39th position from the N-terminus of the amino acid sequence of SEQ ID NO: 14 is substituted with phenylalanine.

(Production Example 15) Preparation of pCUP2-Ptrp-NSDG-N39H

Using as a template the pCUP2-Ptrp-NSDG prepared in Production Example 2, a DNA fragment having the nucleotide sequence of SEQ ID NO: 27 was amplified by PCR using a synthetic oligo DNA or the like. The DNA fragment was cloned into the pCUP2 vector in the same manner as in Production Example 2 to obtain pCUP2-Ptrp-NSDG-N39H. The pCUP2-Ptrp-NSDG-N39H is a plasmid that expresses NSDG-N39H under the trp promoter.

The NSDG-N39H is a mutant PHA synthetase in which asparagine at the 39th position from the N-terminus of the amino acid sequence of SEQ ID NO: 14 is substituted with histidine.

(Production Example 16) Preparation of pCUP2-Ptrp-NSDG-N39I

Using as a template the pCUP2-Ptrp-NSDG prepared in Production Example 2, a DNA fragment having the nucleotide sequence of SEQ ID NO: 28 was amplified by PCR using a synthetic oligo DNA or the like. The DNA fragment was cloned into the pCUP2 vector in the same manner as in Production Example 2 to obtain pCUP2-Ptrp-NSDG-N39I. The pCUP2-Ptrp-NSDG-N39I is a plasmid that expresses NSDG-N39I under the trp promoter.

The NSDG-N39I is a mutant PHA synthetase in which asparagine at the 39th position from the N-terminus of the amino acid sequence of SEQ ID NO: 14 is substituted with isoleucine.

(Production Example 17) Preparation of pCUP2-Ptrp-NSDG-N39M

Using as a template the pCUP2-Ptrp-NSDG prepared in Production Example 2, a DNA fragment having the nucleotide sequence of SEQ ID NO: 29 was amplified by PCR using a synthetic oligo DNA or the like. The DNA fragment was cloned into the pCUP2 vector in the same manner as in Production Example 2 to obtain pCUP2-Ptrp-NSDG-N39M. The pCUP2-Ptrp-NSDG-N39M is a plasmid that expresses NSDG-N39M under the trp promoter.

The NSDG-N39M is a mutant PHA synthetase in which asparagine at the 39th position from the N-terminus of the amino acid sequence of SEQ ID NO: 14 is substituted with methionine.

(Production Example 18) Preparation of pCUP2-Ptrp-NSDG-N39Q

Using as a template the pCUP2-Ptrp-NSDG prepared in Production Example 2, a DNA fragment having the nucleotide sequence of SEQ ID NO: 30 was amplified by PCR using a synthetic oligo DNA or the like. The DNA fragment was cloned into the pCUP2 vector in the same manner as in Production Example 2 to obtain pCUP2-Ptrp-NSDG-N39Q. The pCUP2-Ptrp-NSDG-N39Q is a plasmid that expresses NSDG-N39Q under the trp promoter.

The NSDG-N39Q is a mutant PHA synthetase in which asparagine at the 39th position from the N-terminus of the amino acid sequence of SEQ ID NO: 14 is substituted with glutamine.

(Production Example 19) Preparation of pCUP2-Ptrp-NSDG-N39W

Using as a template the pCUP2-Ptrp-NSDG prepared in Production Example 2, a DNA fragment having the nucleotide sequence of SEQ ID NO: 31 was amplified by PCR using a synthetic oligo DNA or the like. The DNA fragment was cloned into the pCUP2 vector in the same manner as in Production Example 2 to obtain pCUP2-Ptrp-NSDG-N39W. The pCUP2-Ptrp-NSDG-N39W is a plasmid that expresses NSDG-N39W under the trp promoter.

The NSDG-N39W is a mutant PHA synthetase in which asparagine at the 39th position from the N-terminus of the amino acid sequence of SEQ ID NO: 14 is substituted with tryptophan.

(Production Example 20) Preparation of pCUP2-Ptrp-NSDG-Q56P

Using as a template the pCUP2-Ptrp-NSDG prepared in Production Example 2, a DNA fragment having the nucleotide sequence of SEQ ID NO: 32 was amplified by PCR using a synthetic oligo DNA or the like. The DNA fragment was cloned into the pCUP2 vector in the same manner as in Production Example 2 to obtain pCUP2-Ptrp-NSDG-Q56P. The pCUP2-Ptrp-NSDG-Q56P is a plasmid that expresses NSDG-Q56P under the tip promoter.

NSDG-Q56P is a mutant PHA synthetase in which glutamine at the 56th position from the N-terminus of the amino acid sequence of SEQ ID NO: 14 is substituted with proline.

(Production Example 21) Preparation of pCUP2-Ptrp-NSDG-P106A

Using as a template the pCUP2-Ptrp-NSDG prepared in Production Example 2, a DNA fragment having the nucleotide sequence of SEQ ID NO: 33 was amplified by PCR using a synthetic oligo DNA or the like. The DNA fragment was cloned into the pCUP2 vector in the same manner as in Production Example 2 to obtain pCUP2-Ptrp-NSDG-P106A. The pCUP2-Ptrp-NSDG-P106A is a plasmid that expresses NSDG-P106A under the trp promoter.

The NSDG-P106A is a mutant PHA synthetase in which proline at the 106th position from the N-terminus of the amino acid sequence of SEQ ID NO: 14 is substituted with alanine.

(Production Example 22) Preparation of pCUP2-Ptrp-NSDG-L129Q

Using as a template the pCUP2-Ptrp-NSDG prepared in Production Example 2, a DNA fragment having the nucleotide sequence of SEQ ID NO: 34 was amplified by PCR using a synthetic oligo DNA or the like. The DNA fragment was cloned into the pCUP2 vector in the same manner as in Production Example 2 to obtain pCUP2-Ptrp-NSDG-L129Q. The pCUP2-Ptrp-NSDG-L129Q is a plasmid that expresses NSDG-L129Q under the trp promoter.

The NSDG-L129Q is a mutant PHA synthetase in which leucine at the 129th position from the N-terminus of the amino acid sequence of SEQ ID NO: 14 is substituted with glutamine.

(Production Example 23) Preparation of pCUP2-Ptrp-NSDG-T144L

Using as a template the pCUP2-Ptrp-NSDG prepared in Production Example 2, a DNA fragment having the nucleotide sequence of SEQ ID NO: 35 was amplified by PCR using a synthetic oligo DNA or the like. The DNA fragment was cloned into the pCUP2 vector in the same manner as in Production Example 2 to obtain pCUP2-Ptrp-NSDG-T144L. The pCUP2-Ptrp-NSDG-T144L is a plasmid that expresses NSDG-T144L under the trp promoter.

The NSDG-T144L is a mutant PHA synthetase in which threonine at the 144th position from the N-terminus of the amino acid sequence of SEQ ID NO: 14 is substituted with leucine.

(Production Example 24) Preparation of pCUP2-Ptrp-NSDG-K165V

Using as a template the pCUP2-Ptrp-NSDG prepared in Production Example 2, a DNA fragment having the nucleotide sequence of SEQ ID NO: 36 was amplified by PCR using a synthetic oligo DNA or the like. The DNA fragment was cloned into the pCUP2 vector in the same manner as in Production Example 2 to obtain pCUP2-Ptrp-NSDG-K165V. The pCUP2-Ptrp-NSDG-K165V is a plasmid that expresses NSDG-K165V under the trp promoter.

The NSDG-K165V is a mutant PHA synthetase in which lysine at the 165th position from the N-terminus of the amino acid sequence of SEQ ID NO: 14 is substituted with valine.

(Production Example 25) Preparation of pCUP2-Ptrp-NSDG-S170Q

Using as a template the pCUP2-Ptrp-NSDG prepared in Production Example 2, a DNA fragment having the nucleotide sequence of SEQ ID NO: 37 was amplified by PCR using a synthetic oligo DNA or the like. The DNA fragment was cloned into the pCUP2 vector in the same manner as in Production Example 2 to obtain pCUP2-Ptrp-NSDG-S170Q. The pCUP2-Ptrp-NSDG-S170Q is a plasmid that expresses NSDG-S170Q under the trp promoter.

The NSDG-S170Q is a mutant PHA synthetase in which serine at the 170th position from the N-terminus of the amino acid sequence of SEQ ID NO: 14 is substituted with glutamine.

(Production Example 26) Preparation of pCUP2-Ptrp-NSDG-V176W

Using as a template the pCUP2-Ptrp-NSDG prepared in Production Example 2, a DNA fragment having the nucleotide sequence of SEQ ID NO: 38 was amplified by PCR using a synthetic oligo DNA or the like. The DNA fragment was cloned into the pCUP2 vector in the same manner as in Production Example 2 to obtain pCUP2-Ptrp-NSDG-V176W. The pCUP2-Ptrp-NSDG-V176W is a plasmid that expresses NSDG-V176W under the trp promoter.

The NSDG-V176W is a mutant PHA synthetase in which valine at the 176th position from the N-terminus of the amino acid sequence of SEQ ID NO: 14 is substituted with tryptophan.

(Production Example 27) Preparation of pCUP2-Ptrp-NSDG-L179Q

Using as a template the pCUP2-Ptrp-NSDG prepared in Production Example 2, a DNA fragment having the nucleotide sequence of SEQ ID NO: 39 was amplified by PCR using a synthetic oligo DNA or the like. The DNA fragment was cloned into the pCUP2 vector in the same manner as in Production Example 2 to obtain pCUP2-Ptrp-NSDG-L179Q. The pCUP2-Ptrp-NSDG-L179Q is a plasmid that expresses NSDG-L179Q under the trp promoter.

The NSDG-L179Q is a mutant PHA synthetase in which leucine at the 179th position from the N-terminus of the amino acid sequence of SEQ ID NO: 14 is substituted with glutamine.

(Production Example 28) Preparation of pCUP2-Ptrp-NSDG-L179R

Using as a template the pCUP2-Ptrp-NSDG prepared in Production Example 2, a DNA fragment having the nucleotide sequence of SEQ ID NO: 40 was amplified by PCR using a synthetic oligo DNA or the like. The DNA fragment was cloned into the pCUP2 vector in the same manner as in Production Example 2 to obtain pCUP2-Ptrp-NSDG-L179R. The pCUP2-Ptrp-NSDG-L179R is a plasmid that expresses NSDG-L179R under the trp promoter.

The NSDG-L179R is a mutant PHA synthetase in which leucine at the 179th position from the N-terminus of the amino acid sequence of SEQ ID NO: 14 is substituted with arginine.

(Production Example 29) Preparation of pCUP2-Ptrp-NSDG-A180G

Using as a template the pCUP2-Ptrp-NSDG prepared in Production Example 2, a DNA fragment having the nucleotide sequence of SEQ ID NO: 41 was amplified by PCR using a synthetic oligo DNA or the like. The DNA fragment was cloned into the pCUP2 vector in the same manner as in Production Example 2 to obtain pCUP2-Ptrp-NSDG-A180G. The pCUP2-Ptrp-NSDG-A180G is a plasmid that expresses NSDG-A180G under the trp promoter.

The NSDG-A180G is a mutant PHA synthetase in which alanine at the 180th position from the N-terminus of the amino acid sequence of SEQ ID NO: 14 is substituted with glycine.

(Production Example 30) Preparation of pCUP2-Ptrp-NSDG-A180K

Using as a template the pCUP2-Ptrp-NSDG prepared in Production Example 2, a DNA fragment having the nucleotide sequence of SEQ ID NO: 42 was amplified by PCR using a synthetic oligo DNA or the like. The DNA fragment was cloned into the pCUP2 vector in the same manner as in Production Example 2 to obtain pCUP2-Ptrp-NSDG-A180K. The pCUP2-Ptrp-NSDG-A180K is a plasmid that expresses NSDG-A180K under the tip promoter.

The NSDG-A180K is a mutant PHA synthetase in which alanine at the 180th position from the N-terminus of the amino acid sequence of SEQ ID NO: 14 is substituted with lysine.

(Production Example 31) Preparation of pCUP2-Ptrp-NSDG-A180R

Using as a template the pCUP2-Ptrp-NSDG prepared in Production Example 2, a DNA fragment having the nucleotide sequence of SEQ ID NO: 43 was amplified by PCR using a synthetic oligo DNA or the like. The DNA fragment was cloned into the pCUP2 vector in the same manner as in Production Example 2 to obtain pCUP2-Ptrp-NSDG-A180R. The pCUP2-Ptrp-NSDG-A180R is a plasmid that expresses NSDG-A180R under the trp promoter.

The NSDG-A180R is a mutant PHA synthetase in which alanine at the 180th position from the N-terminus of the amino acid sequence of SEQ ID NO: 14 is substituted with arginine.

(Production Example 32) Preparation of pCUP2-Ptrp-NSDG-L181Y

Using as a template the pCUP2-Ptrp-NSDG prepared in Production Example 2, a DNA fragment having the nucleotide sequence of SEQ ID NO: 44 was amplified by PCR using a synthetic oligo DNA or the like. The DNA fragment was cloned into the pCUP2 vector in the same manner as in Production Example 2 to obtain pCUP2-Ptrp-NSDG-L181Y. The pCUP2-Ptrp-NSDG-L181Y is a plasmid that expresses NSDG-L181Y under the trp promoter.

The NSDG-L181Y is a mutant PHA synthetase in which leucine at the 181st position from the N-terminus of the amino acid sequence of SEQ ID NO: 14 is substituted with tyrosine.

(Production Example 33) Preparation of pCUP2-Ptrp-NSDG-E187V

Using as a template the pCUP2-Ptrp-NSDG prepared in Production Example 2, a DNA fragment having the nucleotide sequence of SEQ ID NO: 45 was amplified by PCR using a synthetic oligo DNA or the like. The DNA fragment was cloned into the pCUP2 vector in the same manner as in Production Example 2 to obtain pCUP2-Ptrp-NSDG-E187V. The pCUP2-Ptrp-NSDG-E187V is a plasmid that expresses NSDG-E187V under the trp promoter.

The NSDG-E187V is a mutant PHA synthetase in which aspartic acid at the 187th position from the N-terminus of the amino acid sequence of SEQ ID NO: 14 is substituted with valine.

(Production Example 34) Preparation of pCUP2-Ptrp-NSDG-E29N-A180K

Using as a template the pCUP2-Ptrp-NSDG prepared in Production Example 2, a DNA fragment having the nucleotide sequence of SEQ ID NO: 46 was amplified by PCR using a synthetic oligo DNA or the like. The DNA fragment was cloned into the pCUP2 vector in the same manner as in Production Example 2 to obtain pCUP2-Ptrp-NSDG-E29N-A180K. The pCUP2-Ptrp-NSDG-E29N-A180K is a plasmid that expresses NSDG-E29N-A180K under the tip promoter.

The NSDG-E29N-A180K is a mutant PHA synthetase in which aspartic acid at the 29th position from the N-terminus is substituted with asparagine and alanine at the 180th position is substituted with lysine in the amino acid sequence of SEQ ID NO: 14.

(Production Example 35) Preparation of pCUP2-Ptrp-NSDG-E29N-A180R

Using as a template the pCUP2-Ptrp-NSDG prepared in Production Example 2, a DNA fragment having the nucleotide sequence of SEQ ID NO: 47 was amplified by PCR using a synthetic oligo DNA or the like. The DNA fragment was cloned into the pCUP2 vector in the same manner as in Production Example 2 to obtain pCUP2-Ptrp-NSDG-E29N-

A180R. The pCUP2-Ptrp-NSDG-E29N-A180R is a plasmid that expresses NSDG-E29N-A180R under the trp promoter.

The NSDG-E29N-A180R is a mutant PHA synthetase in which aspartic acid at the 29th position from the N-terminus is substituted with asparagine and alanine at the 180th position is substituted with arginine in the amino acid sequence of SEQ ID NO: 14.

(Production Example 36) Preparation of pCUP2-Ptrp-NSDG-E29S-A180K

Using as a template the pCUP2-Ptrp-NSDG prepared in Production Example 2, a DNA fragment having the nucleotide sequence of SEQ ID NO: 48 was amplified by PCR using a synthetic oligo DNA or the like. The DNA fragment was cloned into the pCUP2 vector in the same manner as in Production Example 2 to obtain pCUP2-Ptrp-NSDG-E29S-A180K. The pCUP2-Ptrp-NSDG-E29S-A180K is a plasmid that expresses NSDG-E29S-A180K under the trp promoter.

The NSDG-E29S-A180K is a mutant PHA synthetase in which aspartic acid at the 29th position from the N-terminus is substituted with serine and alanine at the 180th position is substituted with lysine in the amino acid sequence of SEQ ID NO: 14.

(Production Example 37) Preparation of pCUP2-Ptrp-NSDG-E29S-A180R

Using as a template the pCUP2-Ptrp-NSDG prepared in Production Example 2, a DNA fragment having the nucleotide sequence of SEQ ID NO: 49 was amplified by PCR using a synthetic oligo DNA or the like. The DNA fragment was cloned into the pCUP2 vector in the same manner as in Production Example 2 to obtain pCUP2-Ptrp-NSDG-E29S-A180R. The pCUP2-Ptrp-NSDG-E29S-A180R is a plasmid that expresses NSDG-E29S-A180R under the trp promoter.

The NSDG-E29S-A180R is a mutant PHA synthetase in which aspartic acid at the 29th position from the N-terminus is substituted with serine and alanine at the 180th position is substituted with arginine in the amino acid sequence of SEQ ID NO: 14.

(Production Example 38) Preparation of pCUP2-Ptrp-NSDG-E29N-A180K-S389T

Using as a template the pCUP2-Ptrp-NSDG prepared in Production Example 2, a DNA fragment having the nucleotide sequence of SEQ ID NO: 50 was amplified by PCR using a synthetic oligo DNA or the like. The DNA fragment was cloned into the pCUP2 vector in the same manner as in Production Example 2 to obtain pCUP2-Ptrp-NSDG-E29N-A180K-S389T. The pCUP2-Ptrp-NSDG-E29N-A180K-S389T is a plasmid that expresses NSDG-E29N-A180K-S389T under the trp promoter.

The NSDG-E29N-A180K-S389T is a mutant PHA synthetase in which aspartic acid at the 29th position from the N-terminus is substituted with asparagine, alanine at the 180th position is substituted with lysine and serine at the 389th position is substituted with threonine in the amino acid sequence of SEQ ID NO: 14.

(Production Example 39) Preparation of pCUP2-Ptrp-NSDG-E29N-A180R-S389T

Using as a template the pCUP2-Ptrp-NSDG prepared in Production Example 2, a DNA fragment having the nucleotide sequence of SEQ ID NO: 51 was amplified by PCR using a synthetic oligo DNA or the like. The DNA fragment was cloned into the pCUP2 vector in the same manner as in Production Example 2 to obtain pCUP2-Ptrp-NSDG-E29N-A180R-S389T. The pCUP2-Ptrp-NSDG-E29N-A180R-S389T is a plasmid that expresses NSDG-E29N-A180R-S389T under the trp promoter.

The NSDG-E29N-A180R-S389T is a mutant PHA synthetase in which aspartic acid at the 29th position from the N-terminus is substituted with asparagine, alanine at the 180th position is substituted with arginine and serine at the 389th position is substituted with threonine in the amino acid sequence of SEQ ID NO: 14.

(Production Example 40) Preparation of pCUP2-Ptrp-NSDG-E29S-A180K-S389T

Using as a template the pCUP2-Ptrp-NSDG prepared in Production Example 2, a DNA fragment having the nucleotide sequence of SEQ ID NO: 52 was amplified by PCR using a synthetic oligo DNA or the like. The DNA fragment was cloned into the pCUP2 vector in the same manner as in Production Example 2 to obtain pCUP2-Ptrp-NSDG-E29S-A180K-S389T. The pCUP2-Ptrp-NSDG-E29S-A180K-S389T is a plasmid that expresses NSDG-E29S-A180K-S389T under the trp promoter.

The NSDG-E29S-A180K-S389T is a mutant PHA synthetase in which aspartic acid at the 29th position from the N-terminus is substituted with serine, alanine at the 180th position is substituted with lysine and serine at the 389th position is substituted with threonine in the amino acid sequence of SEQ ID NO: 14.

(Production Example 41) Preparation of pCUP2-Ptrp-NSDG-E29S-A180R-S389T

Using as a template the pCUP2-Pup-NSDG prepared in Production Example 2, a DNA fragment having the nucleotide sequence of SEQ ID NO: 53 was amplified by PCR using a synthetic oligo DNA or the like. The DNA fragment was cloned into the pCUP2 vector in the same manner as in Production Example 2 to obtain pCUP2-Ptrp-NSDG-E29S-A180R-S389T. The pCUP2-Ptrp-NSDG-E29S-A180R-S389T is a plasmid that expresses NSDG-E29S-A180R-S389T under the trp promoter.

The NSDG-E29S-A180R-S389T is a mutant PHA synthetase in which aspartic acid at the 29th position from the N-terminus is substituted with serine, alanine at the 180th position is substituted with arginine and serine at the 389th position is substituted with threonine in the amino acid sequence of SEQ ID NO: 14.

(Production Example 42) Introduction of Plasmids to H16 ΔphaC1 Ptrc-phaJ4b dZ1,2,6

First, the H16 ΔphaC1 Ptrc-phaJ4b dZ1,2,6 strain prepared in Production Example 1 was cultured overnight in Nutrient Broth medium (DIFCO). 0.5 mL of the obtained culture solution was inoculated in 100 mL of Nutrient Broth medium, and cultured at 30° C. for 3 hours. The obtained culture solution was quickly cooled on ice, the bacterial cells were collected, and washed thoroughly with ice-cooled distilled water, and the obtained bacterial cells were suspended in 2 mL of distilled water. The bacterial cell liquid was mixed with the pCUP2-Ptrp-NSDG plasmid solution prepared in Production Example 2, and the mixture was poured into a cuvette to perform electroporation. Electroporation was performed under the conditions of a voltage of 1.5 kV, a resistance of 800Ω and a current of 25 μF using a MicroPulser electroporator (Bio Rad Inc.). After the electroporation, the bacterial cell solution was recovered, 5 mL, of Nutrient Broth medium was added, and the mixture was cultured at the 30° C. for 3 hours. The obtained culture solution was applied to Nutrient Agar medium containing 100 mg/L kanamycin sulfate. The culture was performed at the 30° C. for 3 days, and a strain containing a plasmid was obtained from the resulting colonies. The obtained strain was named H16 ΔphaC1 Ptrc-phaJ4b dZ1,2,6/pCUP2-Ptrp-NSDG strain.

The plasmids prepared in Production Examples 3 to 41 were introduced in the same manner as described above, and the thus-obtained strains were named H16 ΔphaC1 Ptrc-phaJ4b dZ1,2,6/pCUP2-Ptrp-NSDG-Q27S strain, H16 ΔphaC1 Ptrc-phaJ4b dZ1,2,6/pCUP2-Ptrp-NSDG-E29N strain, H16 ΔphaC1 Ptrc-phaJ4bdZ1,2,6/pCUP2-Ptrp-NSDG-E29S strain, H16ΔphaC1 Ptrc-phaJ4b dZ1,2,6/pCUP2-Ptrp-NSDG-R30G strain, H16 ΔphaC1 Ptrc-phaJ4b dZ1,2,6/pCUP2-Ptrp-NSDG-R30P strain, H16 ΔphaC1 Ptrc-phaJ4b dZ1,2,6/pCUP2-Ptrp-NSDG-T31P strain, H16 ΔphaC1 Ptrc-phaJ4b dZ1,2,6/pCUP2-Ptrp-NSDG-Q33I strain, H16 ΔphaC1 Ptrc-phaJ4b dZ1,2,6/pCUP2-Ptrp-NSDG-Q33L strain, H16 ΔphaC1 Ptrc-phaJ4b dZ1,2,6/pCUP2-Ptrp-NSDG-Q33V strain, H16 ΔphaC1 Ptrc-phaJ4b dZ1,2,6/pCUP2-Ptrp-NSDG-N39A strain, H16 ΔphaC1 Ptrc-phaJ4b dZ1,2,6/pCUP2-Ptrp-NSDG-N39C strain, H16 ΔphaC1 Ptrc-phaJ4b dZ1,2,6/pCUP2-Ptrp-NSDG-N39F strain, H16 ΔphaC1 Ptrc-phaJ4b dZ1,2,6/pCUP2-Ptrp-NSDG-N39H strain, H16 ΔphaC1 Ptrc-phaJ4b dZ1,2,6/pCUP2-Ptrp-NSDG-N39I strain, H16 ΔphaC1 Ptrc-phaJ4b dZ1,2,6/pCUP2-Ptrp-NSDG-N39M strain, H16 ΔphaC1 Ptrc-phaJ4b dZ1,2,6/pCUP2-Ptrp-NSDGN39Q strain, H16 ΔphaC1 Ptrc-phaJ4b dZ1,2,6/pCUP2-Ptrp-N SDG-N39W strain, H16 ΔphaC1 Ptrc-phaJ4b dZ1,2,6/pCUP2-Ptrp-NSDG-Q56P strain, H16 ΔphaC1 Ptrc-phaJ4b dZ1,2,6/pCUP2-Ptrp-NSDG-P106A strain, H16ΔphaC1 Ptrc-phaJ4b dZ1,2,6/pCUP2-Ptrp-NSDG-L129Q strain, H16 ΔphaC1 Ptrc-phaJ4b dZ1,2,6/pCUP2-Ptrp-NSDG-T144L strain, H16 ΔphaC1 Ptrc-phaJ4b dZ1,2,6/pCUP2-Ptrp-NSDG-K165V strain, H16 ΔphaC1 Ptrc-phaJ4b dZ1,2,6/pCUP2-Ptrp-NSDG-S170Q strain, H16 ΔphaC1 Ptrc-phaJ4b dZ1,2,6/pCUP2-Ptrp-NSDG-V176W strain, H16 ΔphaC1 Ptrc-phaJ4b dZ1,2,6/pCUP2-Ptrp-NSDG-L179Q strain, H16 ΔphaC1 Ptrc-phaJ4b dZ1,2,6/pCUP2-Ptrp-NSDG-179R strain, H16 ΔphaC1 Ptrc-phaJ4b dZ1,2,6/pCUP2-Ptrp-NSDG-A180G strain, H16 ΔphaC1 Ptrc-phaJ4b dZ1,2,6/pCUP2-Ptrp-NSDG-A180K strain, H16 ΔphaC1 Ptrc-phaJ4b dZ1,2,6/pCUP2-Ptrp-NSDG-A180R strain, H16 ΔphaC1 Ptrc-phaJ4b dZ1,2,6/pCUP2-Ptrp-NSDG-L181Y strain, H16 ΔphaC1 Ptrc-phaJ4bdZ1,2,6/pCUP2-Ptrp-NSDG-E187V strain, H16ΔphaC1 Ptrc-phaJ4b dZ1,2,6/pCUP2-Ptrp-NSDG-E29N-A180K strain, H16 ΔphaC1 Ptrc-phaJ4b dZ1,2,6/pCUP2-Ptrp-NSDG-E29N-A180R strain, H16 ΔphaC1 Ptrc-phaJ4b dZ1,2,6/pCUP2-Ptrp-NSDG-E29S-A180K strain, H16 ΔphaC1 Ptrc-phaJ4b dZ1,2,6/pCUP2-Ptrp-NSDG-E29S-A180R strain, H16 ΔphaC1 Ptrc-phaJ4b dZ1,2,6/pCUP2-Ptrp-NSDG-E29N-A180K-S389T strain, H16 ΔphaC1 Ptrc-phaJ4b dZ1,2,6/pCUP2-Ptrp-NSDG-E29N-A180R-S389T strain, H16 ΔphaC1 Ptrc-phaJ4b dZ1,2,6/pCUP2-Ptrp-NSDG-E29S-A180K-S389T strain, and H16 ΔphaC1 Ptrc-phaJ4b dZ1,2,6/pCUP2-Ptrp-NSDG-E29S-A180R-S389T strain, respectively.

(Method for Analyzing 3HH Ratio in PHA)

To about 20 mg of dried bacterial cells containing PHA, 1 mL of a sulfuric acid-methanol mixed liquid (15:85) and 1 mL of chloroform were added, the bottle was tightly capped, and the mixture was heated to 100° C. for 140 minutes to obtain methyl ester as a PHA degradation product. The product was cooled, 0.5 mL of deionized water was then added thereto, and the mixture was thoroughly stirred, and then left standing until the aqueous layer and the organic layer were separated. Thereafter, the monomer unit composition of the PHA degradation product in the separated organic layer was analyzed by capillary gas chromatography. The 3HH ratio was calculated from the obtained peak area.

GC-17A manufactured by Shimadzu Corporation was used as a gas chromatography, and NEUTRA BOND-1 (column length: 25 m, column inner diameter: 0.25 mm and liquid film thickness: 0.4 μm) manufactured by GL Science Inc. He was used as a carrier gas, the column inlet pressure was set to 100 kPa, and 1 μL of the sample was injected. The temperature was raised from the initial temperature of 50° C. to 200° C. at a rate of 8° C./min, and raised from 200° C. to 290° C. at a rate of 30° C./min.

(Comparative Example 1) Production of PHA by H16 ΔphaC1 Ptrc-phaJ4b dZ1,2,6/pCUP2-Ptrp-NSDG Strain The seed medium had a composition of meat extract: 10 g/L, bactotryptone: 10 g/L, yeast extract: 2 g/L, sodium dihydrogen phosphate dodecahydrate: 9 g/L, dipotassium hydrogen phosphate: 1.5 g/L and Kanamycine sulfate: 100 μg/L.

The PHA production medium had a composition of disodium hydrogen phosphate dodecahydrate: 11 g/L, dipotassium hydrogen phosphate: 1.9 g/L, ammonium sulfate: 1.3 g/L, magnesium solution: 5 mL/L and a minute-amount metal salt solution: 1 mL/L.

The magnesium solution was prepared by dissolving 200 g/L magnesium sulfate heptahydrate in water. The minute-amount metal salt solution was prepared by dissolving 0.218 g/L cobalt chloride hexahydrate, 16.2 g/L iron (III) chloride hexahydrate, 10.3 g/L calcium chloride dihydrate, 0.118 g/L nickel chloride hexahydrate and 0.156 g/L copper sulfate pentahydrate in 0.1 N hydrochloride.

50 μL of a glycerol stock solution of the H16 ΔphaC1 Ptrc-phaJ4b dZ1,2,6/pCUP2-Ptrp-NSDG strain prepared in Production Example 42 was inoculated in 10 mL of a seed medium, and cultured with shaking at 30° C. for 24 hours. The obtained culture solution was used as a pre-culture solution.

PHA production culture was performed in flasks. 50 mL of the PHA production medium was put in a 500 mL shaking flask. Immediately before inoculation, 250 μL of the magnesium solution, 50 μL of the minute-amount metal solution, and 1 g of palm kernel oil were added. After the medium was prepared, 500 μL of the pre-culture solution was inoculated in the shaking flask, and cultured with shaking at 30° C. for 72 hours. After completion of the culture, the bacterial cells were recovered from 10 mL of the culture solution, washed with ethanol, and vacuum-dried at 60° C. to obtain dried bacterial cells containing PHA, and the weight of the dried bacterial cells was measured.

Tables 1 and 2 show the results of the dried bacterial cell weight and the 3HH ratio.

(Examples 1 to 39) Production of PHA by Plasmid-Introduced Strains

The following strains produced in Production Example 42 were cultured in the same manner as in Comparative Example 1, and the weight of dried bacterial cells and the 3HH ratio were analyzed: H16 ΔphaC1 Ptrc-phaJ4b dZ1,2,6/pCUP2-Ptrp-NSDG-Q27S strain (Example 1), H16 ΔphaC1 Ptrc-phaJ4b dZ1,2,6/pCUP2-Ptrp-NSDG-E29N strain (Example 2), H16 ΔphaC1 Ptrc-phaJ4b dZ1,2,6/pCUP2-Ptrp-NSDG-E29S strain (Example 3), H16ΔphaC1 Ptrc-phaJ4b dZ1,2,6/pCUP2-Ptrp-NSDG-R30G strain (Example 4), H16 ΔphaC1 Ptrc-phaJ4b dZ1,2,6/pCUP2-Ptrp-NSDG-R30P strain (Example 5), H16 ΔphaC1 Ptrc-phaJ4b dZ1,2,6/pCUP2-Ptrp-NSDG-T31P strain (Example 6), H16 ΔphaC1 Ptrc-phaJ4b dZ1,2,6/pCUP2-Ptrp-NSDG-Q33I strain (Example 7), H16 ΔphaC1 Ptrc-phaJ4b dZ1,2,6/pCUP2-Ptrp-NSDG-Q33L strain (Example 8), H16 ΔphaC1 Ptrc-phaJ4b dZ1,2,6/pCUP2-Ptrp-NSDG-Q33V strain (Example 9), H16 ΔphaC1 Ptrc-phaJ4b dZ1,2,6/pCUP2-Ptrp-NSDG-N39A strain (Example 10), H16 ΔphaC1 Ptrc-phaJ4b dZ1,2,6/pCUP2-Ptrp-NSDG-N39C strain (Example 11), H16 ΔphaC1 Ptrc-phaJ4b dZ1,2,6/pCUP2-Ptrp-NSDG-N39F strain (Example 12), H16 ΔphaC1 Ptrc-phaJ4b dZ1,2,6/pCUP2-Ptrp-NSDG-N39H strain (Example 13), H16 ΔphaC1 Ptrc-phaJ4b dZ1,2,6/pCUP2-Ptrp-NSDG-N39I strain (Example 14), H16 ΔphaC1 Ptrc-phaJ4b dZ1,2,6/pCUP2-Ptrp-NSDG-N39M strain (Example 15), H16 ΔphaC1 Ptrc-phaJ4b dZ1,2,6/pCUP2-Ptrp-NSDG-N39Q strain (Example 16), H16 ΔphaC1 Ptrc-phaJ4b dZ1,2,6/pCUP2-Ptrp-NSDG-N39W strain (Example 17), H16 ΔphaC1 Ptrc-phaJ4b dZ1,2,6/pCUP2-Ptrp-NSDG-Q56P strain (Example 18), H16 ΔphaC1 Ptrc-phaJ4b dZ1,2,6/pCUP2-Ptrp-NSDG-P106A strain (Example 19), H16 ΔphaC1 Ptrc-phaJ4b dZ1,2,6/pCUP2-Ptrp-NSDG-L129Q strain (Example 20), H16 ΔphaC1 Ptrc-phaJ4b dZ1,2,6/pCUP2-Ptrp-NSDG-T144L strain (Example 21), H16 ΔphaC1 Ptrc-phaJ4b dZ1,2,6/pCUP2-Ptrp-NSDG-K165V strain (Example 22), H16 ΔphaC1 Ptrc-phaJ4b dZ1,2,6/pCUP2-Ptrp-NSDG-S170Q strain (Example 23), H16 ΔphaC1 Ptrc-phaJ4b dZ1,2,6/pCUP2-Ptrp-NSDG-V176W strain (Example 24), H16 ΔphaC1 Ptrc-phaJ4b dZ1,2,6/pCUP2-Ptrp-NSDG-L179Q strain (Example 25), H16 ΔphaC1 Ptrc-phaJ4b dZ1,2,6/pCUP2-Ptrp-NSDG-l79R strain (Example 26), H16 ΔphaC1 Ptrc-phaJ4b dZ1,2,6/pCUP2-Ptrp-NSDG-A180G strain (Example 27), H16 ΔphaC1 Ptrc-phaJ4b dZ1,2,6/pCUP2-Ptrp-NSDG-A180K strain (Example 28), H16 ΔphaC1 Ptrc-phaJ4b dZ1,2,6/pCUP2-Ptrp-NSDG-A180R strain (Example 29), H16 ΔphaC1 Ptrc-phaJ4b dZ1,2,6/pCUP2-Ptrp-NSDG-L181Y strain (Example 30), H16 ΔphaC1 Ptrc-phaJ4bdZ1,2,6/pCUP2-Ptrp-NSDG-E187V strain (Example 31), H16 ΔphaC1 Ptrc-phaJ4b dZ1,2,6/pCUP2-Ptrp-NSDG-E29N-A180K strain (Example 32), H16 ΔphaC1 Ptrc-phaJ4b dZ1,2,6/pCUP2-Ptrp-NSDG-E29N-A180R strain (Example 33), H16 ΔphaC1 Ptrc-phaJ4b dZ1,2,6/pCUP2-Ptrp-NSDG-E29S-A180K strain (Example 34), H16 ΔphaC1 Ptrc-phaJ4b dZ1,2,6/pCUP2-Ptrp-NSDG-E29S-A180R strain (Example 35), H16 ΔphaC1 Ptrc-phaJ4b dZ1,2,6/pCUP2-Ptrp-NSDG-E29N-A180K-S389T strain (Example 36), H16 ΔphaC1 Ptrc-phaJ4b dZ1,2,6/pCUP2-Ptrp-NSDG-E29N-A180R-S389T strain (Example 37), H16 ΔphaC1 Ptrc-phaJ4b dZ1,2,6/pCUP2-Ptrp-NSDG-E29S-A180K-S389T strain (Example 38), and H16 ΔphaC1 Ptrc-phaJ4b dZ1,2,6/pCUP2-Ptrp-NSDG-E29S-A180R-S389T strain (Example 39). Tables 1 and 2 show the results.

TABLE 1

| | Mutation introduced into NSDG | Weight of dried bacterial cells (g/L) | 3HH ratio (mol%) | Comparison in 3HH ratio to Comparative Example 1 |
|---|---|---|---|---|
| Example 1 | Q27S | 22.1 | 15.71 | 101.9% |
| Example 2 | E29N | 21.4 | 17.42 | 113.0% |
| Example 3 | E29S | 21.0 | 16.79 | 108.9% |
| Example 4 | R30G | 21.0 | 16.53 | 107.2% |
| Example 5 | R30P | 21.0 | 16.55 | 107.3% |
| Example 6 | T31P | 21.9 | 16.16 | 104.8% |
| Example 7 | Q33I | 23.4 | 16.69 | 108.2% |
| Example 8 | Q33L | 22.0 | 16.40 | 106.4% |
| Example 9 | Q33V | 22.0 | 16.39 | 106.3% |
| Example 10 | N39A | 21.3 | 16.71 | 108.4% |
| Example 11 | N39C | 19.6 | 16.84 | 109.2% |
| Example 12 | N39F | 20.3 | 16.74 | 108.6% |
| Example 13 | N39H | 21.3 | 17.49 | 113.4% |
| Example 14 | N39I | 19.4 | 17.7 | 114.8% |
| Example 15 | N39M | 21.7 | 17.46 | 113.2% |
| Example 16 | N39Q | 20.4 | 17.22 | 111.7% |
| Example 17 | N39W | 21.6 | 16.64 | 107.9% |
| Example 18 | Q56P | 21.1 | 16.88 | 109.5% |
| Example 19 | P106A | 22.6 | 16.35 | 106.0% |
| Example 20 | L129Q | 22.6 | 16.38 | 106.2% |
| Example 21 | T144L | 24.0 | 16.72 | 108.4% |
| Example 22 | K165V | 23.4 | 16.54 | 107.3% |
| Example 23 | S170Q | 22.3 | 17.05 | 110.6% |
| Example 24 | V176W | 15.5 | 18.04 | 117.0% |
| Example 25 | L179Q | 22.3 | 17.36 | 112.6% |
| Example 26 | L179R | 22.6 | 16.83 | 109.1% |
| Example 27 | A180G | 22.9 | 16.57 | 107.5% |
| Example 28 | A180K | 22.2 | 17.8 | 115.4% |
| Example 29 | A180R | 22.6 | 17.69 | 114.7% |
| Example 30 | L181Y | 20.6 | 17.58 | 114.0% |
| Example 31 | E187V | 22.1 | 16.83 | 109.1% |
| Comparative Example 1 | — | 21.5 | 15.42 | 100.0% |

TABLE 2

| | Mutation introduced into NSDG | Weight of dried bacterial cells (g/L) | 3HH ratio (mol %) | Comparison in 3HH ratio to Comparative Example 1 |
|---|---|---|---|---|
| Example 32 | E29N-A180K | 19.9 | 18.13 | 117.6% |
| Example 33 | E29N-A180R | 20.9 | 17.85 | 115.8% |
| Example 34 | E29S-A180K | 21.1 | 17.63 | 114.3% |
| Example 35 | E29S-A180R | 22.0 | 17.59 | 114.1% |
| Example 36 | E29N-A180K-S389T | 18.6 | 20.64 | 133.9% |
| Example 37 | E29N-A180R-S389T | 20.0 | 20.69 | 134.2% |
| Example 38 | E29S-A180K-S389T | 23.8 | 19.74 | 128.0% |
| Example 39 | E29S-A180R-S389T | 16.9 | 19.79 | 128.3% |
| Comparative Example 1 | — | 21.5 | 15.42 | 100.0% |

DISCUSSION

The results in Table 1 show that for the PHA synthetases of Examples 1 to 31 with a mutation of Q27S, E29N, E29S, R30G, R30P, T31P, Q33I, Q33L, Q33V, N39A, N39C, N39F, N39H, N39I, N39M, N39Q, N39W, Q56P, P106A, L129Q, T144L, K165V, S170Q, V176W, L179Q, L179R, A180G, A180K A180R, L181Y or E187V, there was an increase in 3HH ratio. In addition, it was considered that there was no change in PHA productivity because in all examples, the weight of dried bacterial cells was almost the same as that in Comparative Example 1. The above results show that the PHA synthetases having these mutations are useful for producing PHA with a high 3HH ratio while maintaining polymer productivity.

In addition, from Examples 1 to 9, it is apparent that introduction of a mutation to the amino acids at the 27th to 33rd positions from the N-terminus of the amino acid sequence of the PHA synthetase is particularly effective for improving the 3HH ratio. Further, from Examples 10 to 17, it is apparent that introduction of a mutation to asparagine at the 39th position from the N-terminus of the amino acid sequence of the PHA synthetase is particularly effective for improving the 3HH ratio. In addition, from Examples 18 to 23, it is apparent that introduction of a mutation to the amino acids at the 56th, 106th, 129th, 144th, 165th and 170th positions from the N-terminus of the amino acid sequence of the PHA synthetase is effective for improving the 3HH ratio. In addition, from Examples 24 to 31, it is apparent that introduction of a mutation to the amino acids at the 172nd to 187th positions from the N-terminus of the amino acid sequence of the PHA synthetase is particularly effective for improving the 3HH ratio. From the above results, persons skilled in the art can easily presume that the amino acids at the 27th to 33rd, 39th, 56th, 106th, 129th, 144th, 165th, 170th and 172nd to 187th positions from the N-terminus of the amino acid sequence of the PHA synthetase are extremely effective mutation introduction sites for improving the 3HH composition.

Next, from Examples 32 to 35 shown in Table 2, it is apparent that any combination of the mutation of E29N or E29S with the mutation of A180K or A180R produces an additive effect due to mutation duplication. This reveals that when two or more of the mutations to the amino acids at the 27th to 33rd, 39th, 56th, 106th, 129th, 144th, 165th, 170th and 172nd to 187th positions from the N-terminus of the amino acid sequence of the PHA synthetase are arbitrarily combined, and duplicately introduced, it is possible to obtain a mutant PHA synthetase useful for further improving the 3HH composition.

Likewise, from Examples 36 to 39 shown in Table 2, it is apparent that when the mutation of E29N-A180K, E29N-A180R, E29S-A180K or E29S-A180R and the mutation of S389T are combined, and duplicately introduced, the 3HH ratio is further improved. It has been already known that as mutations to S389, S389C, S389F, S389T and S389T are effective for improving the 3HH composition. From the above, it is evident that when any of the mutations to the amino acids at the 27th to 33rd, 39th, 56th, 106th, 129th, 144th, 165th, 170th and 172nd to 187th positions from the N-terminus of the amino acid sequence of the PHA synthetase and the mutation of S389C, S389F, S389I or S389T are combined, and duplicately introduced, it is possible to obtain a mutant PHA synthetase useful for further improving the 3HH composition.

The invention claimed is:

1. A mutant polyhydroxyalkanoate synthetase having at least 95% sequence identity with the amino acid sequence of SEQ ID NO: 1 and having at least one mutation selected from the group consisting of (A), (B), (C), and (n):
mutation (A): a substitution of at least one of amino acids at 27th to 33rd positions from the N-terminus of the amino acid sequence of SEQ ID NO: 1 with another amino acid;
mutation (B): a substitution of at least one of amino acids at 39th, 56th, 106th, 129th, 144th, 165th and 170th positions from the N-terminus of the amino acid sequence of SEQ ID NO: 1 with another amino acid;
mutation (C): a substitution of at least one of amino acids at 172nd to 187th positions except 179th position from the N-terminus of the amino acid sequence of SEQ ID NO: 1 with another amino acid, and
mutation (n): a substitution of leucine at the 179th position from the N-terminus of the amino acid sequence of SEQ ID NO: 1 with arginine.

2. The mutant polyhydroxyalkanoate synthetase according to claim 1, wherein the at least one mutation selected from the group consisting of (A), (B), (C), and (n) is at least one mutation selected from the group consisting of (a) to (q):
mutation (a): a substitution of glutamine at the 27th position from the N-terminus of the amino acid sequence of SEQ ID NO: 1 with another amino acid;
mutation (b): a substitution of glutamic acid at the 29th position from the N-terminus of the amino acid sequence of SEQ ID NO: 1 with another amino acid;
mutation (c): a substitution of arginine at the 30th position from the N-terminus of the amino acid sequence of SEQ ID NO: 1 with another amino acid;
mutation (d): a substitution of threonine at the 31st position from the N-terminus of the amino acid sequence of SEQ ID NO: 1 with another amino acid;
mutation (e): a substitution of glutamine at the 33rd position from the N-terminus of the amino acid sequence of SEQ ID NO: 1 with another amino acid;
mutation (f): a substitution of asparagine at the 39th position from the N-terminus of the amino acid sequence of SEQ ID NO: 1 with another amino acid;
mutation (g): a substitution of glutamine at the 56th position from the N-terminus of the amino acid sequence of SEQ ID NO: 1 with another amino acid;
mutation (h): a substitution of proline at the 106th position from the N-terminus of the amino acid sequence of SEQ ID NO: 1 with another amino acid;
mutation (i): a substitution of leucine at the 129th position from the N-terminus of the amino acid sequence of SEQ ID NO: 1 with another amino acid;
mutation (j): a substitution of threonine at the 144th position from the N-terminus of the amino acid sequence of SEQ ID NO: 1 with another amino acid;
mutation (k): a substitution of lysine at the 165th position from the N-terminus of the amino acid sequence of SEQ ID NO: 1 with another amino acid;
mutation (l): a substitution of serine at the 170th position from the N-terminus of the amino acid sequence of SEQ ID NO: 1 with another amino acid;
mutation (m): a substitution of valine at the 176th position from the N-terminus of the amino acid sequence of SEQ ID NO: 1 with another amino acid;
mutation (n): a substitution of leucine at the 179th position from the N-terminus of the amino acid sequence of SEQ ID NO: 1 with arginine;
mutation (o): a substitution of alanine at the 180th position from the N-terminus of the amino acid sequence of SEQ ID NO: 1 with another amino acid;
mutation (p): a substitution of leucine at the 181st position from the N-terminus of the amino acid sequence of SEQ ID NO: 1 with another amino acid; and
mutation (q): a substitution of glutamic acid at the 187th position from the N-terminus of the amino acid sequence of SEQ ID NO: 1 with another amino acid.

3. The mutant polyhydroxyalkanoate synthetase according to claim 2, wherein the mutation (a) is a substitution of glutamine at the 27th position from the N-terminus of the amino acid sequence of SEQ ID NO: 1 with serine.

4. The mutant polyhydroxyalkanoate synthetase according to claim 2, wherein the mutation (b) is a substitution of glutamic acid at the 29th position from the N-terminus of the amino acid sequence of SEQ ID NO: 1 with asparagine or serine.

5. The mutant polyhydroxyalkanoate synthetase according to claim 2, wherein the mutation (c) is a substitution of arginine at the 30th position from the N-terminus of the amino acid sequence of SEQ ID NO: 1 with glycine or proline.

6. The mutant polyhydroxyalkanoate synthetase according to claim 2, wherein the mutation (d) is a substitution of threonine at the 31st position from the N-terminus of the amino acid sequence of SEQ ID NO: 1 with proline.

7. The mutant polyhydroxyalkanoate synthetase according to claim 2, wherein the mutation (e) is a substitution of glutamine at the 33rd position from the N-terminus of the amino acid sequence of SEQ ID NO: 1 with isoleucine, leucine or valine.

8. The mutant polyhydroxyalkanoate synthetase according to claim 2, wherein the mutation (f) is a substitution of asparagine at the 39th position from the N-terminus of the amino acid sequence of SEQ ID NO: 1 with alanine, cysteine, phenylalanine, histidine, isoleucine, methionine, glutamine or tryptophan.

9. The mutant polyhydroxyalkanoate synthetase according to claim 2, wherein the mutation (g) is a substitution of glutamine at the 56th position from the N-terminus of the amino acid sequence of SEQ ID NO: 1 with proline.

10. The mutant polyhydroxyalkanoate synthetase according to claim 2, wherein the mutation (h) is a substitution of proline at the 106th position from the N-terminus of the amino acid sequence of SEQ ID NO: 1 with alanine.

11. The mutant polyhydroxyalkanoate synthetase according to claim 2, wherein the mutation (i) is a substitution of leucine at the 129th position from the N-terminus of the amino acid sequence of SEQ ID NO: 1 with glutamine.

12. The mutant polyhydroxyalkanoate synthetase according to claim 2, wherein the mutation (j) is a substitution of threonine at the 144th position from the N-terminus of the amino acid sequence of SEQ ID NO: 1 with leucine.

13. The mutant polyhydroxyalkanoate synthetase according to claim 2, wherein the mutation (k) is a substitution of lysine at the 165th position from the N-terminus of the amino acid sequence of SEQ ID NO: 1 with valine.

14. The mutant polyhydroxyalkanoate synthetase according to claim 2, wherein the mutation (l) is a substitution of serine at the 170th position from the N-terminus of the amino acid sequence of SEQ ID NO: 1 with glutamine.

15. The mutant polyhydroxyalkanoate synthetase according to claim 2, wherein the mutation (m) is a substitution of valine at the 176th position from the N-terminus of the amino acid sequence of SEQ ID NO: 1 with tryptophan.

16. The mutant polyhydroxyalkanoate synthetase according to claim 2, wherein the mutation (o) is a substitution of alanine at the 180th position from the N-terminus of the amino acid sequence of SEQ ID NO: 1 with glycine, lysine or arginine.

17. The mutant polyhydroxyalkanoate synthetase according to claim 2, wherein the mutation (p) is a substitution of leucine at the 181st position from the N-terminus of the amino acid sequence of SEQ ID NO: 1 with tyrosine.

18. The mutant polyhydroxyalkanoate synthetase according to claim 2, wherein the mutation (q) is a substitution of glutamic acid at the 187th position from the N-terminus of the amino acid sequence of SEQ ID NO: 1 with valine.

19. The mutant polyhydroxyalkanoate synthetase according to claim 1, wherein the amino acid sequence comprising the mutation further comprises a mutation of substitution of asparagine at a 149th position from the N-terminus of the amino acid sequence of SEQ ID NO: 1 with serine.

20. The mutant polyhydroxyalkanoate synthetase according to claim 1, wherein the amino acid sequence comprising the mutation further comprises a mutation of substitution of aspartic acid at a 171st position from the N-terminus of the amino acid sequence of SEQ ID NO: 1 with glycine.

21. The mutant polyhydroxyalkanoate synthetase according to claim 1, wherein the amino acid sequence comprising the mutation further comprises a mutation of substitution of serine at a 389th position from the N-terminus of the amino acid sequence of SEQ ID NO: 1 with cysteine, isoleucine, threonine or valine.

22. A gene encoding the mutant polyhydroxyalkanoate synthetase according to claim 1.

23. A transformant comprising the gene according to claim 22.

24. The transformant according to claim 23, wherein a host is a bacterium.

25. The transformant according to claim 24, wherein the bacterium is a bacterium belonging to genus *Cupriavidus*.

26. The transformant according to claim 24, wherein the bacterium is *Cupriavidus necator*.

27. The transformant according to claim 24, wherein the bacterium is *Cupriavidus necator* H16.

28. A method for producing polyhydroxyalkanoate, comprising culturing the transformant according to claim 23.

29. The method for producing polyhydroxyalkanoate according to claim 28, wherein the polyhydroxyalkanoate comprises 3 hydroxyhexanoate as a monomer unit.

30. The method for producing polyhydroxyalkanoate according to claim 28, wherein the polyhydroxyalkanoate is a copolymer of 3-hydroxybutyrate and 3-hydroxyhexanoate.

* * * * *